(12) United States Patent
Kuniyoshi et al.

(10) Patent No.: US 12,147,462 B2
(45) Date of Patent: Nov. 19, 2024

(54) SUPPORT APPARATUS, GENERATION APPARATUS, ANALYSIS APPARATUS, SUPPORT METHOD, GENERATION METHOD, ANALYSIS METHOD, AND NON-TRANSITORY COMPUTER-READABLE RECORDING MEDIUM

(71) Applicant: Panasonic Corporation, Osaka (JP)

(72) Inventors: Fusataka Kuniyoshi, Tokyo (JP); Jun Ozawa, Nara (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 476 days.

(21) Appl. No.: 17/507,855

(22) Filed: Oct. 22, 2021

(65) Prior Publication Data

US 2022/0043847 A1    Feb. 10, 2022

Related U.S. Application Data

(63) Continuation of application No. PCT/JP2020/027532, filed on Jul. 15, 2020.

(30) Foreign Application Priority Data

Aug. 23, 2019  (JP) .................................. 2019-152719
Jun. 30, 2020  (JP) .................................. 2020-113388

(51) Int. Cl.
*G06F 17/28*     (2006.01)
*G06F 3/0482*    (2013.01)
(Continued)

(52) U.S. Cl.
CPC ........ *G06F 16/3334* (2019.01); *G06F 3/0482* (2013.01); *G06F 40/40* (2020.01);
(Continued)

(58) Field of Classification Search
CPC .......... G06V 30/19007; G06V 30/414; G06V 30/1983; G06V 30/10; G06F 40/40;
(Continued)

(56) References Cited

U.S. PATENT DOCUMENTS 10,013,467 B1    7/2018 Brogle
2014/0156670 A1  6/2014 Hosomi
2017/0300666 A1  10/2017 Wang

FOREIGN PATENT DOCUMENTS

CN    1819990 A  * 8/2006  ........... A61K 31/195
JP    11-053425    2/1999
(Continued)

OTHER PUBLICATIONS

International Search Report of PCT application No. PCT/JP2020/027532 dated Oct. 20, 2020.

*Primary Examiner* — Md S Elahee
(74) *Attorney, Agent, or Firm* — Wenderoth, Lind & Ponack, L.L.P.

(57) ABSTRACT

A support apparatus includes a generation apparatus and an analysis apparatus. The generation apparatus executes (a-1) to (a-5) with I=1 to n, and generates pieces of process information. The generation apparatus extracts material words from a document i in (a-1), extracts a treatment word i from the document i in (a-2), extracts a synthesis condition i from the document i in (a-3), extracts a characteristic value i related to a target material from the document i in (a-4), and associates the material words, the treatment word i, the synthesis condition i, and the characteristic value i with each other to generate process information i in (a-5). The analysis apparatus includes a combiner that generates composite process information including a common part common to the pieces of process information and different parts differ-
(Continued)

ent among the pieces of process information, and an outputter that outputs the composite process information.

24 Claims, 59 Drawing Sheets

(51) Int. Cl.
*G06F 16/33* (2019.01)
*G06F 40/40* (2020.01)
*G06V 30/414* (2022.01)
*G06F 40/284* (2020.01)
*G06V 30/10* (2022.01)

(52) U.S. Cl.
CPC .......... *G06V 30/414* (2022.01); *G06F 40/284* (2020.01); *G06V 30/10* (2022.01)

(58) Field of Classification Search
CPC ...... G06F 40/55; G06F 40/284; G06F 3/0482; G06F 40/216; G06F 16/3334; G16C 20/10; A61K 31/195
USPC .......................................................... 704/9
See application file for complete search history.

(56) References Cited

FOREIGN PATENT DOCUMENTS

| | | |
|---|---|---|
| JP | 2010-009257 | 1/2010 |
| WO | 2009/157176 | 12/2009 |
| WO | 2012/176374 | 12/2012 |

* cited by examiner

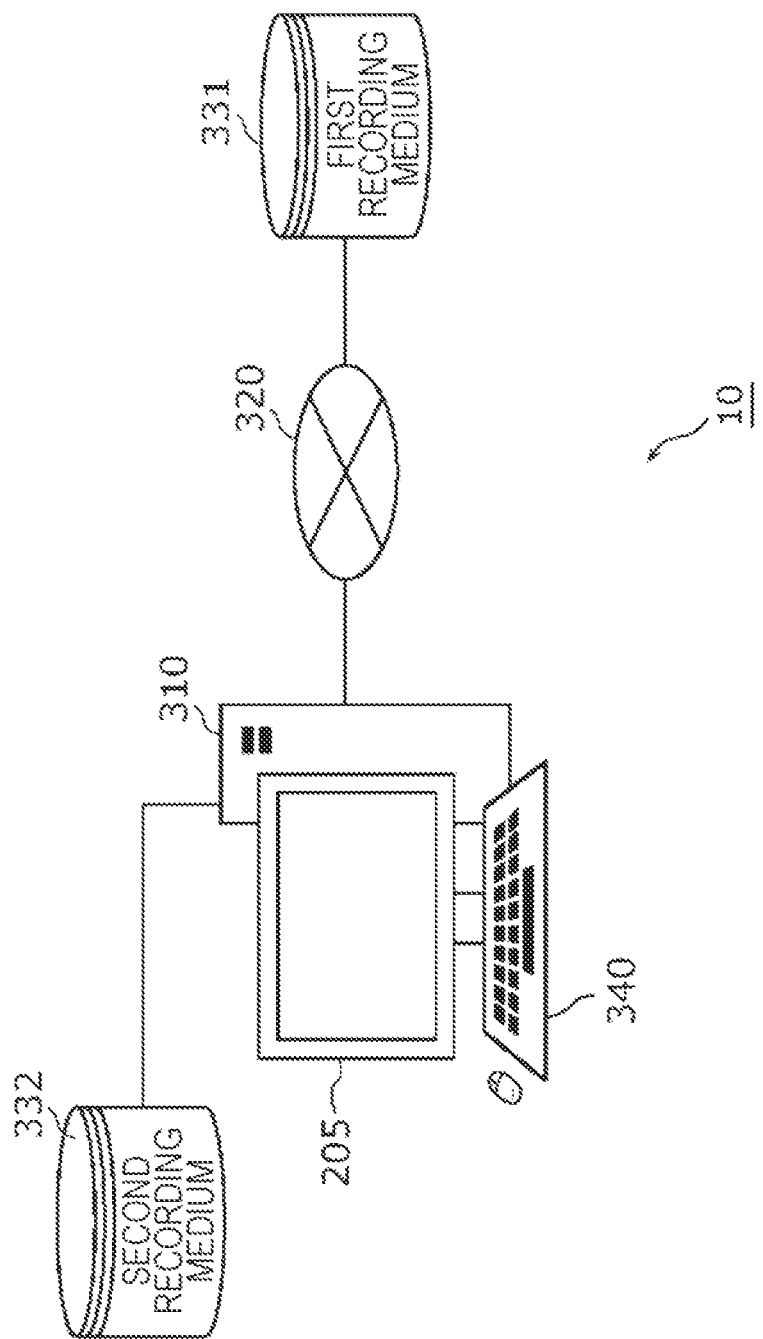

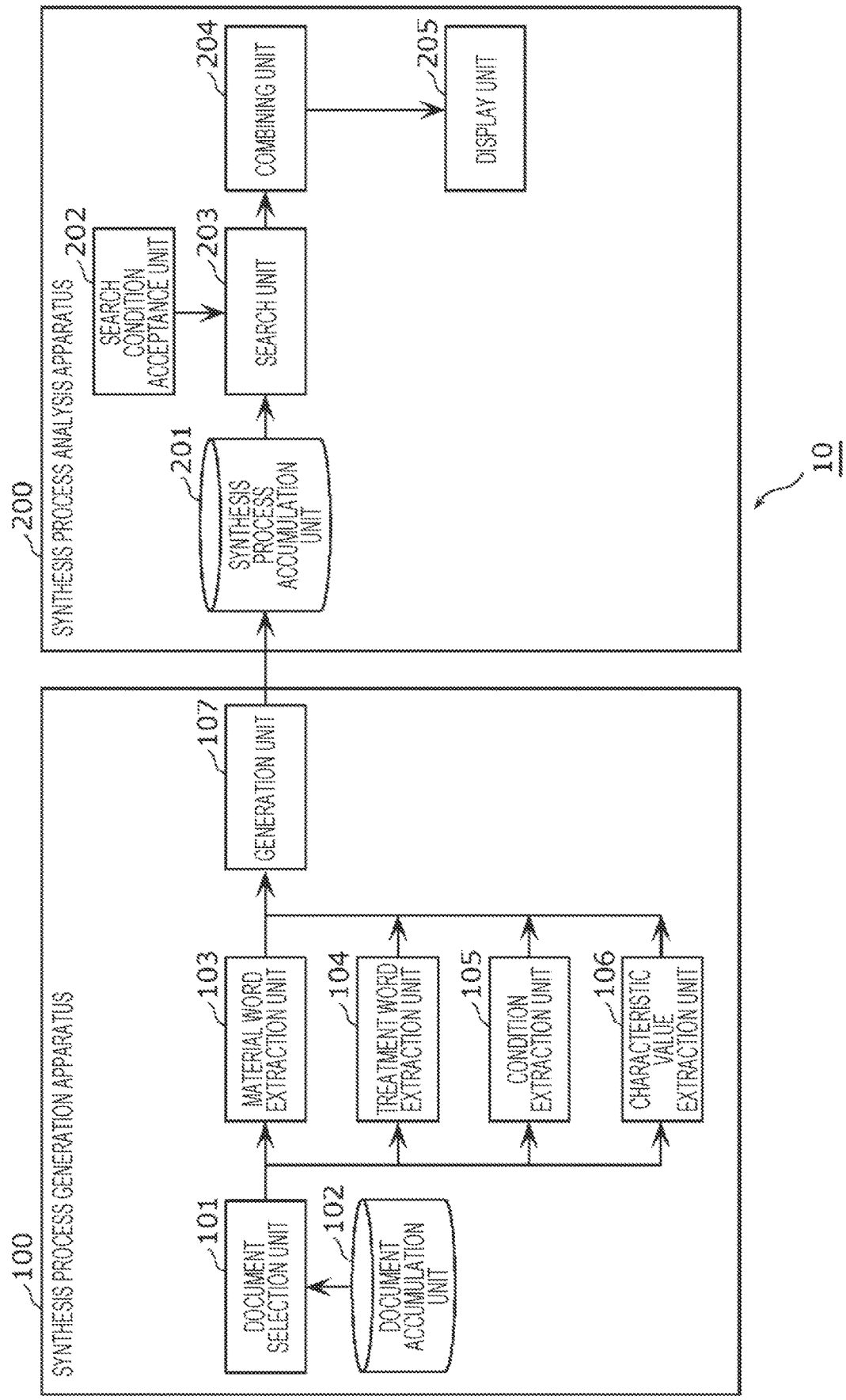

FIG. 3A (a) MATERIAL WORD DICTIONARY

| MATERIAL WORD | STARTING/TARGET MATERIAL |
|---|---|
| $CH_3OH$ | STARTING MATERIAL |
| $LiO_3$ | STARTING MATERIAL |
| $M_2CO_3$ | STARTING MATERIAL |
| $Li_2CO_3$ | STARTING MATERIAL |
| $MgO$ | STARTING MATERIAL |
| $TiO_2$ | STARTING MATERIAL |
| $NH_4H_2PO_4$ | STARTING MATERIAL |
| ... | ... |
| $LiNi_{0.8}Co_{0.2}O_2$ | TARGET MATERIAL |
| $LiFe(WO_4)_2$ | TARGET MATERIAL |
| $Li_4Ti_5O_{12}$ | TARGET MATERIAL |
| $Li_{1.1}Mg_{0.6}Ti_{1.9}(PO_4)_3$ | TARGET MATERIAL |
| ... | ... |

(b) TREATMENT WORD DICTIONARY

| TREATMENT WORD | ATTRIBUTE |
|---|---|
| heat | HEAT TREATMENT |
| anneal | ANNEALING TREATMENT |
| sinter | SINTERING TREATMENT |
| mix | MIXING TREATMENT |
| cool | COOLING TREATMENT |
| dry | DRYING TREATMENT |
| press | PRESSURIZATION TREATMENT |
| dissolve | DISSOLUTION TREATMENT |
| add | ADDING TREATMENT |
| ground | GRINDING TREATMENT |
| mill | MILLING TREATMENT |
| ... | ... |

FIG. 3B (a) CONDITION WORD DICTIONARY

| SYNTHESIS CONDITION WORD | ATTRIBUTE | EXAMPLE |
|---|---|---|
| °C | TEMPERATURE | at 900°C |
| K | TEMPERATURE | at 300~400 K |
| Room Temperature | TEMPERATURE | at room temperature |
| hours | TIME | for 5 hours |
| air | AIR | under air |
| Pa | PRESSURE | pressure of 100 MPa |
| RPM | ROTATION SPEED | at 200 RPM |
| ... | ... | ... |

(b) CHARACTERISTIC VALUE DICTIONARY

| CHARACTERISTIC VALUE WORD |
|---|
| S/cm |
| cm²/V |
| eV |
| ... |

FIG. 4

(a) FIRST RELEVANCE DICTIONARY

| TREATMENT WORD | STARTING/TARGET MATERIAL |
|---|---|
| mix | STARTING MATERIAL |
| dissolve | STARTING MATERIAL |
| add | STARTING MATERIAL |
| press | TARGET MATERIAL |
| ground | TARGET MATERIAL |
| ... | ... |

(b) SECOND RELEVANCE DICTIONARY

| TREATMENT WORD | ATTRIBUTE 1 OF SYNTHESIS CONDITION | ATTRIBUTE 2 OF SYNTHESIS CONDITION | ... |
|---|---|---|---|
| heat | TEMPERATURE | TIME | ... |
| anneal | TEMPERATURE | TIME | ... |
| mix | TIME | ROTATION SPEED | ... |
| dry | TIME | AIR | ... |
| press | TEMPERATURE | PRESSURE | ... |
| ... | ... | ... | ... |

FIG. 5

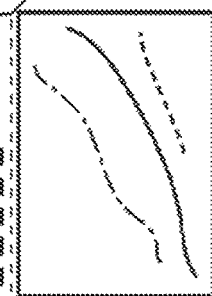

EXTRACTION-TARGET REGION

1. The $Li_{1.1}Mg_{0.6}Ti_{1.9}(PO_4)_3$ was prepared from stoichiometric mixtures of $Li_2CO_3$, MgO (99.999 %) and $TiO_2$, $NH_4H_2PO_4$ by solid state reaction.
2. The mixture was heated for 20 h at 334 K, then milled for 6 h.
3. Obtained powder was heated for 12 h at 660 K.
4. After heating, the powder was milled in a planetary mill for 7 h.
5. The millings were carried out in ethanol.
6. The final powder was dried at 293 K for 48 h.
7. The average size of the powder grain was found to be TO 1 m.
8. The powder was uniaxially cold pressed at 200 MPa, and then sintered into the ceramic samples at 936 K.
9. The sintering was conducted in air for 0.2, 0.5, 1 and 3 h.
10. The ionic conductivity of final sample is 0.00013 S/cm.

DOCUMENT

Synthesis and structure of XYZ

Abstract

1. Introduction    3. Experiment

2. Method

| MATERIAL WORD | STARTING/TARGET MATERIAL |
|---|---|
| $Li_2CO_3$ | STARTING MATERIAL |
| $MgO$ | STARTING MATERIAL |
| $TiO_2$ | STARTING MATERIAL |
| $NH_4H_2PO_4$ | STARTING MATERIAL |
| $Li_{1.1}Mg_{0.6}Ti_{1.9}(PO_4)_3$ | TARGET MATERIAL |

(b)

| TREATMENT WORD | ATTRIBUTE |
|---|---|
| mixture | MIXING TREATMENT |
| heating | HEAT TREATMENT |
| milled | MILLING TREATMENT |
| dried | DRYING TREATMENT |
| pressed | PRESSURIZATION TREATMENT |
| sintered | SINTERING TREATMENT |

(c)

| SYNTHESIS CONDITION | ATTRIBUTE |
|---|---|
| 20 h | TIME |
| 773 K | TEMPERATURE |
| 5 h | TIME |
| 1223 K | TEMPERATURE |
| 8 h | TIME |
| 393 K | TEMPERATURE |
| 300 MPa | PRESSURE |
| 3 h | TIME |

(d)

| CHARACTERISTIC VALUE |
|---|
| $1.30 \times 10^{-4}$ S/cm |

FIG. 8

(a) WORD ID
WORD NAME   ATTRIBUTE

W1 Li$_2$CO$_3$ STARTING MATERIAL
W2 MgO STARTING MATERIAL
W3 TiO$_2$ STARTING MATERIAL
W4 NH$_4$H$_2$PO$_4$ STARTING MATERIAL
W5 mix MIXING TREATMENT
W6 20 h TIME
W7 773 K TEMPERATURE
W8 heat HEAT TREATMENT
W9 5 h TIME
W10 1223 K TEMPERATURE
W11 mill MILLING TREATMENT
W12 8 h TIME
W13 dry DRYING TREATMENT
W14 393 K TEMPERATURE
W15 press PRESSURIZATION TREATMENT
W16 300 MPa PRESSURE
W17 sinter SINTERING TREATMENT
W18 3 h TIME
W19 Li$_{1.1}$Mg$_{0.6}$Ti$_{1.9}$(PO$_4$)$_3$ TARGET MATERIAL (b) RELATIONSHIP ID
RELATIONSHIP INFORMATION R1 W1:W5
R2 W2:W5
R3 W3:W5
R4 W4:W5
R5 W6:W5
R6 W7:W5
R7 W5:W8
R8 W9:W8
R9 W10:W8
R10 W8:W11
R11 W12:W11
R12 W11:W13
R13 W14:W13
R14 W13:W15
R15 W16:W15
R16 W15:W17
R17 W18:W17
R18 W17:W19
R19 W19:V (c) CHARACTERISTIC VALUE ID
CHARACTERISTIC VALUE V1 1.30×10$^{-4}$ S/cm

FIG. 15

| PAPER ID | heat(h) | heat(K) | press(Mpa) | CHARACTERISTIC VALUE (S/cm) |
|---|---|---|---|---|
| 0001 | 5 | 1223 | 300 | $1.30 \times 10^{-4}$ |
| 0029 | 7 | 1200 | 250 | $1.32 \times 10^{-4}$ |
| 0105 | 4 | 1800 | 320 | $1.31 \times 10^{-4}$ |
| 0256 | 5 | 900 | 300 | $1.35 \times 10^{-4}$ |
| COMPOSITE | 4-7 | 900-1800 | 250-320 | $1.30 \times 10^{-4} - 1.35 \times 10^{-4}$ |

FIG. 19

| PAPER ID | heat(h) | heat(K) | press(Mpa) | CHARACTERISTIC VALUE (S/cm) |
|---|---|---|---|---|
| 0001 | 5 | 1223 | 300 | $1.30 \times 10^{-4}$ |
| 0029 | 7 | 1200 | 250 | $1.32 \times 10^{-4}$ |
| 0105 | 4 | 1800 | 320 | $1.31 \times 10^{-4}$ |
| 0256 | 5 | 900 | 300 | $1.35 \times 10^{-4}$ |
| 0424 | 5 | 1000 | 450 | $1.41 \times 10^{-4}$ |
| 0785 | 6 | 1200 | 460 | $1.42 \times 10^{-4}$ |
| COMPOSITE | 4-7 | 900-1800 | 250-320 / 450-460 | $1.30 \times 10^{-4} \sim 1.35 \times 10^{-4}$ / $1.41 \times 10^{-4} \sim 1.42 \times 10^{-4}$ |

FIG. 22

| PAPER ID | heat(h) | heat(K) |
|---|---|---|
| 0001 | 5 | 1223 |
| 0142 | 7 | 1200 |
| COMPOSITE | 5-7 | 1200-1223 |

FIG. 31

| MANUFACTURER NAME | MODEL NUMBER | PERFORMANCE VALUE (MPa) | PRICE (¥) |
|---|---|---|---|
| A Company | AS-0122 | 260-300 | 500,000 |
| B Company | YP-0134 | 200-350 | 800,000 |
| C Company | TG-141 | 200-250 | 300,000 |
| D Company | PA-221 | 280-350 | 600,000 |

FIG. 34

```
@article{ABC2012,
title = "The synthesis process of cubic garnet solid electrolyte of Li6La4Zr2O12",
journal = "Solid State Ionics",
volume = "106",
pages = "29 - 35",
year = "2012",
issn = "1111 -2222",
doi = "https://doi.org/10.1019/j.ssi.2013.11.023",
url = "http://www.sciencejournal.com/article/0123456789",
author = {E. Nakashima, T. Tanaka, K. Sakamoto},
Affiliation={Tokyo Chemical Laboratory}
keywords = "Ionic conductivity, Hot-pressing"
}
```

FIG. 35

(a) TG/DTA (TN-2000, Korea Chem Inc.) thermal analyses of the LTO powders with different lithium sources was carried out at temperature up to 1200 °C. The powder X-ray diffraction data were measured at 298 K using an X-ray diffractometer (XRD, Gaku Mini II, Japan Chem Inc.).

(b) Octylamine (99 %) was purchased from China Industry. Acetone (99.5%) and methanol (99.5%) were obtained from Sako Pure Chemicals Co., Ltd. All chemicals were used as purchased without further purification.

FIG. 36

Acknowledgements
This work is financially supported by the Fundamental Research Funds for the North Universities, the National Material Science Foundation of Japan (No. 11112222 and 33334444), the Specialized Research Fund for the Doctoral Program of Higher Education of Japan (No. ABC111).

| APPARATUS ID | APPARATUS NAME | APPARATUS ANOTHER NAME | APPARATUS MODEL NUMBER | VENDOR NAME | RELATED APPARATUS ID | PRICE (¥) | USAGE STARTING MONTH | SPECIFICATIONS |
|---|---|---|---|---|---|---|---|---|
| 1 | Ball Miling Machine | BM | BZ204B | Osaka Industries. | [3, 4] | 80,000 | JULY 2011 | ... |
| 2 | Simple XRD | None | SH220C | Tokyo Chemical Industries. | [6] | 1,200,000 | MAY 2012 | ... |
| 3 | Ball Miling Ultra | BM U | IO990B | ABC Chemical. | [1, 2] | 980,00 | AUGUST 2018 | ... |
| 4 | Ball Miling Super | BM S | GG556L | XYZ Industries. | [5] | 1,200,000 | JULY 2011 | ... |
| ... | ... | ... | ... | ... | ... | ... | ... | ... |

| MATERIAL ID | MATERIAL NAME | MATERIAL ANOTHER NAME | VENDOR NAME | PRICE (¥)/g |
|---|---|---|---|---|
| 1 | $GeO_2$ | None | ABC Chemical | 2000 |
| 2 | $NH_4H_2PO_4$ | None | ABC Chemical | 4000 |
| 3 | LiPON | Lithium phosphorus oxynitride | Nakamura Material | 1500 |
| 4 | LiPON | Lithium phosphorus oxynitride | Nakamura Material | 2000 |
| ... | ... | ... | ... | ... |

| PROJECT ID | PROJECT NAME | PROJECT ANOTHER NAME | PROJECT IDENTIFICATION NUMBER | STARTING YEAR | ENDING YEAR | BUDGET AMOUNT |
|---|---|---|---|---|---|---|
| 1 | Fund of material research | MAT | 234-3344 | 2018 | 2020 | ¥20,000,000 |
| 2 | Development of all solid state battery | ASSB | No.1234 | 2019 | 2024 | ¥50,000,000 |
| 3 | Development of solar cell unit | SCU | 119-0099 | 2020 | 2021 | ¥5,000,000 |
| ... | ... | ... | ... | ... | ... | ... |

FIG. 41

| UNIT SYMBOL | NUMERICAL NOTATION |
|---|---|
| g | 1 |
| mg | 0.001 |
| μg | 0.000001 |
| ... | ... |

| ORGANIZATION ID | ORGANIZATION NAME |
|---|---|
| 1 | A UNIVERSITY |
| 2 | B UNIVERSITY |
| 3 | C CORPORATION |
| ... | ... |

(b) T2

| AUTHOR ID | AUTHOR NAME |
|---|---|
| 1 | K. Sasaki |
| 2 | E. Kim |
| 3 | G. Bai |
| ... | ... |

| PAPER ID | AUTHOR LIST | ORGANIZATION LIST | APPARATUS-RELATED INFORMATION | PROJECT-RELATED INFORMATION | MATERIAL-RELATED INFORMATION | PUBLICATION MONTH |
|---|---|---|---|---|---|---|
| 1 | [1,2] | [1] | {(1:2,000,000), (2:90,000)} | {(2:20,000,000), (3:90,000,000)} | {2:0.1} | JUNE 2019 |
| 2 | [2,3] | [2] | {(3:4,000,000), (5:12,000,000)} | {(3:4,000,000), (5:12,000,000)} | {3:0.5} | DECEMBER 2018 |
| 3 | [3] | [2,3] | {(2:4,000,000), (4:8,000,000), (6:4,000,000)} | {(2:4,000,000), (4:8,000,000), (6:4,000,000)} | {1:0.1, 2:0.4, 3:0.2} | JULY 2019 |
| ... | ... | ... | ... | ... | ... | ... |

| PAPER ID | AUTHOR LIST | ORGANIZATION LIST | APPARATUS-RELATED INFORMATION | PROJECT-RELATED INFORMATION | PUBLICATION MONTH |
|---|---|---|---|---|---|
| 1 | [1, 2] | [1] | {(1:2,000,000), (2:90,000)} | {(2:20,000,000), (3:90,000,000)} | JUNE 2019 |
| 2 | [2, 3] | [2] | {(3:4,000,000), (5:12,000,000)} | {(3:4,000,000), (5:12,000,000)} | DECEMBER 2018 |
| 3 | [3] | [2, 3] | {(2:4,000,000), (4:8,000,000), (6:4,000,000)} | {(2:4,000,000), (4:8,000,000), (6:4,000,000)} | JULY 2019 |
| ... | ... | ... | ... | ... | ... |

| PAPER ID | AUTHOR LIST | ORGANIZATION LIST | PROJECT-RELATED INFORMATION | MATERIAL-RELATED INFORMATION | PUBLICATION MONTH |
|---|---|---|---|---|---|
| 1 | [1,2] | [1] | {(2:20,000,000), (3:90,000,000)} | {2:0.1} | JUNE 2019 |
| 2 | [2,3] | [2] | {(3:4,000,000), (5:12,000,000)} | {3:0.5} | DECEMBER 2018 |
| 3 | [3] | [2,3] | {(2:4,000,000), (4:8,000,000), (6:4,000,000)} | {1:0.1, 2:0.4, 3:0.2} | JULY 2019 |
| ... | ... | ... | ... | ... | ... |

| ORGANIZATION ID | APPARATUS-RELATED INFORMATION | PROJECT-RELATED INFORMATION | MATERIAL-RELATED INFORMATION | PAPER AUTHOR INFORMATION |
|---|---|---|---|---|
| 1 | {(1:2,000,000),(2:90,000)} | {(2:20,000,000),(3:90,000,000)} | {2:0.1} | {1:[1,2]} |
| 2 | {(2:400,000),(3:4,000,000),(4:8,000,000),(5:12,000,000),(6:400,000)} | {(2:400,000),(3:4,000,000),(4:8,000,000),(5:12,000,000),(6:400,000)} | {1:0.1, 2:0.4, 3:0.7} | {2:[2,3],3:[3]} |
| 3 | {(2:4,000,000),(4:8,000,000),(6:4,000,000)} | {(2:4,000,000),(4:8,000,000),(6:4,000,000)} | {1:0.1, 2:0.4, 3:0.2} | {3:[3]} |
| ... | ... | ... | ... | ... |

FIG. 45A

| EXTRACTED INFORMATION | | MATERIAL ESTIMATION INFORMATION | | |
|---|---|---|---|---|
| ORGANIZATION ID | MATERIAL ID | PURCHASE PROBABILITY | SOLVENCY | PROFIT RATIO |
| 1 | 2 | HIGH | MEDIUM | HIGH |
| 2 | 1 | MEDIUM | LOW | LOW |
| ⋮ | ⋮ | ⋮ | ⋮ | ⋮ |

FIG. 45B

| EXTRACTED INFORMATION | | MATERIAL ESTIMATION INFORMATION | | | |
|---|---|---|---|---|---|
| ORGANIZATION ID | MATERIAL ID | PURCHASE PROBABILITY | WEB-SEARCH-REFLECTED PROBABILITY | SOLVENCY | PROFIT RATIO |
| 1 | 2 | HIGH | MEDIUM | MEDIUM | HIGH |
| 2 | 1 | MEDIUM | HIGH | LOW | LOW |
| ⋮ | ⋮ | ⋮ | ⋮ | ⋮ | ⋮ |

FIG. 48

| EXTRACTED INFORMATION | | | APPARATUS ESTIMATION INFORMATION | |
|---|---|---|---|---|
| ORGANIZATION ID | APPARATUS ID | RELATED APPARATUS ID | PURCHASE PROBABILITY | SOLVENCY |
| 1 | 1 | 2 | HIGH | LOW |
| 2 | 2 | 3 | MEDIUM | HIGH |
| ⋮ | ⋮ | ⋮ | ⋮ | ⋮ |

SUPPORT APPARATUS, GENERATION APPARATUS, ANALYSIS APPARATUS, SUPPORT METHOD, GENERATION METHOD, ANALYSIS METHOD, AND NON-TRANSITORY COMPUTER-READABLE RECORDING MEDIUM

BACKGROUND

1. Technical Field

The present disclosure relates to a support apparatus that supports a search for a synthesis process, and so forth.

2. Description of the Related Art

A system for supporting a search for a synthesis process has been proposed (see, for example, Japanese Unexamined Patent Application Publications No. 2010-9257 and No. 11-53425, hereinafter referred to as JP '257 and JP '425, respectively). The system disclosed in JP '257 automatically ranks and narrows down synthesis routes corresponding to synthesis processes given for a target compound to be synthesized, and proposes the result. The system disclosed in JP '425 predicts many synthesis routes corresponding to synthesis processes, and displays an economically and industrially realizable synthesis route among the predicted synthesis routes.

SUMMARY

However, the systems disclosed in JP '257 and JP '425 are susceptible to further improvement.

One non-limiting and exemplary embodiment provides a support apparatus capable of achieving further improvement, and so forth.

In one general aspect, the techniques disclosed here feature a support apparatus including a generation apparatus and an analysis apparatus. The generation apparatus executes (a-1) to (a-5) with i=1 to n, and generates process information 1 to process information n which are pieces of process information. The i is a natural number. The n is a natural number greater than or equal to 2. In the (a-1), a material word extractor included in the generation apparatus extracts material words from a document i, the material words including starting material words indicating starting materials and a target material word indicating a target material. In the (a-2), a treatment word extractor included in the generation apparatus extracts a treatment word i from the document i, the treatment word i indicating a treatment i of generating the target material from the starting materials. In the (a-3), a condition extractor included in the generation apparatus extracts a synthesis condition i from the document i, the synthesis condition i being a condition i of the treatment i. In the (a-4), a characteristic value extractor included in the generation apparatus extracts a characteristic value i related to the target material from the document i. In the (a-5), a generator included in the generation apparatus associates the material words, the treatment word i, the synthesis condition i, and the characteristic value i with each other to generate process information i indicating a procedure i of generating the target material from the starting materials. The analysis apparatus includes a combiner that generates composite process information including a common part common to the pieces of process information and different parts different among the pieces of process information, and an outputter that outputs the composite process information.

It should be noted that general or specific embodiments may be implemented as an apparatus, a system, a method, an integrated circuit, a computer program, a computer-readable recording medium such as a compact disc-read only memory (CD-ROM), or any selective combination thereof.

The support apparatus in the present disclosure is able to achieve further improvement. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1 is a diagram illustrating an example of a hardware configuration of a synthesis process search support system in a first embodiment;

FIG. 2 is a block diagram illustrating an example of a functional configuration of the synthesis process search support system in the first embodiment;

FIG. 3A is a diagram illustrating dictionaries respectively used in a material word extraction unit and a treatment word extraction unit in the first embodiment:

FIG. 3B is a diagram illustrating dictionaries respectively used in a condition extraction unit and a characteristic value extraction unit in the first embodiment;

FIG. 4 is a diagram illustrating dictionaries used in a generation unit in the first embodiment;

FIG. 5 is a diagram illustrating an example of documents accumulated in a document accumulation unit of a synthesis process generation apparatus in the first embodiment;

FIG. 7 is a diagram illustrating an example of material words, treatment words, synthesis conditions, and a characteristic value that have been extracted in the first embodiment;

FIG. 8 is a diagram illustrating an example of a synthesis process generated as structured data in the first embodiment;

FIG. 15 is a diagram for describing processing performed by a combining unit in the first embodiment;

FIG. 19 is a diagram for describing processing performed by the combining unit according to a second modification of the first embodiment;

FIG. 22 is a diagram for describing processing performed by the combining unit according to the third modification of the first embodiment;

FIG. 31 is a diagram illustrating an example of facility information in the third embodiment;

FIG. 34 is a diagram illustrating an example of contents of a paper bib in the fourth embodiment;

FIG. 35 is a diagram illustrating an example of contents of a paper PDF in the fourth embodiment;

FIG. 36 is a diagram illustrating an example of other contents of the paper PDF in the fourth embodiment;

FIG. 38 is a diagram illustrating an example of a data table held in an apparatus database in the fourth embodiment;

FIG. 39 is a diagram illustrating an example of a data table held in a material database in the fourth embodiment;

FIG. 40 is a diagram illustrating an example of a data table held in a project database in the fourth embodiment;

FIG. 41 is a diagram illustrating an example of a data table held in a unit dictionary database in the fourth embodiment;

FIG. 42 is a diagram illustrating an example of an organization identification table and an author identification table in the fourth embodiment;

FIG. 43A is a diagram illustrating an example of a data table stored in a customer database in the fourth embodiment;

FIG. 43B is a diagram illustrating another example of a data table stored in the customer database in the fourth embodiment;

FIG. 43C is a diagram illustrating another example of a data table stored in the customer database in the fourth embodiment;

FIG. 44 is a diagram illustrating an example of an organization data table in the fourth embodiment;

FIG. 45A is a diagram illustrating an example of an estimation result regarding materials obtained by an estimation unit in the fourth embodiment;

FIG. 45B is a diagram illustrating another example of an estimation result regarding materials obtained by the estimation unit in the fourth embodiment;

FIG. 48 is a diagram illustrating an example of an estimation result regarding apparatuses obtained by the estimation unit in the fourth embodiment;

DETAILED DESCRIPTION

Figure 6:
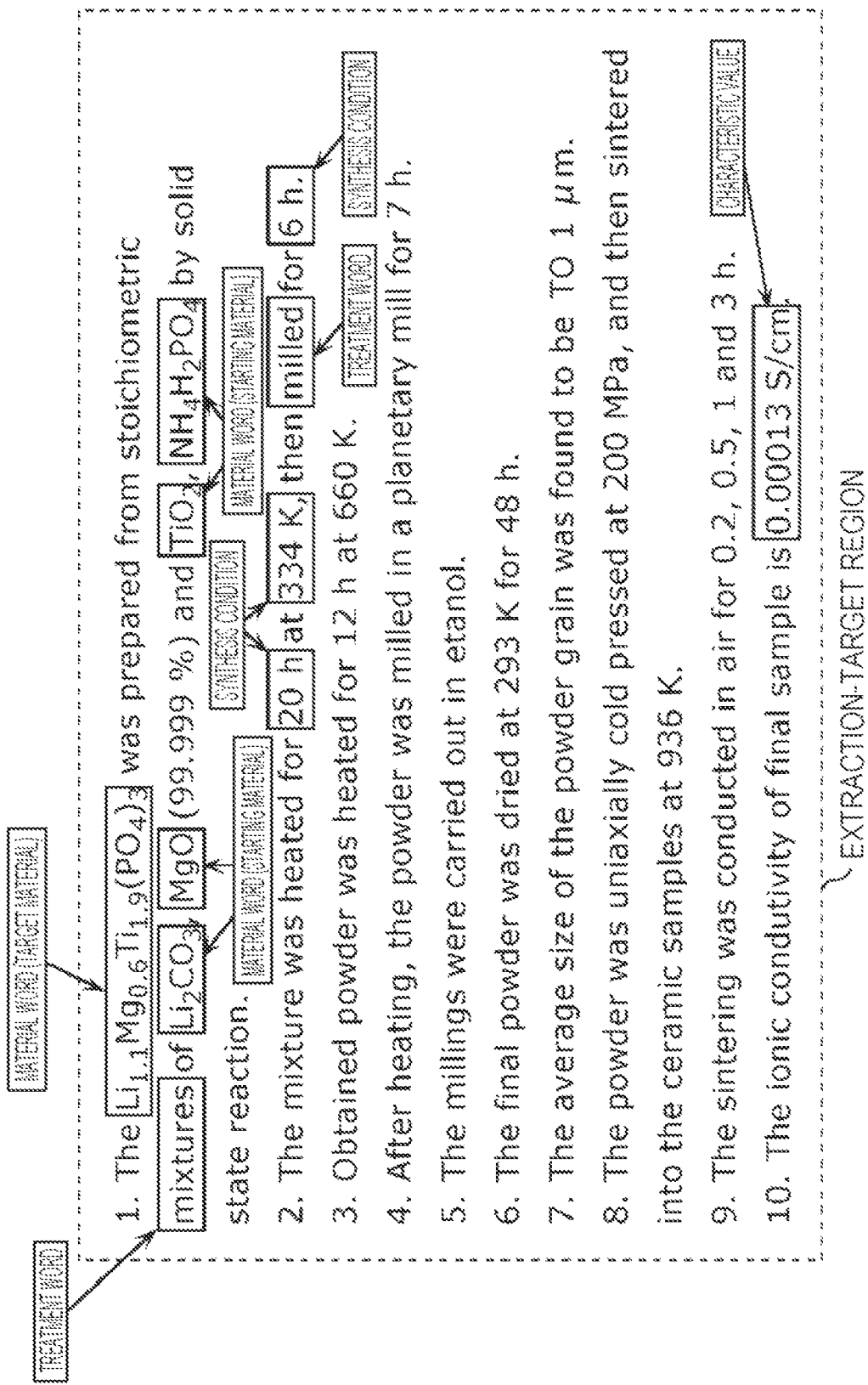
FIG. 6 is a diagram illustrating an example of words, synthesis conditions, and a characteristic value extracted from an extraction-target region of a document in the first embodiment.

Underlying Knowledge Forming Basis of the Present Invention

To create a new material (also referred to as a new compound), a synthesis process is to be found out from among an enormous number of combinations of experimental conditions. Under present circumstances, a search for a synthesis process relies on the knowledge and experience of researchers. However, it takes a lot of time and cost to find an optimum synthesis process from among an enormous number of experimental conditions, and it is not easy even for an experienced researcher to find a synthesis process of a new compound. For this reason, attempts have been made to reduce the cost of developing new materials by leaving a search for a synthesis process to a computer. A search for a synthesis process by a computer is performed by analyzing relationships among material names, experimental procedures, and experimental conditions accumulated in a known database.

Regarding the analysis of a synthesis process described above, for example, JP '257 mentioned above discloses a synthesis route evaluation system including arithmetic processing means including a quantum chemistry calculation unit, a reaction mechanism analysis unit, and a synthesis route ranking unit; and storage means for storing data related to a synthesis route. This synthesis route evaluation system extracts an optimum synthesis route from among synthesis routes for a target compound to be synthesized.

JP '425 mentioned above discloses a synthesis route design system including means for predicting routes (i.e., synthesis routes) of synthesizing target molecules from a commercially available compound by applying a reaction rule accumulated in a reaction knowledge base, means for estimating, for each of the predicted synthesis routes, a variable cost index as a measure of a cost required for producing target molecules from a starting material, and means for presenting the predicted synthesis routes to a user in ascending order of the estimated variable cost index. In this synthesis route design system, a user is able to easily determine which synthesis route is economically and industrially realizable among a large number of predicted synthesis routes.

However, the systems disclosed in the above-mentioned-Patent Documents JP '257 and JP '425 documents, that is, the systems that support a search for a synthesis process, are susceptible to further improvement.

A synthesis process of interest is often described in a natural language in a document, such as a paper, and the systems disclosed in the JP '257 and JP '425 documents mentioned above do not enable easy use of the synthesis process described in the document. More specifically, many papers are published every year in the field of materials, and the latest synthesis processes are described in these papers. However, the systems disclosed in the JP '257 and JP '425 documents mentioned above do not enable easy use of the latest synthesis processes, and are thus incapable of appropriately supporting a search for a synthesis process.

To address the foregoing issues, a support apparatus according to an aspect of the present disclosure includes a generation apparatus and an analysis apparatus. The generation apparatus executes (a-1) to (a-5) with i=1 to n, and generates process information 1 to process information n which are pieces of process information. The i is a natural number. The n is a natural number greater than or equal to 2. In the (a-1), a material word extractor included in the generation apparatus extracts material words from a document i, the material words including starting material words indicating starting materials and a target material word indicating a target material. In the (a-2), a treatment word extractor included in the generation apparatus extracts a treatment word i from the document i, the treatment word i indicating a treatment i of generating the target material from the starting materials. In the (a-3), a condition extractor included in the generation apparatus extracts a synthesis condition i from the document i, the synthesis condition i being a condition i of the treatment i. In the (a-4), a characteristic value extractor included in the generation apparatus extracts a characteristic value i related to the target material from the document i. In the (a-5), a generator included in the generation apparatus associates the material words, the treatment word i, the synthesis condition i, and the characteristic value i with each other to generate process information i indicating a procedure i of generating the target material from the starting materials. The analysis apparatus includes a combiner that generates composite process information including a common part common to the pieces of process information and different parts different among the pieces of process information, and an outputter that outputs the composite process information. For example, the treatment word extractor may extract the treatment word i indicating at least one of a heat treatment, a mixing treatment, a drying treatment, or a dissolution treatment. The condition extractor may extract, as the synthesis condition i, at least one of a temperature, a time, a pressure, or a rotation speed each of which is indicated by a numerical value and a unit. Each of the process information i and the composite process information may also be referred to as information indicating a synthesis process which is a process of synthesizing a target material from starting materials.

Accordingly, the pieces of process information can be easily generated from a document 1 to a document n. The composite process information is generated from the pieces of generated process information and is output. Thus, when the composite process information is displayed, the common part and the different parts of the many pieces of process information can be displayed in an easy-to-understand manner. Accordingly, a search for a synthesis process for a new material can be appropriately supported.

In a case where pieces of process information respectively generated from the latest documents i are combined to generate composite process information, the knowledge about material development can be kept up-to-date. In addition, by using an enormous number of documents, a search for a synthesis process covering a wide range of materials can be supported.

In a case where a synthesis condition 1 to a synthesis condition n different from each other and associated with the treatment word i common to the pieces of process information are the different parts, the combiner may generate a comprehensive synthesis condition including the synthesis condition 1 to the synthesis condition n different from each other, and may replace the synthesis condition i included in the process information i and associated with the common treatment word i with the comprehensive synthesis condition to generate the composite process information. For example, in a case where the synthesis condition 1 to the synthesis condition n different from each other indicate a numerical value 1 to a numerical value n different from each other, respectively, in generation of the comprehensive synthesis condition, the combiner may generate, as the comprehensive synthesis condition, a numerical value range defined by a minimum value and a maximum value among the numerical value 1 to the numerical value n different from each other. In other words, in a case where treatment words among a treatment word 1 to a treatment word n are identical, the combiner may generate, from a synthesis condition 1 to a synthesis condition n, a comprehensive synthesis condition including synthesis conditions corresponding to the treatment words, and may replace the synthesis conditions with the comprehensive synthesis condition to generate the composite process information. In a case where the synthesis condition 1 to the synthesis condition n different from each other indicate a numerical value 1 to a numerical value n, respectively, a minimum numerical value among the numerical value 1 to the numerical value n is a numerical value p, a maximum numerical value among the numerical value 1 to the numerical value n is a numerical value q, and the numerical value p and the numerical value q satisfy $1 \leq p \leq n$, $1 \leq q \leq n$, and $p \neq q$, the comprehensive synthesis condition may indicate a range from the numerical value p to the numerical value q.

Accordingly, the synthesis condition 1 to the synthesis condition n used in the document 1 to the document n are collectively displayed as the comprehensive synthesis condition, and thus a synthesis process for a new material can be easily searched for by viewing the comprehensive synthesis condition.

In a case where the synthesis condition 1 to the synthesis condition n different from each other indicate a numerical value 1 to a numerical value n different from each other, respectively, in generation of the comprehensive synthesis condition, the combiner may perform clustering on a set including the numerical value 1 to the numerical value n different from each other to generate subsets, and may generate the comprehensive synthesis condition from each of the subsets.

Accordingly, comprehensive synthesis conditions are generated by clustering, and thus the tendency of the synthesis condition 1 to the synthesis condition n used in the document 1 to the document n can be grasped in more detail.

In the (a-2), the treatment word extractor may extract at least one treatment word i including the treatment word i from the document i. In the (a-3), the condition extractor may extract at least one synthesis condition i including the synthesis condition i from the document i. In generation of the composite process information, the combiner may associate the different parts with the common part such that a flow of generating a material branches from the common part to the different parts, to generate the composite process information.

Accordingly, in a case where the pieces of process information include a common treatment word and different treatment words, composite process information is generated such that a flow of treatments branches from the treatment indicated by the common treatment word to the treatments indicated by the different treatment words. Accordingly, even if the pieces of process information include treatment words different from each other, a common treatment and different treatments can be displayed in an easy-to-understand manner.

In a case where the common part includes a common target material word common to the pieces of process information and the different parts include a characteristic value 1 to a characteristic value n different from each other among the pieces of process information, in generation of the composite process information, the combiner may further generate a comprehensive characteristic value including the characteristic value 1 to the characteristic value n different from each other, and may replace the characteristic value i included in the process information i with the comprehensive characteristic value.

Accordingly, even if the synthesis conditions 1 to n used in the documents 1 to n are different and thus the characteristic values 1 to n of the target material are different, these characteristic values 1 to n are collectively displayed as a comprehensive characteristic value, and thus a synthesis process for a new material can be easily searched for by viewing the comprehensive characteristic value.

The analysis apparatus may further include a synthesis condition acceptor that accepts an input synthesis condition which is a condition of a treatment, and a characteristic value estimator that estimates a characteristic value of a target material indicated by the common target material word, the characteristic value being based on the input synthesis condition. The outputter may further output the characteristic value estimated by the characteristic value estimator. The characteristic value estimator may estimate the characteristic value that is based on the input synthesis condition, in accordance with a relationship between the synthesis condition i included in each of the pieces of process information and the characteristic value i included in each of the pieces of process information.

Accordingly, a characteristic value of a target material is estimated and displayed in response to a user's setting of an input synthesis condition. Thus, for example, a synthesis process for a material having a new characteristic value can be easily searched for.

In generation of the pieces of process information, the generation apparatus may execute the (a-1) to the (a-5) with i=1 to m, and may generate process information 1 to process information m. The m may be a natural number greater than or equal to the n. The analysis apparatus may further include a searcher that searches the process information 1 to the process information m generated by the generation apparatus for the process information 1 to the process information n. The searcher may search for the process information 1 to the process information n by using at least one of the treatment word i, the synthesis condition i, the characteristic value i, or a set of the material words.

Accordingly, the composite process information can be generated by searching for the process information 1 to the process information n to which at least one of the treatment word, the synthesis condition, the characteristic value, or a set of the material words is common.

In the (a-5), the generator may add bibliographic information of the document i to the generated process information i. The searcher may search for the process information 1 to the process information n by further using the bibliographic information. For example, the bibliographic information may indicate at least one of a name of an author of the document i, a publication date of the document i, a name of an organization to which the author belongs, or the number of citations of the document i.

Accordingly, the composite process information can be generated by searching for the process information 1 to the process information n to which a publication period or the like included in the bibliographic information is common.

The analysis apparatus may further include a facility searcher that performs a search for a facility capable of performing a treatment under the comprehensive synthesis condition generated by the combiner, by referring to, for each of facilities, facility information indicating a list of treatment conditions satisfiable by the facility. The outputter may further output information about the facility found through the search performed by the facility searcher.

Accordingly, a user can be easily notified of a facility capable of performing a treatment under the comprehensive synthesis condition. As a result, a facility required for synthesizing a material can be easily arranged.

The pieces of process information generated by the generator and the composite process information generated by the combiner may each be configured to be graphable. The outputter may display the composite process information generated by the combiner in a graph format.

Accordingly, because the pieces of process information are configured as graphable structured data, the composite process information can also be easily generated as graphable structured data. Furthermore, the composite process information is displayed in a graph format such as a flowchart, and thus the user can appropriately grasp the composite process information.

In a case where a target material word in first process information and a starting material word in second process information among the pieces of process information are identical material words and correspond to a common part common to the pieces of process information, the composite process information generated by the combiner may indicate a procedure of synthesizing, from starting materials indicated by the first process information, an intermediate material which is a material indicated by the identical material words corresponding to the common part, and generating a target material indicated by the second process information from the intermediate material.

Accordingly, the composite process information indicating a procedure that is not described in any of the document 1 to the document n can be generated. Thus, when such composite process information is displayed, a search for a new synthesis process can further be supported.

The support apparatus may further include an analyzer. The analyzer may execute (b-1) to (b-3) with i=1 to n, and may generate a data set 1 to a data set n which are data sets. In the (b-1), the analyzer may extract author-related information i from the document i, the author-related information i being information about at least one of an author of the document i or an organization to which the author belongs. In the (b-2), the analyzer may extract apparatus-related information i from the document i, the apparatus-related information i being information about an apparatus. In the (b-3), the analyzer may generate a data set i indicating the author-related information i and the apparatus-related information i in association with each other.

Accordingly, the data set 1 to the data set n are generated from the document 1 to the document n. The data set i indicates the author-related information i and the apparatus-related information i of the document i in association with each other. Thus, which author or organization uses which apparatus can be easily grasped by viewing the data set 1 to the data set n. Thus, the efficiency of business activities by apparatus vendors can be enhanced.

The analyzer may further execute (b-4) with i=1 to n in generation of the data sets. In the (b-4), the analyzer may extract material information i from the document i, the material information i being information about a type of a material. In the (b-3), the analyzer may generate the data set i further indicating the material information i in association with the author-related information i.

Accordingly, the data set i indicates the author-related information i and the material information i of the document i in association with each other. Thus, which author or organization uses which material can be easily grasped by viewing the data set 1 to the data set n. Thus, the efficiency of business activities by material vendors can be enhanced.

The analyzer may further execute (b-5) with i=1 to n in generation of the data sets. In the (b-5), the analyzer may extract amount information i from the document i, the amount information i being information about an amount of the material. In the (b-3), the analyzer may generate the data set i further indicating the amount information i in association with the author-related information i.

Accordingly, the data set i indicates the author-related information i, the material information i, and the amount information i of the document i in association with each other. Thus, which author or organization uses which amount of which material can be easily grasped by viewing the data set 1 to the data set n. Thus, the efficiency of business activities by material vendors can further be enhanced.

The analyzer may further execute (b-6) with i=1 to n in generation of the data sets. In the (b-6), the analyzer may extract project-related information i from the document i, the project-related information i being information about a project of supporting the author or the organization. In the (b-3), the analyzer may generate the data set i further indicating the project-related information i in association with the author-related information i.

Accordingly, the data set i indicates the author-related information i and the project-related information of the document i in association with each other. Thus, which author or organization is supported by which project can be easily grasped by viewing the data set 1 to the data set n. Thus, the solvency of the author or organization can be estimated, and the efficiency of business activities for the author or organization can further be enhanced.

A generation apparatus according to an aspect of the present disclosure includes a material word extractor, a treatment word extractor, a condition extractor, a characteristic value extractor, and a generator. The generation apparatus executes (a-1) to (a-5) with i=1 to n, and generates process information 1 to process information n which are pieces of process information. The i is a natural number. The n is a natural number greater than or equal to 2. In the (a-1), the material word extractor extracts material words from a document i, the material words including starting material words indicating starting materials and a target material word indicating a target material. In the (a-2), the treatment word extractor extracts a treatment word i from the document i, the treatment word i indicating a treatment i of generating the target material from the starting materials. In the (a-3), the condition extractor extracts a synthesis condition i from the document i, the synthesis condition i being a condition i of the treatment i. In the (a-4), the characteristic value extractor extracts a characteristic value i related to the target material from the document i. In the (a-5), the generator associates the material words, the treatment word i, the synthesis condition i, and the characteristic value i with each other to generate process information i indicating a procedure i of generating the target material from the starting materials.

Accordingly, the pieces of process information can be easily generated from a document 1 to a document n. For example, process information which is graphable structured data can be easily generated from a synthesis process described in a natural language in a document. Thus, the synthesis process described in the document can be presented to a user in an easy-to-understand manner.

An analysis apparatus according to an aspect of the present disclosure includes a combiner that generates composite process information including a common part common to pieces of process information and different parts different among the pieces of process information, and an outputter that outputs the composite process information. Each of the pieces of process information is information indicating a procedure of generating a target material from starting materials, and indicates material words including starting material words indicating the starting materials and a target material word indicating the target material, a treatment word indicating a treatment of generating the target material from the starting materials, a synthesis condition which is a condition of the treatment, and a characteristic value of the target material in association with each other.

Accordingly, the composite process information is generated from the pieces of generated process information and is output. Thus, when the composite process information is displayed, the common part and the different parts of the many pieces of process information can be displayed in an easy-to-understand manner. Accordingly, a search for a synthesis process for a new material can be appropriately supported. Thus, with many pieces of latest process information, the knowledge about material development can be kept broad and up-to-date.

To address the foregoing issues, a synthesis process search support system according to an aspect of the present disclosure includes a synthesis process generation apparatus that generates, for each of the documents, a synthesis process which is a treatment procedure of synthesizing a target material from starting materials on the basis of a description in the document; and a synthesis process analysis apparatus that analyzes the synthesis processes generated by the synthesis process generation apparatus. The synthesis process generation apparatus includes a material word extractor that extracts material words indicating the starting materials and the target material from one extraction-target document among the documents, a treatment word extractor that extracts a treatment word indicating a treatment applied to material synthesis using the starting materials from the extraction-target document, a condition extractor that extracts a condition of the treatment as a synthesis condition from the extraction-target document, a characteristic value extractor that extracts a characteristic value of the target material from the extraction-target document, and a generator that generates the synthesis process by associating with each other the material words, the treatment word, the synthesis condition, and the characteristic value that have been extracted from the extraction-target document. The synthesis process analysis apparatus includes a combiner that combines the synthesis processes generated by the synthesis process generation apparatus to generate a composite synthesis process indicating a common part common to the synthesis processes and comprehensively indicating different parts different from each other among the synthesis processes, and a display that displays the composite synthesis process generated by the combiner. For example, the treatment word extractor may extract the treatment word indicating at least one of a heat treatment, a mixing treatment, a drying treatment, or a dissolution treatment. The condition extractor may extract, as the synthesis condition, at least one of a temperature, a time, a pressure, or a rotation speed each of which is indicated by a numerical value and a unit.

Accordingly, a synthesis process, which is a treatment procedure of synthesizing a target material from starting materials, can be easily generated from a document. A composite synthesis process is generated from generated synthesis processes. Thus, a common part and different parts of the many synthesis processes can be displayed in an easy-to-understand manner. Accordingly, a search for a synthesis process for a new material can be appropriately supported.

In a case where synthesis processes respectively generated from the latest documents are combined together, the knowledge about material development can be kept up-to-date. In addition, by using an enormous number of documents, a search for a synthesis process covering a wide range of materials can be supported.

In a case where the different parts include synthesis conditions different from each other and associated with a treatment word common to the synthesis processes, the combiner may generate a comprehensive synthesis condition comprehensively indicating the synthesis conditions different from each other, and may replace, with the comprehensive synthesis condition, a synthesis condition included in any one replace-target synthesis process among the synthesis processes and associated with the common treatment word, to generate the composite synthesis process. For example, in a case where the synthesis conditions different from each other respectively indicate numerical values different from each other, in generation of the comprehensive synthesis condition, the combiner may generate, as the comprehensive synthesis condition, a numerical value range defined by a minimum value and a maximum value among the numerical values different from each other.

Accordingly, the synthesis conditions used in individual documents are collectively displayed as a comprehensive synthesis condition, and thus a synthesis process for a new material can be easily searched for by viewing the comprehensive synthesis condition.

In a case where the synthesis conditions different from each other respectively indicate numerical values different from each other, in generation of the comprehensive synthesis condition, the combiner may perform clustering on a set including the numerical values different from each other to generate subsets, and may generate the comprehensive synthesis condition from each of the subsets.

Accordingly, comprehensive synthesis conditions are generated by clustering, and thus the tendency of synthesis conditions used in individual documents can be grasped in more detail.

In generation of the composite synthesis process, the combiner may generate the composite synthesis process by comprehensively associating the different parts with the common part such that a flow of treatments branches from the common part to the different parts.

Accordingly, in a case where synthesis processes include a common treatment word and different treatment words, a composite synthesis process is generated such that a flow of treatments branches from the treatment indicated by the common treatment word to the treatments indicated by the different treatment words. Accordingly, even if the synthesis processes include treatment words different from each other, a common treatment and different treatments can be displayed in an easy-to-understand manner.

In a case where the common part includes a common target material word common to the synthesis processes and the different parts include characteristic values different from each other among the synthesis processes, in generation of the composite synthesis process, the combiner may further generate a comprehensive characteristic value comprehensively indicating the characteristic values different from each other, and may replace the characteristic value included in the replace-target synthesis process with the comprehensive characteristic value.

Accordingly, even if the synthesis conditions used in individual documents are different and thus the characteristic values of a target material are different, these characteristic values are collectively displayed as a comprehensive characteristic value, and thus a synthesis process for a new material can be easily searched for by viewing the comprehensive characteristic value.

The synthesis process analysis apparatus may further include a synthesis condition acceptor that accepts an input synthesis condition which is a condition of a treatment, and a characteristic value estimator that estimates a characteristic value of the common target material, the characteristic value being based on the input synthesis condition. The display may further display the characteristic value estimated by the characteristic value estimator. The characteristic value estimator may estimate the characteristic value that is based on the input synthesis condition, in accordance with a relationship between the synthesis condition included in each of the synthesis processes and the characteristic value included in each of the synthesis processes.

Accordingly, a characteristic value of a target material is estimated and displayed in response to a user's setting of an input synthesis condition. Thus, for example, a synthesis process for a material having a new characteristic value can be easily searched for.

The synthesis process analysis apparatus may further include a searcher that searches N (N is an integer greater than or equal to 2) synthesis processes generated by the synthesis process generation apparatus for M (M is an integer smaller than or equal to N) synthesis processes. The combiner may combine the M synthesis processes when M is 2 or more. The searcher may search for the M synthesis processes by using at least one of the treatment word, the synthesis condition, the characteristic value, or a set of the material words.

Accordingly, it is possible to search for and combine M synthesis processes to which at least one of the treatment word, the synthesis condition, the characteristic value, or a set of the material words is common.

The generator may add, to each of the generated synthesis processes, bibliographic information of a document corresponding to the synthesis process. The searcher may search for the M synthesis processes by further using the bibliographic information. For example, the bibliographic information may indicate at least one of a name of an author of a document corresponding to the bibliographic information, a publication date of the document, a name of an organization to which the author belongs, or the number of citations of the document.

Accordingly, it is possible to search for and combine M synthesis processes to which a publication period or the like included in the bibliographic information is common.

The synthesis process analysis apparatus may further include a facility searcher that performs a search for a facility capable of performing a treatment under the comprehensive synthesis condition generated by the combiner, by referring to, for each of facilities, facility information indicating a list of treatment conditions satisfiable by the facility. The display may further display information about the facility found through the search performed by the facility searcher.

Accordingly, a user can be easily notified of a facility capable of performing a treatment under the comprehensive synthesis condition. As a result, a facility required for synthesizing a material can be easily arranged.

The synthesis processes generated by the generator and the composite synthesis process generated by the combiner may each be configured to be graphable. The display may display the composite synthesis process generated by the combiner in a graph format.

Accordingly, because the synthesis processes are configured as graphable structured data, the composite synthesis process can also be easily generated as graphable structured data. Furthermore, the composite synthesis process is displayed in a graph format such as a flowchart, and thus the user can appropriately grasp the composite synthesis process.

A synthesis process generation apparatus according to an aspect of the present disclosure includes a material word extractor that extracts material words indicating starting materials and a target material from a document, a treatment word extractor that extracts a treatment word indicating a treatment applied to material synthesis using the starting materials from the document, a condition extractor that extracts a condition of the treatment as a synthesis condition from the document, a characteristic value extractor that extracts a characteristic value of the target material from the document, and a generator that generates a synthesis process which is a treatment procedure of synthesizing the target material from the starting materials, by associating with each other the material words, the treatment word, the synthesis condition, and the characteristic value that have been extracted.

Accordingly, a synthesis process, which is a treatment procedure of synthesizing a target material from starting materials, can be easily generated from a document. For example, a synthesis process which is graphable structured data can be easily generated from a synthesis process described in a natural language in a document. Thus, the synthesis process described in the document can be presented to a user in an easy-to-understand manner.

A synthesis process analysis apparatus according to an aspect of the present disclosure includes a combiner that combines synthesis processes to generate a composite synthesis process indicating a common part common to the synthesis processes and comprehensively indicating different parts different from each other among the synthesis processes, and a display that displays the composite synthesis process generated by the combiner. Each of the synthesis processes is a treatment procedure of generating a target material from starting materials, and indicates material words indicating the starting materials and the target material, a treatment word indicating a treatment applied to material synthesis using the starting materials, a synthesis condition which is a condition of the treatment, and a characteristic value of the target material in association with each other.

Accordingly, a composite synthesis process is generated from generated synthesis processes. Thus, a common part and different parts of the many synthesis processes can be displayed in an easy-to-understand manner. Accordingly, a search for a synthesis process for a new material can be appropriately supported. Thus, with many latest synthesis processes, the knowledge about material development can be kept broad and up-to-date.

It should be noted that general or specific embodiments may be implemented as a system, a method, an integrated circuit, a computer program, a computer-readable recording medium such as a CD-ROM, or any selective combination thereof.

Hereinafter, embodiments will be described in detail with reference to the drawings.

Each of the embodiments described below illustrates a general or specific example. Numerical values, shapes, materials, elements, arrangement positions and connection forms of the elements, steps, order of the steps, and so forth described in the following embodiments are examples, and are not intended to limit the present disclosure. Among the elements in the following embodiments, an element that is not described in an independent claim indicating the broadest concept will be described as an optional element.

Each of the figures is a schematic diagram and is not necessarily strictly illustrated. In each of the figures, the same components are denoted by the same reference numerals.

First Embodiment

Synthesis Process Search Support System

FIG. 1 is a diagram illustrating an example of a hardware configuration of a synthesis process search support system in a first embodiment.

A synthesis process search support system 10 in the present embodiment includes a computer 310, a display unit 205, a first recording medium 331, a second recording medium 332, and an operation device 340. The synthesis process search support system 10 in the present disclosure is a specific example of a support apparatus.

The computer 310 is, for example, a personal computer or the like, includes a central processing unit (CPU) or a processor and a memory, and executes processing for supporting a search for a synthesis process. The computer 310 in the present embodiment generates synthesis processes and analyzes the synthesis processes. Each of the generated synthesis processes is electronic data indicating a treatment procedure of synthesizing a target material from starting materials, and is also called process information. The generated synthesis process is, for example, structured data configured to be graphable. A starting material is a material from which a target material is generated, and the target material is a material generated by synthesis.

The display unit 205 displays an image in accordance with an output from the computer 310. For example, the display unit 205 displays a synthesis process generated by the computer 310 and an analysis result of synthesis processes.

The first recording medium 331 is, for example, a hard disk, and holds documents. These documents are electronic data and are, for example, electronic papers. In the present embodiment, the first recording medium 331 is connected to the computer 310 via a communication network 320 such as the Internet. Alternatively, the first recording medium 331 may be connected to the computer 310 without via the communication network 320. The first recording medium 331 may be a recording medium other than a hard disk, for example, a random access memory (RAM), a read only memory (ROM), a semiconductor memory, or the like. The first recording medium 331 may be volatile or nonvolatile.

Similarly to the first recording medium 331, the second recording medium 332 is, for example, a hard disk, and has a recording capacity for holding synthesis processes generated by the computer 310. In the present embodiment, the second recording medium 332 is connected to the computer 310. Alternatively, the second recording medium 332 may be incorporated in the computer 310.

The operation device 340 includes, for example, a keyboard, a mouse, or the like. When being operated by a user, the operation device 340 outputs a signal indicating a result of the operation to the computer 310.

FIG. 2 is a block diagram illustrating an example of a functional configuration of the synthesis process search support system in the first embodiment.

As illustrated in FIG. 2, the synthesis process search support system 10 in the present embodiment includes a synthesis process generation apparatus 100 and a synthesis process analysis apparatus 200. The synthesis process generation apparatus 100 and the synthesis process analysis apparatus 200 in the present disclosure are specific examples of a generation apparatus and an analysis apparatus.

The synthesis process generation apparatus 100 generates a synthesis process which is a treatment procedure of synthesizing a target material from starting materials. Specifically, the synthesis process generation apparatus 100 generates, for each of documents, a synthesis process which is a treatment procedure of synthesizing a target material from starting materials on the basis of a description of the document. The document may be image data, or may be data in a text format. Alternatively, the document may be data in a portable document format (PDF). The PDF document may be data in which text is embedded or may be imaged data in which no text is embedded.

The synthesis process generation apparatus 100 includes a document selection unit 101, a document accumulation unit 102, a material word extraction unit 103, a treatment word extraction unit 104, a condition extraction unit 105, a characteristic value extraction unit 106, and a generation unit 107. The document accumulation unit 102 is configured as the first recording medium 331 described above. In the synthesis process generation apparatus 100, the elements other than the document accumulation unit 102, that is, the document selection unit 101, the material word extraction unit 103, the treatment word extraction unit 104, the condition extraction unit 105, the characteristic value extraction unit 106, and the generation unit 107 are implemented by the computer 310.

The synthesis process analysis apparatus 200 analyzes synthesis processes generated by the synthesis process generation apparatus 100. In the analysis of synthesis processes, the synthesis process analysis apparatus 200 in the present embodiment displays the synthesis processes in a combined manner.

The synthesis process analysis apparatus 200 includes a synthesis process accumulation unit 201, a search condition acceptance unit 202, a search unit 203, a combining unit 204, and a display unit 205. The synthesis process accumulation unit 201 is configured as the second recording medium 332 described above. In the synthesis process analysis apparatus 200, the search condition acceptance unit 202, the search unit 203, and the combining unit 204 are implemented by the computer 310.

Although the operation device 340 is not illustrated in FIG. 2, the synthesis process generation apparatus 100 and the synthesis process analysis apparatus 200 execute processing in accordance with a signal indicating a user's operation result output from the operation device 340. In the present embodiment, the display unit 205 is provided in the synthesis process analysis apparatus 200, but need not necessarily be provided in the synthesis process analysis apparatus 200. In this case, the display unit 205 may be connected to at least one of the synthesis process generation apparatus 100 or the synthesis process analysis apparatus 200.

Document Accumulation Unit

As described above, the document accumulation unit 102 is configured as the first recording medium 331 illustrated in FIG. 1 and holds documents.

Document Selection Unit

The document selection unit 101 sequentially selects each of the documents accumulated in the document accumulation unit 102 as an extraction-target document. The document selection unit 101 may select extraction-target documents in a predetermined order, or may select an extraction-target document in accordance with a user operation.

Material Word Extraction Unit

The material word extraction unit 103 extracts material words from each of the documents accumulated in the document accumulation unit 102, and outputs the extracted material words to the generation unit 107. That is, the material word extraction unit 103 extracts material words indicating starting materials and a target material from one extraction-target document among the documents. For example, the material word extraction unit 103 searches the extraction-target document for a material word described in a dictionary described blow, and extracts the material word from the extraction-target document.

Treatment Word Extraction Unit

The treatment word extraction unit 104 extracts at least one treatment word from each of the documents accumulated in the document accumulation unit 102, and outputs the at least one extracted treatment word to the generation unit 107. That is, the treatment word extraction unit 104 extracts, from an extraction-target document, a treatment word indicating a treatment applied to material synthesis using starting materials. For example, the treatment word extraction unit 104 searches the extraction-target document for a treatment word described in a dictionary described below, and extracts the treatment word from the extraction-target document. Specifically, the treatment is, for example, at least one of a heat treatment, a mixing treatment, a drying treatment, or a dissolution treatment. Thus, the treatment word extraction unit 104 extracts a treatment word indicating at least one of a heat treatment, a mixing treatment, a drying treatment, or a dissolution treatment.

Condition Extraction Unit

The condition extraction unit 105 extracts a synthesis condition related to a treatment word from each of the documents accumulated in the document accumulation unit 102, and outputs the extracted synthesis condition to the generation unit 107. That is, the condition extraction unit 105 extracts, from an extraction-target document, a condition of the above-described treatment as a synthesis condition. For example, the condition extraction unit 105 searches the extraction-target document for a synthesis condition word described in a dictionary described below, and extracts a synthesis condition including the synthesis condition word from the extraction-target document. Specifically, the synthesis condition is at least one of a temperature, a time, a pressure, or a rotation speed each of which is indicated by a numerical value and a unit. Thus, the condition extraction unit 105 extracts, as a synthesis condition, at least one of a temperature, a time, a pressure, or a rotation speed each of which is indicated by a numerical value and a unit.

Characteristic Value Extraction Unit

The characteristic value extraction unit 106 extracts a characteristic value of a target material from each of the documents accumulated in the document accumulation unit 102, and outputs the extracted characteristic value to the generation unit 107. That is, the characteristic value extraction unit 106 extracts a characteristic value of a target material from an extraction-target document. For example, the characteristic value extraction unit 106 searches the extraction-target document for a characteristic value word described in a dictionary described below, and extracts a characteristic value including the characteristic value word from the extraction-target document. Specifically, the characteristic value is, for example, a conductivity, a mobility, an energy, or the like.

Generation Unit

The generation unit 107 generates, for each of the documents accumulated in the document accumulation unit 102, a synthesis process by associating material words, a treatment word, a synthesis condition, and a characteristic value extracted from the document. The generation unit 107 then outputs the generated synthesis process to the synthesis process accumulation unit 201. That is, the generation unit 107 associates material words, a treatment word, a synthesis condition, and a characteristic value extracted from an extraction-target document with each other, thereby generating a synthesis process. For example, the generation unit 107 associates the material words, the treatment word, the synthesis condition, and the characteristic value with each other on the basis of relevance described in a dictionary described below. The generation unit 107 may associate the material words, the treatment word, the synthesis condition, and the characteristic value in the document in association with each other on the basis of the appearance order or positional relationship thereof.

In this way, the generation apparatus which is the synthesis process generation apparatus 100 in the present embodiment executes the following (a-1) to (a-5) with i=1 to n, and generates process information 1 to process information n which are pieces of process information. Note that i is a natural number and n is a natural number greater than or equal to 2. In (a-1), the material word extraction unit 103 included in the generation apparatus extracts material words from a document i, the material words including starting material words indicating starting materials and a target material word indicating a target material. In (a-2), the treatment word extraction unit 104 included in the generation apparatus extracts a treatment word i from the document i, the treatment word i indicating a treatment i of generating the target material from the starting materials. In (a-3), the condition extraction unit 105 included in the generation apparatus extracts a synthesis condition i from the document i, the synthesis condition i being a condition i of the treatment i. In (a-4), the characteristic value extraction unit 106 included in the generation apparatus extracts a characteristic value i related to the target material from the document i. In (a-5), the generation unit 107 included in the generation apparatus associates the material words, the treatment word i, the synthesis condition i, and the characteristic value i with each other to generate process information i indicating a procedure i of generating the target material from the starting materials.

Synthesis Process Accumulation Unit

The synthesis process accumulation unit 201 accumulates, for each of synthesis processes generated by the synthesis process generation apparatus 100, the synthesis process and bibliographic information of a document corresponding to the synthesis process in association with each other.

Search Condition Acceptance Unit

The search condition acceptance unit 202 accepts a search condition for the synthesis processes accumulated in the synthesis process accumulation unit 201. For example, the search condition acceptance unit 202 accepts a search condition corresponding to a signal indicating a user operation result output from the operation device 340.

Search Unit

The search unit 203 searches the synthesis processes accumulated in the synthesis process accumulation unit 201 for a synthesis process that satisfies the search condition accepted by the search condition acceptance unit 202. That is, the search unit 203 searches m (m is an integer greater than or equal to 2) synthesis processes generated by the synthesis process generation apparatus 100 for n (n is an integer smaller than or equal to m) synthesis processes. In other words, in the generation of pieces of process information, the above-described generation apparatus executes the above-described (a-1) to (a-5) with i=1 to m, and generates process information 1 to process information m. Note that m is a natural number greater than or equal to n. In this case, the search unit 203 included in the analysis apparatus searches the process information 1 to the process information m generated by the generation apparatus for the process information 1 to the process information n.

Combining Unit

When the number of synthesis processes found through the search performed by the search unit 203 is two or more, that is, when n is two or more, the combining unit 204 combines the n synthesis processes. That is, the combining unit 204 combines the n synthesis processes generated by the synthesis process generation apparatus 100, thereby generating a composite synthesis process indicating a part common to the n synthesis processes and comprehensively indicating parts different from each other among the n synthesis processes. Similarly to the synthesis process, the composite synthesis process is electronic data indicating a treatment procedure of synthesizing a target material from starting materials, and is also called composite process information. In the present disclosure, combining of synthesis processes means generating of composite process information from pieces of process information.

Display Unit

The display unit 205 is configured as, for example, a liquid crystal display, a plasma display, an organic electroluminescence (EL) display, or the like. The display unit 205 displays a composite synthesis process generated by the combining unit 204. In the present disclosure, the display unit 205 is a specific example of an outputter. That is, the display unit 205 in the present embodiment displays the composite synthesis process, that is, composite process information, as an image, thereby outputting the composite process information. Alternatively, the composite process information may be output as a sound or may be output as electronic data to another apparatus.

Dictionaries

FIG. 3A is a diagram illustrating dictionaries respectively used in the material word extraction unit 103 and the treatment word extraction unit 104. FIG. 3B is a diagram illustrating dictionaries respectively used in the condition extraction unit 105 and the characteristic value extraction unit 106.

The material word extraction unit 103 has a material word dictionary illustrated in part (a) of FIG. 3A. The material word dictionary shows material words and attributes of the material words. The attribute of a material word is a starting material or a target material. For example, the material word dictionary shows a material word "$Li_2CO_3$" and an attribute "starting material" of the material word. Also, the material word dictionary shows a material word "$Li_{1.1}Mg_{0.6}Ti_{1.9}(PO_4)_3$" and an attribute "target material" of the material word. The material word extraction unit 103 searches a document for a material word shown in the material word dictionary and extracts the material word from the document. At this time, the material word extraction unit 103 specifies the attribute of the extracted material word by referring to the material word dictionary, and adds the attribute to the material word. The material word extraction unit 103 then outputs the material word having the attribute added thereto to the generation unit 107.

The treatment word extraction unit 104 has a treatment word dictionary illustrated in part (b) of FIG. 3A. The treatment word dictionary shows treatment words and attributes of the treatment words. For example, the treatment word dictionary shows a treatment word "heat" and an attribute "heat treatment" of the treatment word. Also, the treatment word dictionary shows a treatment word "mix" and an attribute "mixing treatment" of the treatment word. The treatment word extraction unit 104 searches a document for a treatment word shown in the treatment word dictionary and extracts the treatment word from the document. At this time, the treatment word extraction unit 104 specifies the attribute of the extracted treatment word by referring to the treatment word dictionary, and adds the attribute to the treatment word. The treatment word extraction unit 104 then outputs the treatment word having the attribute added thereto to the generation unit 107.

Here, when the treatment word extraction unit 104 searches a document for a treatment word shown in the treatment word dictionary, the treatment word extraction unit 104 may search for not only the treatment word but also at least one of an inflected form or a derivative form of the treatment word. In addition, the treatment word extraction unit 104 may search for a stem of a treatment word shown in the treatment word dictionary and may extract a word having the stem as a treatment word. For example, the treatment word extraction unit 104 searches for not only the treatment word "heat" shown in the treatment word dictionary but also "heated", "heating", and the like. Also, the treatment word extraction unit 104 searches for not only the treatment word "mix" shown in the treatment word dictionary but also "mixtures" and the like. In addition, the treatment word extraction unit 104 may search a document for a treatment word regardless of the character form (for example, uppercase, lowercase, or font) of the treatment word shown in the treatment word dictionary.

The condition extraction unit 105 has a condition word dictionary illustrated in part (a) of FIG. 3B. The condition word dictionary shows synthesis condition words, and attributes and examples of the synthesis condition words. For example, the condition word dictionary shows a synthesis condition word "° C.", and an attribute "temperature" and an example "at 900° C." of the synthesis condition word. Furthermore, for example, the condition word dictionary shows a synthesis condition word "K", and an attribute "temperature" and an example "at 300-400 K" of the synthesis condition word. In addition, the condition word dictionary shows a synthesis condition word "Room Temperature", and an attribute "temperature" and an example "at room temperature" of the synthesis condition word.

The condition extraction unit 105 searches a document for a synthesis condition word shown in the condition word dictionary and extracts a synthesis condition including the synthesis condition word from the document. Specifically, if a numerical value is used in an example of a synthesis condition word shown in the condition word dictionary, the condition extraction unit 105 extracts a synthesis condition including the synthesis condition word and a numerical value located near the synthesis condition word from the document. For example, if "at 300-400 K" is shown as an example of a synthesis condition word "K" in the condition word dictionary, the condition extraction unit 105 extracts a synthesis condition including the synthesis condition word "K" and a numerical value immediately before the synthesis condition word "K" from the document. A numerical value may include a power of 10 such as "M", for example, "100M".

On the other hand, if a numerical value is not used in an example of a synthesis condition word shown in the condition word dictionary, the condition extraction unit 105 extracts the synthesis condition word as a synthesis condition from the document. For example, if "at room temperature" is shown as an example of a synthesis condition word "Room Temperature" in the condition word dictionary, the condition extraction unit 105 extracts a synthesis condition word "room temperature" as a synthesis condition from the document. That is, at this time, the condition extraction unit 105 does not extract a numerical value. In addition, the condition extraction unit 105 may search a document for a synthesis condition word regardless of the character form (for example, uppercase, lowercase, or font) of the synthesis condition word shown in the condition word dictionary.

The condition word dictionary may show a range of a numerical value used for a synthesis condition word. In this case, the condition extraction unit 105 searches for and extracts a synthesis condition including a numerical value within the range.

Furthermore, the condition extraction unit 105 specifies an attribute of a synthesis condition word included in the extracted synthesis condition by referring to the condition word dictionary, and adds the attribute to the synthesis condition. The condition extraction unit 105 then outputs the synthesis condition having the attribute added thereto to the generation unit 107.

The characteristic value extraction unit 106 has a characteristic value dictionary illustrated in part (b) of FIG. 3B. The characteristic value dictionary shows characteristic value words. A characteristic value word is a unit for indicating a characteristic value. For example, the characteristic value dictionary shows characteristic value words "S/cm", "cm$^2$/", "eV", and so forth.

The characteristic value extraction unit 106 searches a document for a characteristic value word shown in the characteristic value dictionary, and extracts a characteristic value including the characteristic value word and a numerical value immediately before the characteristic value word from the document. For example, the characteristic value extraction unit 106 extracts, from the document, a characteristic value including a characteristic value word "S/cm" and a numerical value immediately before the characteristic value word "S/cm". Alternatively, the characteristic value extraction unit 106 extracts, from the document, a characteristic value including a characteristic value word "eV" and a numerical value immediately before the characteristic value word "eV". The condition extraction unit 105 then outputs the extracted characteristic value to the generation unit 107.

FIG. 4 is a diagram illustrating dictionaries used in the generation unit 107.

The generation unit 107 has a first relevance dictionary illustrated in part (a) of FIG. 4. The first relevance dictionary shows treatment words and attributes of materials relevant to the treatment words. An attribute of a material is a starting material or a target material. For example, the first relevance dictionary shows a treatment word "mix" and an attribute "starting material" of a material relevant to the treatment word. The generation unit 107 associates a treatment word and a material word extracted from a document with each other by referring to the first relevance dictionary illustrated in part (a) of FIG. 4.

The generation unit 107 has a second relevance dictionary illustrated in part (b) of FIG. 4. The second relevance dictionary shows treatment words and attributes of synthesis conditions relevant to the treatment words. The number of attributes of a synthesis condition relevant to one treatment word is not limited to one and may be two or more. For example, the second relevance dictionary shows a treatment word "heat", and an attribute 1 "temperature" and an attribute 2 "time" of a synthesis condition relevant to the treatment word "heat".

The generation unit 107 associates a treatment word and a synthesis condition extracted from a document with each other by referring to the second relevance dictionary illustrated in part (b) of FIG. 4.

Generation of Synthesis Process

FIG. 5 is a diagram illustrating an example of documents accumulated in the document accumulation unit 102 of the synthesis process generation apparatus 100.

As illustrated in FIG. 5, the document accumulation unit 102 accumulates, for example, electronic papers as documents. The document selection unit 101 selects any one of the documents as an extraction-target document. The document selection unit 101 then specifies an extraction-target region in the extraction-target document. For example, the document selection unit 101 specifies, as an extraction-target region, a region in which a predetermined item name is described. Alternatively, the document selection unit 101 may search for a word shown in the dictionary illustrated in FIG. 3A or FIG. 3B, and may specify, as an extraction-target region, a region in which the appearance frequency of the word is the highest or a region in which the appearance frequency is higher than a threshold. Alternatively, the extraction-target region may be set in the document in advance or may be randomly set by a user.

The document selection unit 101 outputs the extraction-target document whose extraction-target region is explicitly indicated to the material word extraction unit 103, the treatment word extraction unit 104, the condition extraction unit 105, and the characteristic value extraction unit 106. To explicitly indicate the extraction-target region, a tag or a page number and a line number may be used, for example. That is, in the extraction-target document, information indicating a start point and an end point of the extraction-target region may be indicated by a tag or the like, or information indicating the start point and the end point may be indicated by a page number and a line number, or the like.

In the extraction-target region illustrated in FIG. 5, to facilitate the understanding of the contents described in the extraction-target region, numbers are assigned to the heads of the sentences included in the extraction-target region in the order of appearance of the sentences.

FIG. 6 is a diagram illustrating an example of words, synthesis conditions, and a characteristic value extracted from the extraction-target region of the document.

For example, when the extraction-target region illustrated in FIG. 5 has been specified by the document selection unit 101, the material word extraction unit 103 extracts material words from the extraction-target region by referring to the material word dictionary illustrated in part (a) of FIG. 3A. For example, the material word extraction unit 103 extracts a material word "$Li_{1.1}Mg_{0.6}Ti_{1.9}(PO_4)_3$" of a target material and material words "$Li_2CO_3$", "MgO", "$TiO_2$", and "$NH_4H_2PO_4$" of starting materials.

The treatment word extraction unit 104 extracts a treatment word from the extraction-target region by referring to the treatment word dictionary illustrated in part (b) of FIG. 3A. For example, the treatment word extraction unit 104 extracts treatment words "mixtures", "milled", and so forth.

The condition extraction unit 105 extracts a synthesis condition from the extraction-target region by referring to the condition word dictionary illustrated in part (a) of FIG. 3B. For example, the condition extraction unit 105 extracts synthesis conditions "20 h", "334 K", "6 h", and so forth.

The characteristic value extraction unit 106 extracts a characteristic value of the target material from the extraction-target region by referring to the characteristic value dictionary illustrated in part (b) of FIG. 3B. For example, the characteristic value extraction unit 106 extracts a characteristic value "0.00013 S/cm".

FIG. 7 is a diagram illustrating an example of material words, treatment words, synthesis conditions, and a characteristic value that have been extracted.

For example, as illustrated in part (a) of FIG. 7, a material word "$Li_{1.1}Mg_{0.6}Ti_{1.9}(PO_4)_3$" having an attribute "target material" and material words "$Li_2CO_3$", "$MgO$", "$TiO_2$", and "$NH_4H_2PO_4$" having an attribute "starting material" are extracted.

The material word extraction unit 103 may extract a material word that is not shown in the material word dictionary illustrated in part (a) of FIG. 3A. In this case, the material word extraction unit 103 may divide the sentences in the document into words and may extract a material word from the structure of the sentences. When a material word described in the document includes a variable, the material word extraction unit 103 may extract a material word in which a numerical value has been assigned to the variable. For example, when "$Li_4Ti_{(5-x)}La_{(x)}O_{12}$ [x=0, 0.05, 0.1]" is described in the document, the material word extraction unit 103 assigns 0, 0.05, and 0.1 to x and extracts material words "$Li_4Ti_5O_{12}$", "$Li_4Ti_{4.95}La_{0.05}O_{12}$", and "$Li_4Ti_{4.9}La_{0.1}O_{12}$".

In addition, as illustrated in part (b) of FIG. 7, treatment words "mixtures", "heating", "milled", and so forth are extracted. These extracted treatment words have attributes added thereto. In addition, as illustrated in part (c) of FIG. 7, synthesis conditions "20 h", "773 K", "5 h", and so forth are extracted. These extracted synthesis conditions have attributes added thereto. Furthermore, as illustrated in part (d) of FIG. 7, a characteristic value "$1.30 \times 10^{-4}$ S/cm" is extracted.

The individual extraction units such as the material word extraction unit 103, the treatment word extraction unit 104, the condition extraction unit 105, and the characteristic value extraction unit 106 may perform natural language processing, such as morphological analysis, syntactic analysis, or context analysis, on the sentences described in the document. That is, individual words, synthesis conditions, and a characteristic value may be searched for and extracted by such natural language processing. When the document is image data, the individual extraction units may perform optical character recognition/reader (OCR) on the image data to convert the image data into text data, and may extract individual words and so forth from the text data. Alternatively, the individual extraction units may extract individual words and so forth by image recognition, or may extract individual words and so forth by using machine learning.

FIG. 8 is a diagram illustrating an example of a synthesis process generated as structured data.

The generation unit 107 generates a synthesis process by using the material words, the treatment words, the synthesis conditions, and the characteristic value illustrated in FIG. 7. This synthesis process is structured data and is configured to be graphable. The generation unit 107 may use the extracted treatment words as illustrated in FIG. 7 for the synthesis process, or may use the bare infinitives of the extracted treatment words, that is, the treatment words shown in the treatment word dictionary illustrated in part (b) of FIG. 3A, for the synthesis process.

Specifically, as illustrated in part (a) of FIG. 8, the generation unit 107 assigns a word ID (for example, W1, W2, or the like) to each of the extracted material words, treatment words, and synthesis conditions. The extracted material words, treatment words, and synthesis conditions have attributes added thereto.

Furthermore, the generation unit 107 selects one word ID from among the word IDs assigned as described above, and searches for a word ID relevant to the selected word ID. The generation unit 107 then associates the selected word ID with the word ID found through the search, and assigns a relationship ID to the pair of the associated word IDs, as illustrated in part (b) of FIG. 8.

For example, the generation unit 107 associates the word ID of a treatment word extracted from the document with the word ID of a material word by referring to the first relevance dictionary illustrated in part (a) of FIG. 4. Specifically, the generation unit 107 selects the treatment word "mixtures" extracted from the document by the treatment word extraction unit 104. Subsequently, the generation unit 107 searches the first relevance dictionary for a treatment word "mix", which is the bare infinitive of the treatment word "mixtures". Subsequently, the generation unit 107 specifies "starting material" as an attribute of a material relevant to the treatment word "mix" by referring to the first relevance dictionary. Here, each extracted material word has an attribute added thereto, as illustrated in part (a) of FIG. 8.

Thus, the generation unit 107 associates, with the selected treatment word "mixtures", the material words having the specified attribute "starting material" added thereto among the extracted material words. At this time, the generation unit 107 may associate, with the selected treatment word "mixtures", only a material word that is within a predetermined number of words before or after the selected treatment word "mixtures" in a sentence included in the document among the material words having an attribute "starting material". For example, the generation unit 107 associates the material word "$Li_2CO_3$" having an attribute "starting material" with the selected treatment word "mixtures". Accordingly, as illustrated in part (b) of FIG. 8, the word ID "W1" of the material word "$Li_2CO_3$" is associated with the word ID "W5" of the treatment word "mix", which is the bare infinitive of the treatment word "mixtures". The generation unit 107 assigns a relationship ID "R1" to the pair of the word ID "W1" and the word ID "W5".

In addition, the generation unit 107 associates the word ID of a treatment word extracted from the document with the word ID of a synthesis condition by referring to the second relevance dictionary illustrated in part (b) of FIG. 4. Specifically, the generation unit 107 selects the treatment word "mixtures" extracted from the document by the treatment word extraction unit 104. Subsequently, the generation unit 107 searches the second relevance dictionary for a treatment word "mix", which is the bare infinitive of the treatment word "mixtures". Subsequently, the generation unit 107 specifies "temperature" and "time" as attributes of a synthesis condition relevant to the treatment word "mix" by referring to the second relevance dictionary. Here each extracted synthesis condition has an attribute added thereto, as illustrated in part (a) of FIG. 8.

Thus, the generation unit 107 associates, with the selected treatment word "mixtures", the synthesis conditions having the specified attribute "temperature" added thereto among the extracted synthesis conditions. At this time, the generation unit 107 may associate, with the selected treatment word "mixtures", only a synthesis condition that is within a predetermined number of words before or after the selected treatment word "mixtures" in a sentence included in the document among the synthesis conditions having an attribute "temperature". For example, the generation unit 107 associates the synthesis condition "773 K" having an attribute "temperature" with the selected treatment word "mixtures". Accordingly, as illustrated in part (b) of FIG. 8, the word ID "W7" of the synthesis condition "773 K" is associated with the word ID "W5" of the treatment word "mix", which is the bare infinitive of the treatment word "mixtures". The generation unit 107 assigns a relationship ID "R6" to the pair of the word ID "W7" and the word ID "W5". Similarly to such processing, the generation unit 107 associates, with the selected treatment word "mixtures", the synthesis conditions having the specified attribute "time" added thereto among the extracted synthesis conditions. Accordingly, as illustrated in part (b) of FIG. 8, the word ID "W6" of the synthesis condition "20 h" is associated with the word ID "W5" of the treatment word "mix", which is the bare infinitive of the treatment word "mixtures". The generation unit 107 assigns a relationship ID "R5" to the pair of the word ID "W6" and the word ID "W5".

In addition, the generation unit 107 associates the word ID of a treatment word extracted from the document with the word ID of a treatment word that appears subsequently to the treatment word. Specifically, the generation unit 107 selects the treatment word "mixtures" extracted from the document by the treatment word extraction unit 104. Subsequently, the generation unit 107 selects a treatment word "heating" that appears subsequently to the treatment word "mixtures" in the document from among the treatment words extracted from the document. Subsequently, the generation unit 107 associates the treatment word "mix", which is the bare infinitive of the treatment word "mixtures", with the treatment word "heat", which is the bare infinitive of the treatment word "heating". Accordingly, as illustrated in part (b) of FIG. 8, the word ID "W5" of the treatment word "mix" is associated with the word ID "W8" of the treatment word "heat". The generation unit 107 assigns a relationship ID "R7" to the pair of the word ID "W5" and the word ID "W8". When a treatment word "milled" appears subsequently to the treatment word "heating" in the document, the generation unit 107 associates a treatment word "heat", which is the bare infinitive of the treatment word "heating", with a treatment word "mill", which is the bare infinitive of the treatment word "milled", similarly to the above-described processing. Accordingly, as illustrated in part (b) of FIG. 8, the word ID "W11" of the treatment word "mill" is associated with the word ID "W8" of the treatment word "heat". The generation unit 107 assigns a relationship ID "R10" to the pair of the word ID "W11" and the word ID "W8".

The generation unit 107 assigns a characteristic value ID to the extracted characteristic value, as illustrated in part (c) of FIG. 8. For example, a characteristic value ID "V1" is assigned to the extracted characteristic value "1.30×10$^{-4}$ S/cm". In addition, the generation unit 107 associates the characteristic value ID with the word ID of a material word having an attribute "target material". When there are material words each having an attribute "target material" and characteristic values in a document, the generation unit 107 associates the material words with the characteristic values on the basis of the order in which the material words appear. For example, there is a sentence "ionic conductivities of $Li_4Ti_5O_{12}$, $Li_4Ti_{0.95}La_{0.05}O_{12}$, and $Li_4Ti_{4.9}La_{0.1}O_{12}$ were 0.1, 0.35, and 0.56 S/cm" in a document. In this case, the generation unit 107 associates the material word "$Li_4Ti_5O_{12}$" with the characteristic value "0.1 S/cm" and associates the material word "$Li_4Ti_{0.95}La_{0.05}O_{12}$" with the characteristic value "0.35 S/cm" on the basis of the order in which the material words having an attribute "target material" appear. Furthermore, the generation unit 107 associates the material word "$Li_4Ti_{4.9}La_{0.1}O_{12}$" with the characteristic value "0.56 S/cm".

When it is described in a document that a material A is synthesized from starting materials, then a material B is synthesized, and then a material C is synthesized, the material A and the material B are intermediate materials, and the material C is a target material. However, the material word of each of the material A and the material B may also be extracted as a material word of a target material by the material word extraction unit 103. Also in this case, the document has material words each having an attribute "target material" and characteristic values. Thus, similarly to the above, the generation unit 107 may associate the material words with the characteristic values on the basis of the order in which the material words appear.

The generation unit 107 may associate a treatment word with a material word or may associate a treatment word with a synthesis condition by performing natural language processing, similarly to the individual extraction units described above. The generation unit 107 may switch an association method according to the type of language (for example, Japanese or English) described in the document. For example, if the document is described in English and if a verb corresponding to a treatment word described in the document is followed by a noun, the generation unit 107 may associate the treatment word with a material word corresponding to the noun. On the other hand, if the document is described in Japanese and if there is a noun before a verb corresponding to a treatment word described in the document, the generation unit 107 may associate the treatment word with a material word corresponding to the noun.

Figure 9:
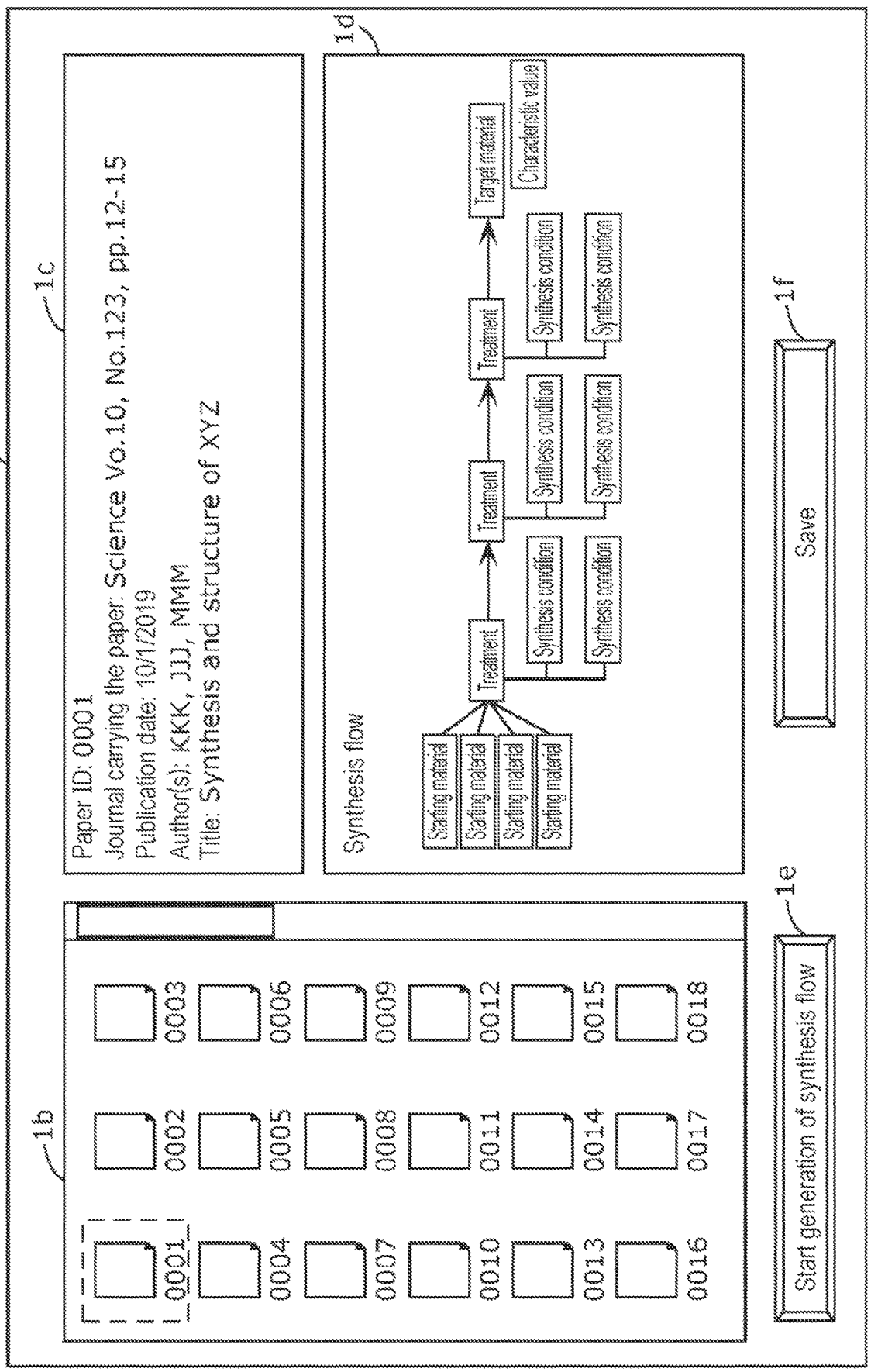
FIG. 9 is a diagram illustrating an example of a synthesis process generation screen displayed on a display unit in the first embodiment.

FIG. 9 is a diagram illustrating an example of a synthesis process generation screen displayed on the display unit 205.

For example, the document selection unit 101 causes the display unit 205 to display a synthesis process generation screen 1a illustrated in FIG. 9 in response to a signal indicating a user operation result output from the operation device 340.

The synthesis process generation screen 1a includes a list window 1b, a bibliographic window 1c, a synthesis flow window 1d, a generation start button 1e, and a save button 1f.

A list of documents accumulated in the document accumulation unit 102 is displayed on the list window 1b. The generation start button 1e is a button for providing an instruction to start generating a synthesis process. For example, a user selects a document having a file name "0001" displayed on the list window 1b by operating the operation device 340. The user then selects the generation start button 1e by operating the operation device 340. As a result, the document selection unit 101 selects the document having the file name "0001" from among the documents accumulated in the document accumulation unit 102 as an extraction-target document. Furthermore, the document selection unit 101 outputs the extraction-target document to the material word extraction unit 103, the treatment word extraction unit 104, the condition extraction unit 105, and the characteristic value extraction unit 106. Accordingly, generation of a synthesis process from the extraction-target document is executed.

Bibliographic information of the extraction-target document is displayed on the bibliographic window 1c. For example, the document selection unit 101 extracts bibliographic information from the extraction-target document and displays the bibliographic information on the bibliographic window 1c. The bibliographic information includes, for example, the name of a journal carrying the extraction-target document, a publication date, an author name, and a title. When the extraction-target document is a paper, the bibliographic information may include a paper ID assigned to the paper. In this case, the file name of the document may be the paper ID.

A generated synthesis process is graphed and displayed on the synthesis flow window $1d$. This graphed synthesis process will be hereinafter referred to as a synthesis flow. For example, after generating the synthesis process illustrated in FIG. 8, the generation unit 107 displays the synthesis process as a synthesis flow on the synthesis flow window $1d$. This synthesis flow indicates, in the form of a flowchart, a treatment procedure in which at least one treatment is performed on starting materials to generate a target material. The synthesis flow further indicates synthesis conditions used for the treatments and a characteristic value of the target material.

The save button $1f$ is a button for saving a generated synthesis process. For example, when a synthesis flow is displayed on the synthesis flow window $1d$, the user selects the save button $1f$ by operating the operation device 340. Accordingly, the generation unit 107 acquires a signal indicating a result of the operation from the operation device 340, and outputs the generated synthesis process to the synthesis process accumulation unit 201 in response to the signal. Accordingly, the generated synthesis process is accumulated or saved in the synthesis process accumulation unit 201.

In the example illustrated in FIG. 9, a synthesis process is generated from a document selected by the user. Alternatively, a synthesis process may be automatically generated from each document accumulated in the document accumulation unit 102 and may be accumulated in the synthesis process accumulation unit 201.

Figure 10:
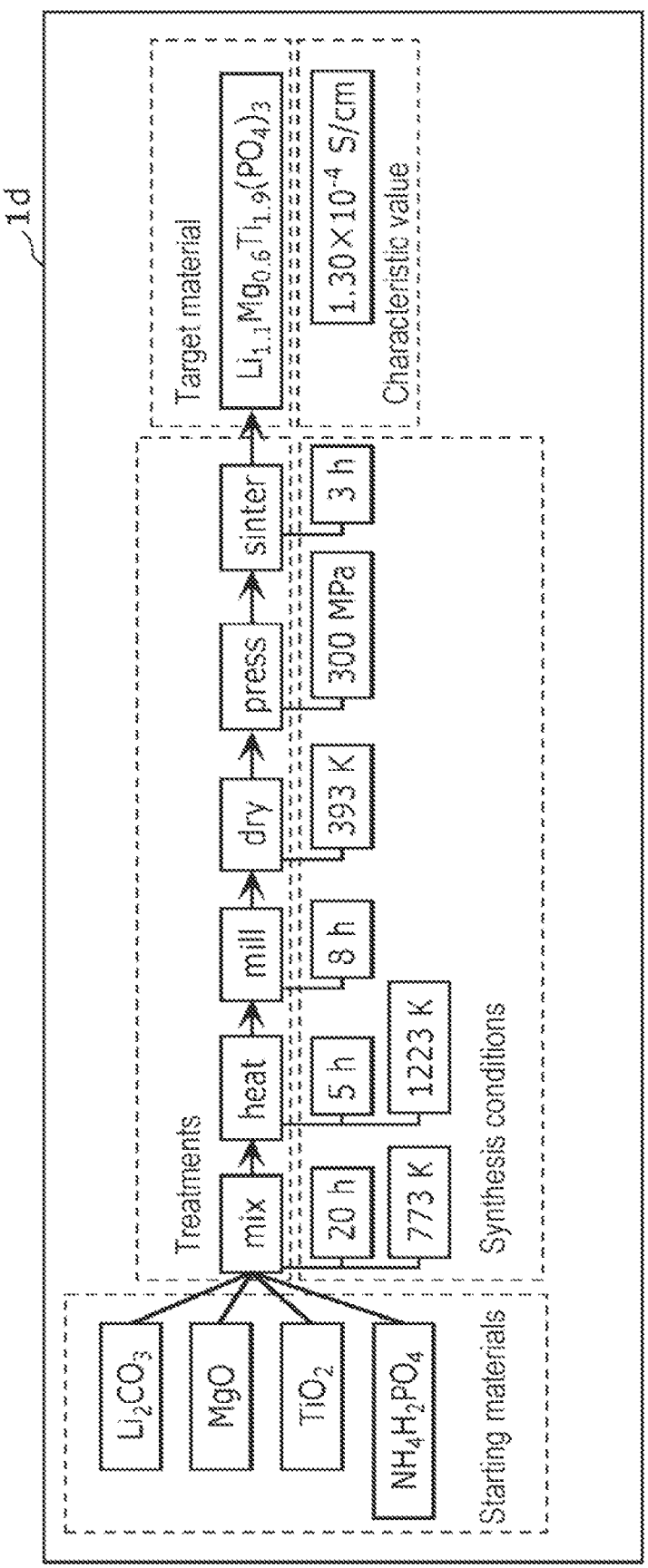
FIG. 10 is a diagram illustrating an example of a synthesis flow displayed on a synthesis flow window in the first embodiment.

FIG. 10 is a diagram illustrating an example of a synthesis flow displayed on the synthesis flow window $1d$.

The synthesis flow includes material words of starting materials, at least one treatment word, synthesis conditions used for treatments of these treatment words, a material word of a target material, and a characteristic value of the target material. The synthesis flow illustrated in FIG. 10 is, for example, a flow obtained by graphing the synthesis process illustrated in FIG. 8. That is, in the example illustrated in FIG. 10, the material words of the starting materials are "$Li_2CO_3$", "MgO", "$TiO_2$", and "$NH_4H_2PO_4$". The at least one treatment word includes treatment words "mix", "heat", "mill", "dry", "press" and "sinter". The material words of the starting materials are associated with the treatment word "mix", for example by straight lines. When treatment words are included in the synthesis flow as in the example illustrated in FIG. 10, the treatment words are associated with each other by arrows.

A synthesis condition is associated with each treatment word. For example, synthesis conditions "20 h" and "773 K" are associated with the treatment word "mix", and synthesis conditions "5 h" and "1223 K" are associated with the treatment word "heat". The material word of the target material is associated with the last treatment word among the treatment words. In the example illustrated in FIG. 10, the material word of the target material is "$Li_{1.1}Mg_{0.6}Ti_{1.9}(PO_4)_3$". That is, the arrow pointing from the last treatment word "sinter" to the material word "$Li_{1.1}Mg_{0.6}Ti_{1.9}(PO_4)_3$" associates the last treatment word with the material word of the target material.

A characteristic value is arranged near the material word of the target material. For example, a characteristic value "$1.30 \times 10^{-4}$ S/cm" is arranged.

This synthesis flow indicates a treatment procedure of synthesizing the target material "$Li_{1.1}Mg_{0.6}Ti_{1.9}(PO_4)_3$" by performing treatments such as "mix" and "heat" on the starting materials "$Li_2CO_3$", "MgO", "$TiO_2$", and "$NH_4H_2PO_4$". The synthesis flow indicates that the treatment "mix" is performed for 20 hours at a temperature of 773 K. The synthesis flow further indicates that the characteristic value of the target material "$Li_{1.1}Mg_{0.6}Ti_{1.9}(PO_4)_3$" is "$1.30 \times 10^{-4}$ S/cm".

Figure 11:
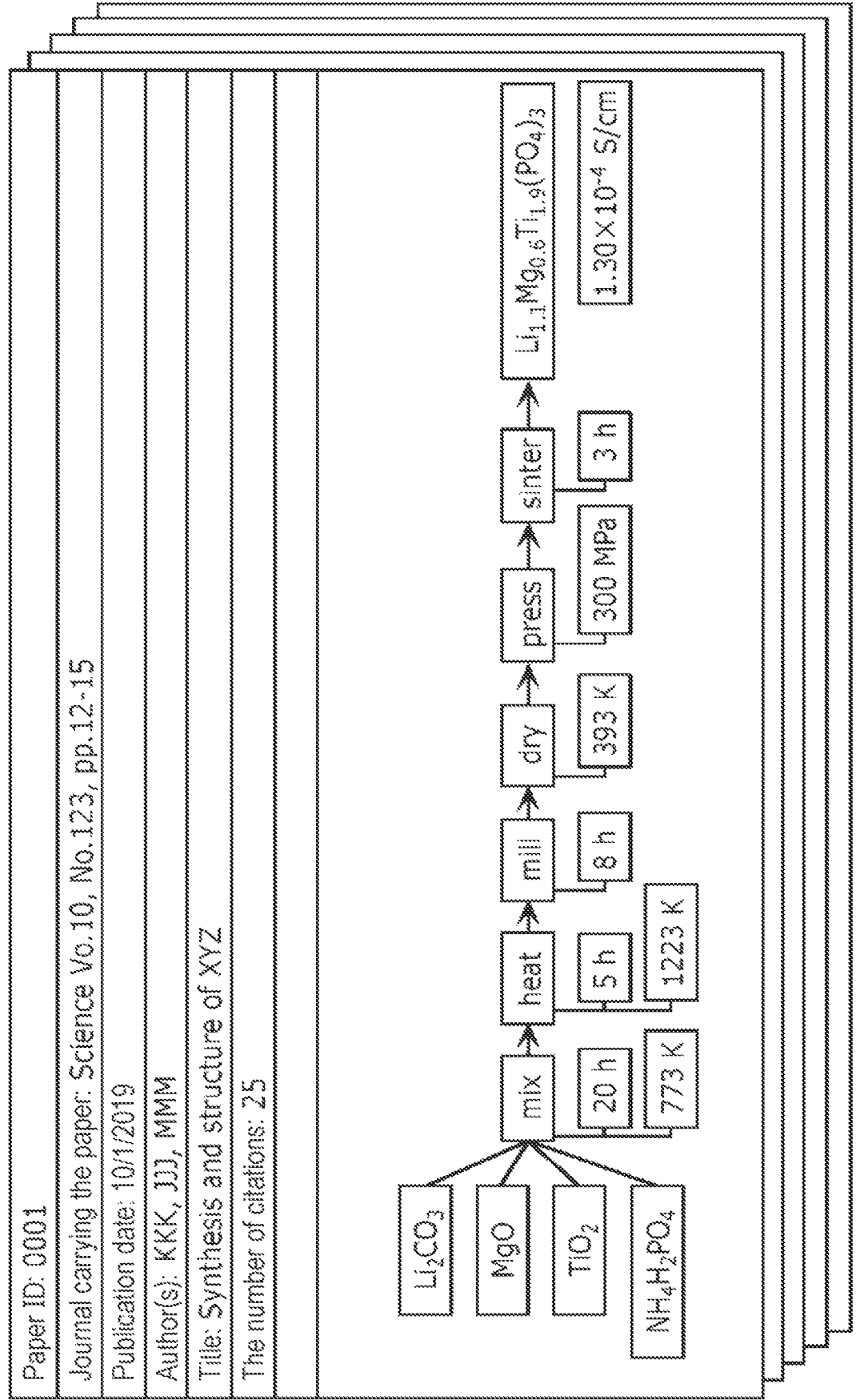
FIG. 11 is a diagram illustrating an example of a synthesis process generated by the generation unit and accumulated in a synthesis process accumulation unit in the first embodiment.

FIG. 11 is a diagram illustrating an example of a synthesis process generated by the generation unit 107 and accumulated in the synthesis process accumulation unit 201.

When storing the synthesis process illustrated in FIG. 8 in the synthesis process accumulation unit 201, the generation unit 107 adds bibliographic information of the document corresponding to the synthesis process to the synthesis process. That is, the generation unit 107 adds, to each of generated synthesis processes, bibliographic information of the document corresponding to the synthesis process. That is, in (a-5) described above, the generation unit 107 adds bibliographic information of the document i to the generated process information i. The bibliographic information includes, for example, the name of a journal carrying the document, a publication date, and an author name. The bibliographic information may also include the title of the document or the name of an organization to which the author belongs. When the document is a paper, the bibliographic information may include a paper ID assigned to the paper or may include the number of citations of the paper. That is, the bibliographic information may indicate at least one of the name of an author of a document corresponding to the bibliographic information, a publication date of the document, the name of an organization to which the author belongs, or the number of citations of the document.

The synthesis process to which the bibliographic information has been added is accumulated in the synthesis process accumulation unit 201. In FIG. 11, the synthesis process is illustrated in the form of a synthesis flow for easy understanding of the synthesis process. However, the synthesis process may be accumulated as structured data illustrated in FIG. 8 instead of in the form of a synthesis flow.

As described above, the synthesis process generation apparatus 100 in the present embodiment is capable of easily generating a synthesis process, which is a treatment procedure of synthesizing a target material from starting materials, from a document. For example, a synthesis process which is graphable structured data can be easily generated from a synthesis process described in a natural language in a document. Thus, the synthesis process described in the document can be presented to a user in an easy-to-understand manner.

Analysis of Synthesis Process

Figure 12:
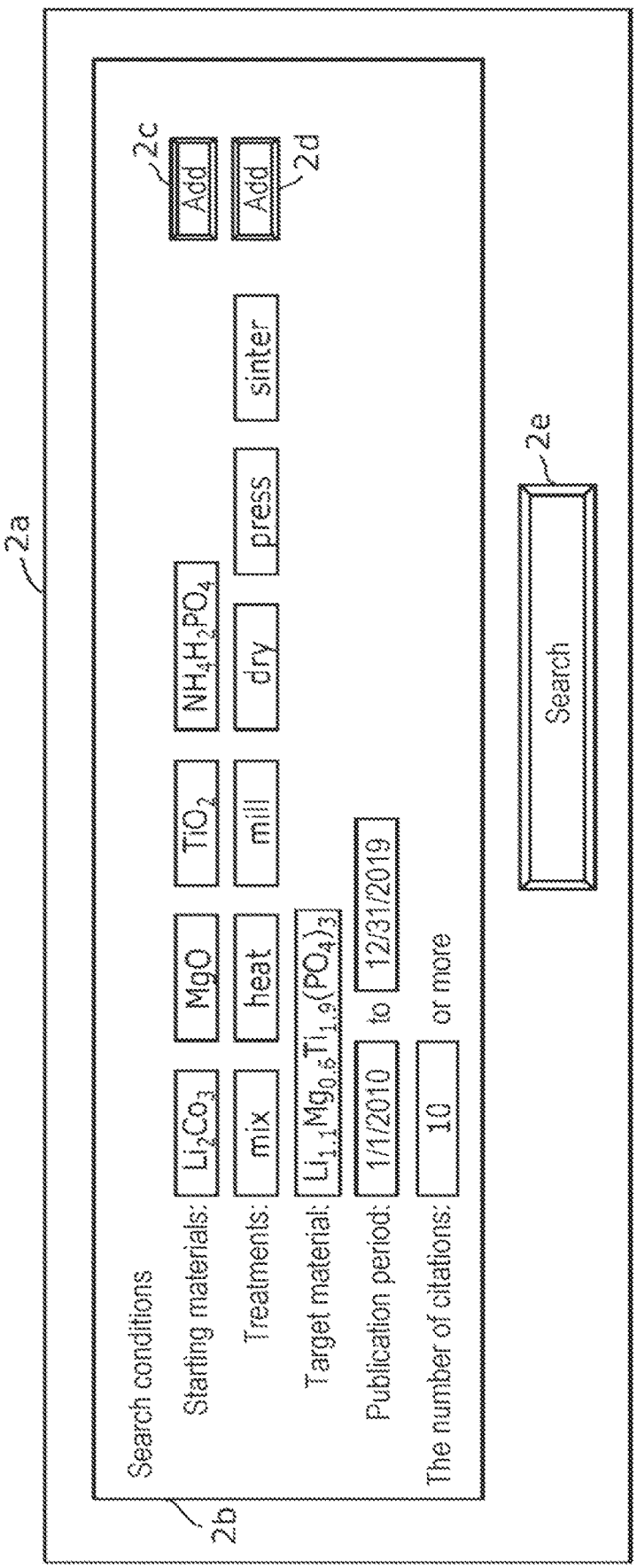
FIG. 12 is a diagram illustrating an example of a synthesis process search screen displayed on the display unit in the first embodiment.

FIG. 12 is a diagram illustrating an example of a synthesis process search screen displayed on the display unit 205.

The search unit 203 causes the display unit 205 to display, for example, a synthesis process search screen $2a$ illustrated in FIG. 12 in response to a signal indicating a user operation result output from the operation device 340.

The synthesis process search screen $2a$ includes a search condition window $2b$ and a search start button $2e$. The search condition window $2b$ includes input fields for inputting the names of starting materials (i.e., material words) and input fields for inputting the names of treatments (i.e., treatment words). The search condition window $2b$ also includes a material addition button 2c for adding an input field for a starting material and a treatment addition button 2d for adding an input field for a treatment. The search condition window 2b further includes an input field for inputting the name of a target material (i.e., a material word), an input field for inputting a publication period, and an input field for inputting the number of citations.

When the synthesis process search screen 2a is displayed, the user fills in each input field by operating the operation device 340. For example, as illustrated in FIG. 12, the user inputs material words "$Li_2CO_3$", "$MgO$", "$TiO_2$", and "$NH_4H_2PO_4$" to the four input fields for starting materials. If the input fields are insufficient, the user selects the material addition button 2c by operating the operation device 340. Accordingly, an input field for inputting the name of a starting material is added and displayed. Similarly, the user inputs treatment words "mix", "heat", "mill", "dry", "press" and "sinter" to the six input fields for treatments. If the input fields are insufficient, the user selects the treatment addition button 2d by operating the operation device 340. Accordingly, an input field for inputting the name of a treatment is added and displayed.

Furthermore, the user inputs a material word "$Li_{1.1}Mg_{0.6}Ti_{1.9}(PO_4)_3$" to the input field for a target material, inputs "1/1/2010" to "12/31/2019" to the input fields for a publication period, and inputs "10" or more to the input field for the number of citations.

Subsequently, the user selects the search start button 2e by operating the operation device 340. Accordingly, the search condition acceptance unit 202 accepts, as search conditions, the names of the starting materials, the names of the treatments, the name of the target material, the publication period, and the number of citations that have been input to the search condition window 2b. The search condition acceptance unit 202 outputs the search conditions to the search unit 203. Upon acquiring the search conditions from the search condition acceptance unit 202, the search unit 203 searches the synthesis processes accumulated in the synthesis process accumulation unit 201 for a synthesis process satisfying the search conditions. The search conditions may include a synthesis condition and a characteristic value.

In this way, the search unit 203 searches for n synthesis processes by using at least one of a treatment word, a synthesis condition, a characteristic value, or a set of material words. That is, the search unit 203 searches for the process information 1 to the process information n by using at least one of the treatment word i, the synthesis condition i, the characteristic value i, or a set of the material words. This makes it possible to search for and combine n synthesis processes to which at least one of a treatment word, a synthesis condition, a characteristic value, or a set of material words is common. The search unit 203 searches for n synthesis processes by further using bibliographic information. That is, the search unit 203 searches for the process information 1 to the process information n by further using bibliographic information. This makes it possible to search for and combine n synthesis processes to which a publication period or the like included in the bibliographic information is common.

Figure 13:
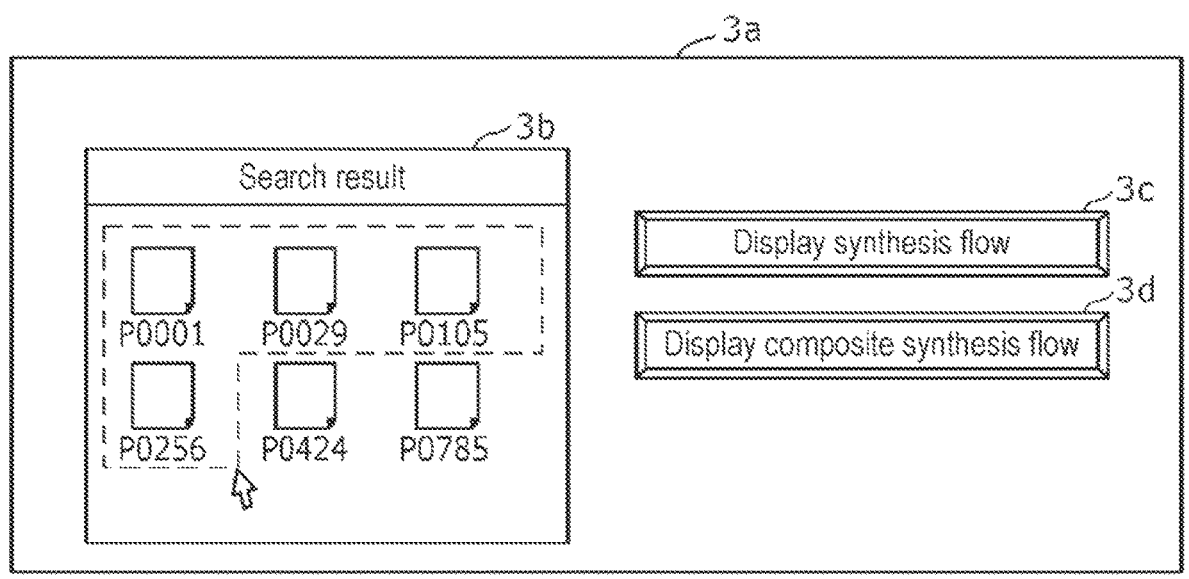
FIG. 13 is a diagram illustrating an example of a search result display screen displayed on the display unit in the first embodiment.

FIG. 13 is a diagram illustrating an example of a search result display screen displayed on the display unit 205.

After the search for a synthesis process has finished, the search unit 203 causes the display unit 205 to display a search result display screen 3a illustrated in FIG. 13.

The search result display screen 3a includes a search result window 3b, a first display button 3c, and a second display button 3d. On the search result window 3b, a list of synthesis processes found through the search performed by the search unit 203 is displayed. For example, a synthesis process having a name "P0001" generated from a document having a file name or a paper ID "0001" is displayed on the search result window 3b. The first display button 3c is a button for displaying a synthesis process as a synthesis flow, and the second display button 3d is a button for displaying a composite synthesis process as a composite synthesis flow. The composite synthesis flow is a flow obtained by graphing a composite synthesis process.

For example, the user selects the synthesis process having the name "P0001" displayed on the search result window 3b by operating the operation device 340. The user then selects the first display button 3c by operating the operation device 340. As a result, the search unit 203 causes the display unit 205 to display the synthesis process having the name "P0001" as a synthesis flow as illustrated in FIG. 9 or FIG. 10.

The user selects synthesis processes displayed on the search result window 3b by operating the operation device 340. For example, as illustrated in FIG. 13, the synthesis process having the name "P0001", a synthesis process having a name "P0029", a synthesis process having a name "P0105", and a synthesis process having a name "P0256" are selected. The user then selects the second display button 3d by operating the operation device 340. As a result, the search unit 203 outputs the four synthesis processes to the combining unit 204. The combining unit 204 combines the four synthesis processes to generate a composite synthesis process, and causes the display unit 205 to display the composite synthesis process as a composite synthesis flow.

In the example illustrated in FIG. 13, a composite synthesis process is generated from the synthesis processes selected by the user. Alternatively, a composite synthesis process may be automatically generated from synthesis processes found through a search and may be displayed. That is, the combining unit 204 may combine all the synthesis processes shown on the search result window 3b to generate a composite synthesis process.

The combining unit 204 does not generate a composite synthesis process if one synthesis process has been selected by the user or if one synthesis process has been found through a search. That is, if n synthesis processes have been found by the search unit 203 and if n is greater than or equal to 2, the combining unit 204 combines the n synthesis processes.

Figure 14A:
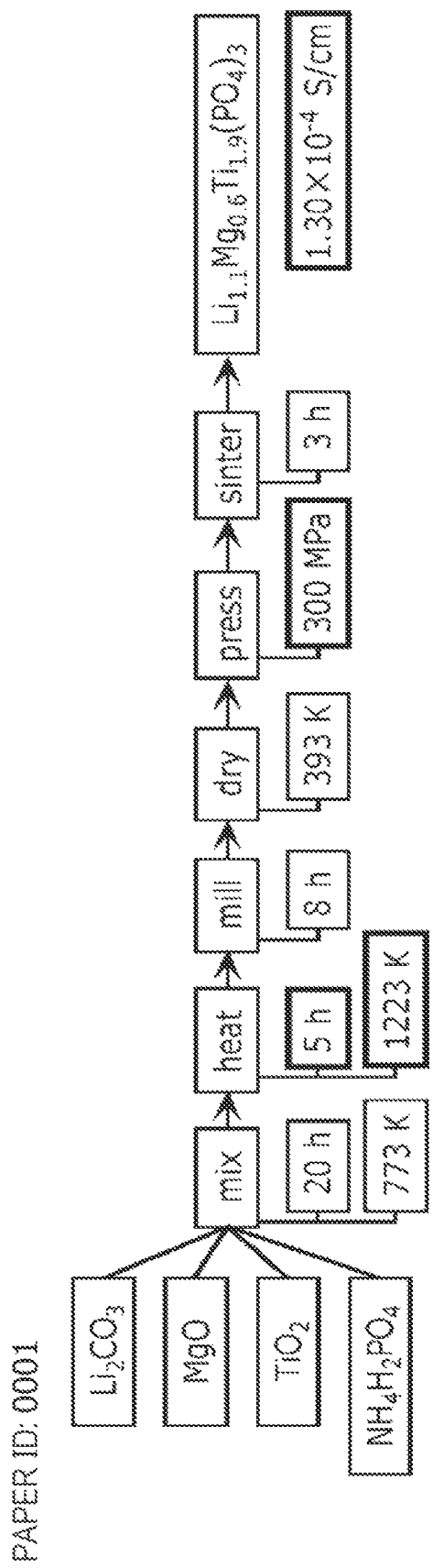
FIG. 14A is a diagram illustrating an example of a synthesis process to be combined in the first embodiment.
Figure 14B:
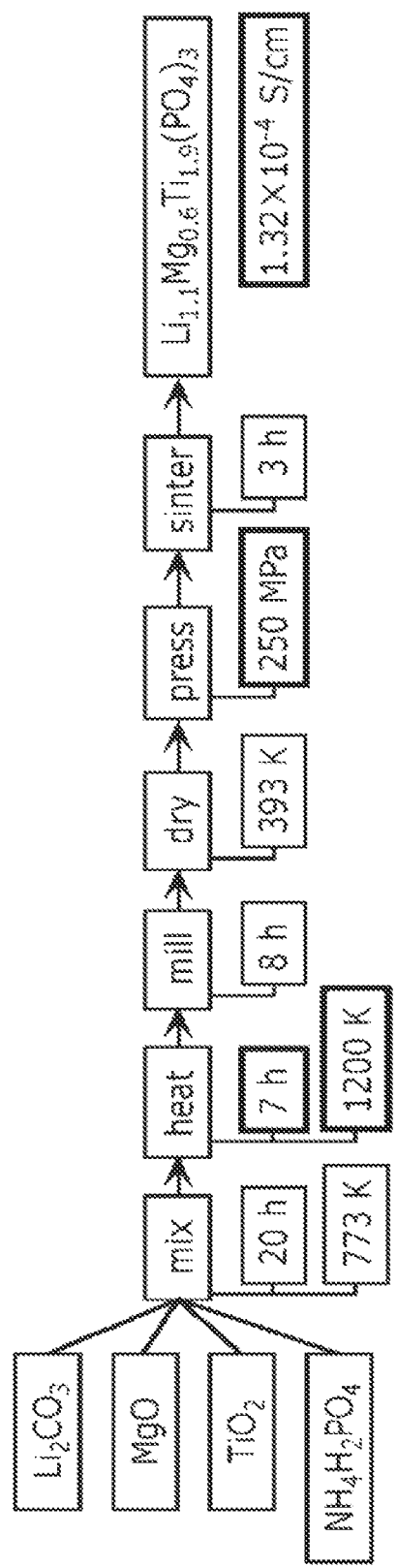
FIG. 14B is a diagram illustrating another example of a synthesis process to be combined in the first embodiment.
Figure 14C:
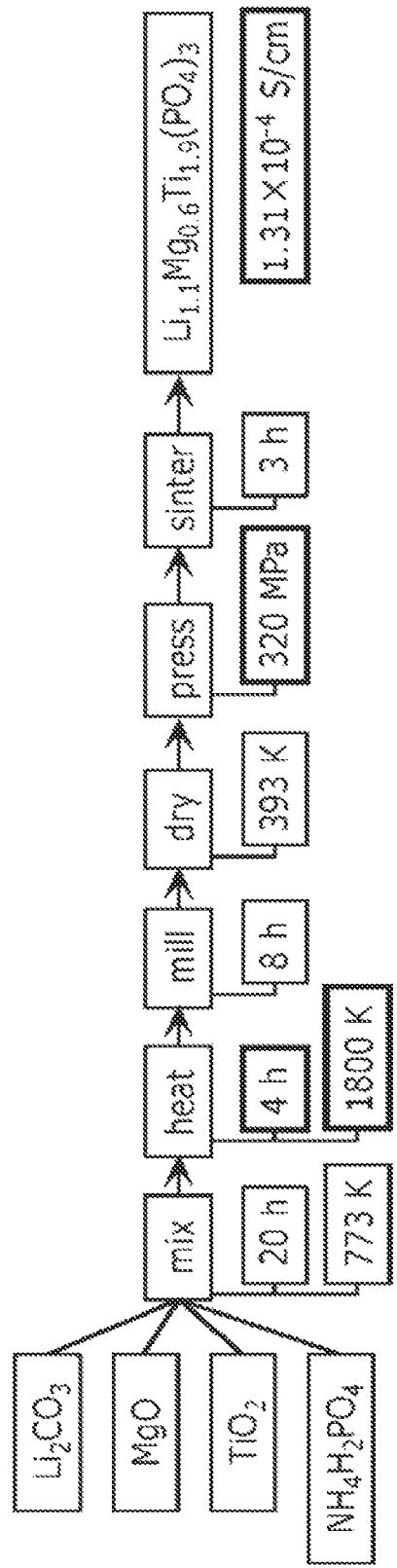
FIG. 14C is a diagram illustrating still another example of a synthesis process to be combined in the first embodiment.
Figure 14D:
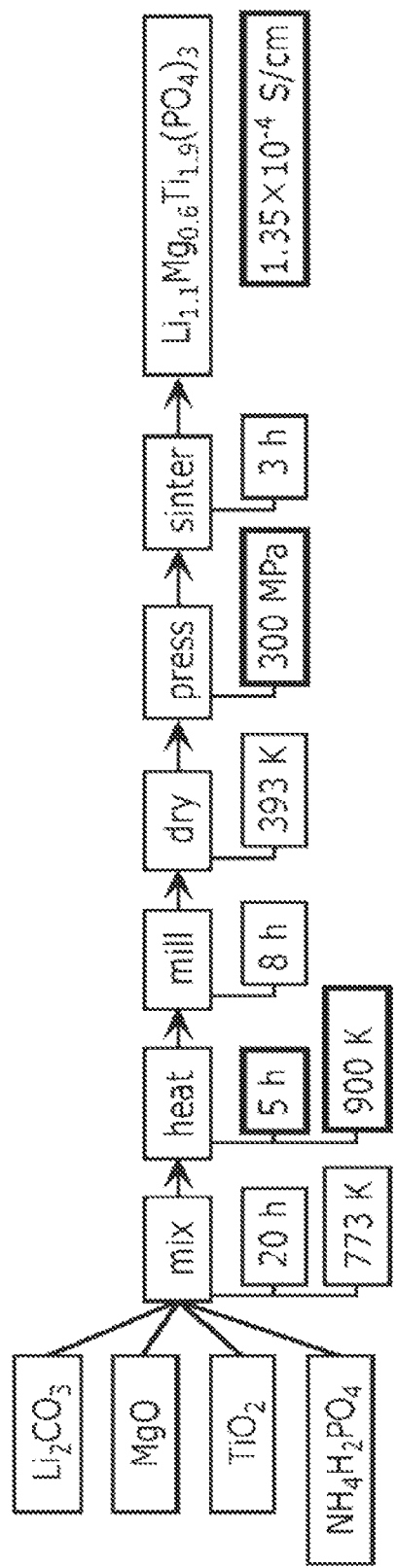
FIG. 14D is a diagram illustrating still another example of a synthesis process to be combined in the first embodiment.

Each of FIG. 14A to FIG. 14D is a diagram illustrating an example of a synthesis process to be combined. Specifically, FIG. 14A is a diagram illustrating, as a synthesis flow, a synthesis process generated from a document which is a paper having a paper ID "0001". FIG. 14B is a diagram illustrating, as a synthesis flow, a synthesis process generated from a document which is a paper having a paper ID "0029". FIG. 14C is a diagram illustrating, as a synthesis flow, a synthesis process generated from a document which is a paper having a paper ID "0105". FIG. 14D is a diagram illustrating, as a synthesis flow, a synthesis process generated from a document which is a paper having a paper ID "0256".

These four synthesis processes have a common part and different parts. In FIG. 14A to FIG. 14D, different parts are indicated by thick-line frames.

The common part corresponds to the search conditions. That is, the material words "$Li_2CO_3$", "$MgO$", "$TiO_2$" and "$NH_4H_2PO_4$" of the starting materials, the treatment words "mix", "heat", "mill", "dry", "press" and "sinter", and the material word "$Li_{1.1}Mg_{0.5}Ti_{1.9}(PO_4)_3$" of the target material are common to the four synthesis processes. In other words, the material words of the starting materials, the treatment words, and the material word of the target material are identical among the four synthesis processes. On the other hand, the synthesis conditions and the characteristic value of target material are different among the four synthesis processes. For example, the synthesis condition of time associated with the treatment indicated by the treatment word "heat" is different among the four synthesis processes, that is, "5 h", "7 h" and "4 h". Similarly, the synthesis condition of temperature associated with the treatment indicated by the treatment word "heat" is different among the four synthesis processes, that is, "1223 K", "1200 K", "1800 K", and "900 K". Furthermore, the synthesis condition of pressure associated with the treatment indicated by the treatment word "press" is different among the four synthesis processes, that is, "300 MPa", "250 MPa", and "320 MPa". Also, the characteristic value of the target material is different among the four synthesis processes, that is, "$1.30 \times 10^{-4}$ S/cm", "$1.32 \times 10^{-4}$ S/cm", "$1.31 \times 10^{-4}$ S/cm", and "$1.35 \times 10^{-4}$ S/cm".

The combining unit 204 combines these four synthesis processes to generate a composite synthesis process that indicates the part common to the four synthesis processes and that comprehensively indicates the parts different among the four synthesis processes.

FIG. 15 is a diagram for describing processing performed by the combining unit 204.

The combining unit 204 merges the parts different among the above-described four synthesis processes. For example, the combining unit 204 merges the synthesis conditions of time "5 h", "7 h", and "4 h" associated with the treatment word "heat" common to the four synthesis processes, thereby generating a comprehensive synthesis condition of time "4-7 h". Similarly, the combining unit 204 merges the synthesis conditions of temperature associated with the treatment word "heat" common to the four synthesis processes, thereby generating a comprehensive synthesis condition of temperature "900-1800 K". Furthermore, the combining unit 204 merges the synthesis conditions of pressure associated with the treatment word "press" common to the four synthesis processes, thereby generating a comprehensive synthesis condition of pressure "250-320 MPa". Furthermore, the combining unit 204 merges the characteristic values of the four synthesis processes, thereby generating a comprehensive characteristic value "$1.30 \times 10^{-4}$-$1.35 \times 10^{-4}$ S/cm".

As described above, in the present embodiment, in a case where synthesis conditions different from each other indicate numerical values different from each other, the combining unit 204 generates, as a comprehensive synthesis condition, a numerical value range defined by a minimum value and a maximum value among the numerical values different from each other. That is, in the present embodiment, in a case where a synthesis condition 1 to a synthesis condition n different from each other indicate a numerical value 1 to a numerical value n different from each other, respectively, the combining unit 204 generates, as a comprehensive synthesis condition, a numerical value range defined by a minimum value and a maximum value among the numerical value 1 to the numerical value n different from each other in the generation of the comprehensive synthesis condition. In other words, in a case where treatment words among a treatment word 1 to a treatment word n are identical to each other, the combining unit 204 generates a comprehensive synthesis condition including synthesis conditions corresponding to the treatment words from the synthesis condition 1 to the synthesis condition n, and replaces the synthesis conditions with the comprehensive synthesis condition to generate composite process information. The comprehensive synthesis condition indicates a range from a numerical value p to a numerical value q in the following case. The case is a case in which the synthesis condition 1 to the synthesis condition n different from each other indicate the numerical value 1 to the numerical value n different from each other, respectively, and among the numerical value 1 to the numerical value n, the minimum numerical value is the numerical value p, the maximum numerical value is the numerical value q, and the numerical values p and q satisfy $1 \leq p \leq n$, $1 \leq q \leq n$, and $p \neq q$.

In addition, in the present embodiment, in a case where the above-described different parts include synthesis conditions different from each other and associated with a treatment word common to the four synthesis processes, the combining unit 204 generates a comprehensive synthesis condition comprehensively indicating the different synthesis conditions. The combining unit 204 then replaces, with the comprehensive synthesis condition, the synthesis condition included in any one target synthesis process to be replaced among the four synthesis processes and associated with the common treatment word, thereby generating a composite synthesis process. That is, in the present embodiment, in a case where the synthesis condition 1 to the synthesis condition n different from each other and associated with the treatment word i common to the pieces of process information are the above-described different parts, the combining unit 204 generates a comprehensive synthesis condition including the synthesis condition 1 to the synthesis condition n different from each other. The combining unit 204 then replaces, with the comprehensive synthesis condition, the synthesis condition i included in the process information i and associated with the common treatment word i, thereby generating composite process information.

In the present embodiment, in a case where the above-described common part includes the material word of the target material common to the four synthesis processes, and the above-described different parts include characteristic values different from each other among the four synthesis processes, the combining unit 204 further generates a comprehensive characteristic value comprehensively indicating the characteristic values different from each other. The combining unit 204 then replaces, with the comprehensive characteristic value, the characteristic value included in the above-described target synthesis process to be replaced. That is, in the present embodiment, in a case where the above-described common part includes a target material word common to pieces of process information, and the above-described different parts include a characteristic value 1 to a characteristic value n different from each other among the pieces of process information, the combining unit 204 further generates a comprehensive characteristic value including the characteristic value 1 to the characteristic value n different from each other and replaces the characteristic value i included in the process information i with the comprehensive characteristic value.

For example, the combining unit 204 selects the synthesis process of the paper ID "0001" as a target synthesis process to be replaced, replaces the synthesis condition included in the target synthesis process with the comprehensive synthesis condition, and replaces the characteristic value included in the target synthesis process with the comprehensive characteristic value. Accordingly, a composite synthesis process is generated in which a part common to the four synthesis processes is indicated and parts different from each other among the four synthesis processes are comprehensively indicated.

Figure 16:
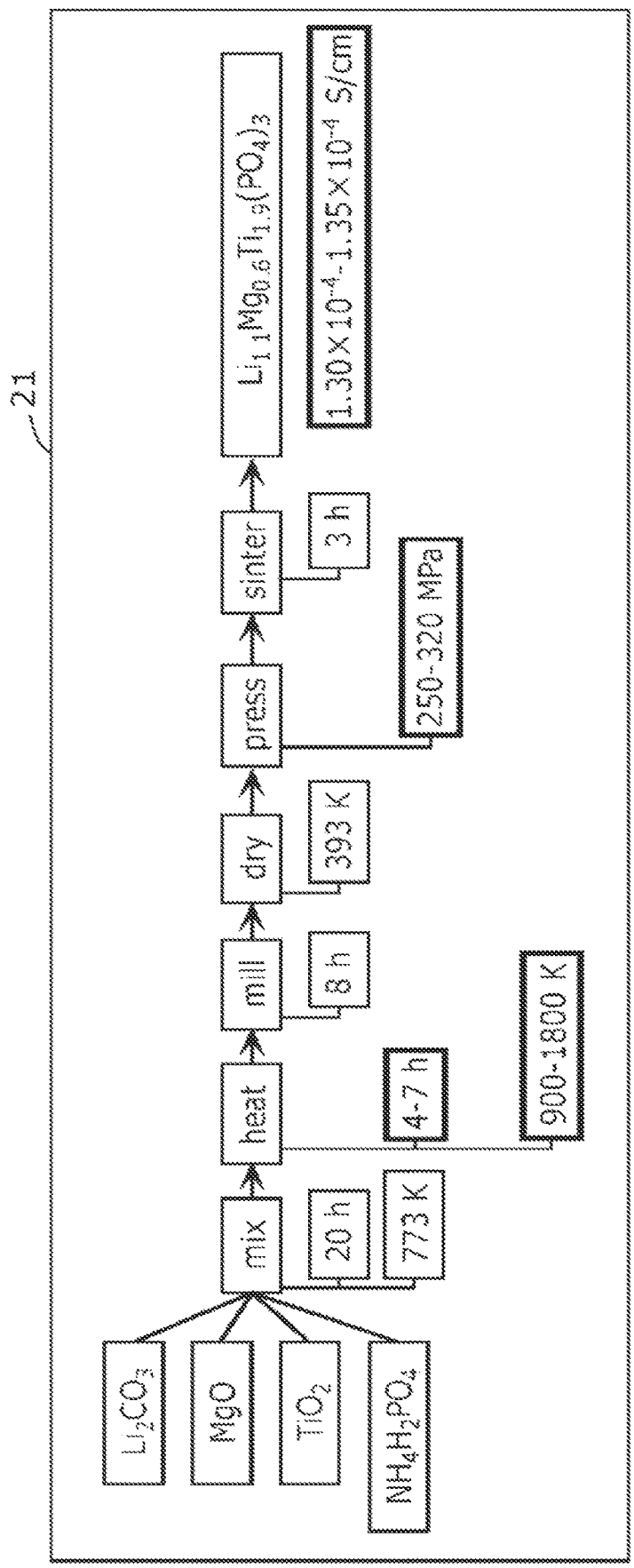
FIG. 16 is a diagram illustrating an example of a composite screen displayed on the display unit in the first embodiment.

FIG. 16 is a diagram illustrating an example of a composite screen displayed on the display unit 205.

After generating the composite synthesis process in the above-described manner, the combining unit 204 causes the display unit 205 to display, for example, a composite screen 21 illustrated in FIG. 16.

On the composite screen 21, a composite synthesis process generated by the combining unit 204 is graphed and displayed. That is, a composite synthesis flow is displayed. For example, in the composite synthesis flow illustrated in FIG. 16, the synthesis conditions "5 h", "1223 K", and "300 MPa" included in the synthesis process of the paper ID "0001" have been replaced with comprehensive synthesis conditions "4-7 h", "900-1800 K", and "250-320 MPa", respectively. Furthermore, in the composite synthesis flow illustrated in FIG. 16, the characteristic value "$1.30 \times 10^{-4}$ S/cm" included in the synthesis process of the paper ID "0001" has been replaced with a comprehensive characteristic value "$1.30 \times 10^{-4}$-$1.35 \times 10^{-4}$ S/cm".

In the composite synthesis flow illustrated in FIG. 16, the comprehensive synthesis conditions and the comprehensive characteristic value are displayed in a manner different from the other synthesis conditions, the treatment words, and the material words. For example, the color, thickness, size, or shape of frames surrounding the comprehensive synthesis conditions and the comprehensive characteristic value may be different from that of frames surrounding the other synthesis conditions and so forth. Alternatively, the color, size, or shape of display regions of the comprehensive synthesis conditions and the comprehensive characteristic value may be different from that of display regions of the other synthesis conditions and so forth. Accordingly, the comprehensive synthesis conditions and the comprehensive characteristic value can be presented to the user in an easy-to-understand manner in distinction from the other synthesis conditions and so forth.

As described above, in the present embodiment, the synthesis conditions used in individual documents are collectively displayed as a comprehensive synthesis condition, and thus a synthesis process for a new material can be easily searched for by viewing the comprehensive synthesis condition. In the present embodiment, even if the synthesis conditions used in individual documents are different and thus the characteristic values of the target material are different, these characteristic values are collectively displayed as a comprehensive characteristic value, and thus a synthesis process for a new material can be easily searched for by viewing the comprehensive characteristic value.

Processing Operation

Figure 17A:
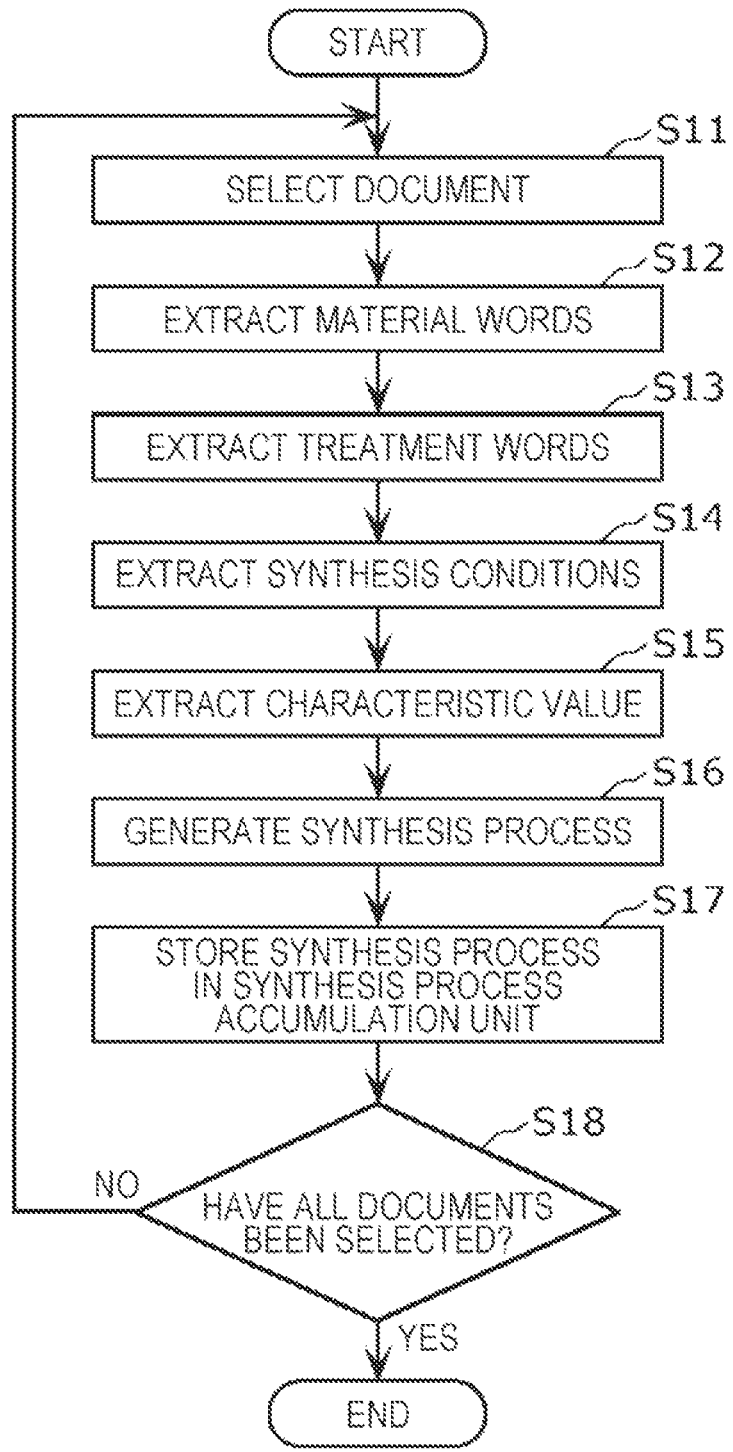
FIG. 17A is a flowchart illustrating an example of a processing operation performed by the synthesis process generation apparatus in the first embodiment.

FIG. 17A is a flowchart illustrating an example of a processing operation performed by the synthesis process generation apparatus 100 in the present embodiment.

First, the document selection unit 101 selects one document as an extraction-target document from among the documents accumulated in the document accumulation unit 102 (step S11).

Subsequently, the material word extraction unit 103 extracts material words from the extraction-target document by using the material word dictionary illustrated in part (a) of FIG. 3A (step S12). The treatment word extraction unit 104 extracts treatment words from the extraction-target document by using the treatment word dictionary illustrated in part (b) of FIG. 3A (step S13). The condition extraction unit 105 extracts synthesis conditions from the extraction-target document by using the condition word dictionary illustrated in part (a) of FIG. 3B (step S14). The characteristic value extraction unit 106 extracts a characteristic value of a target material from the extraction-target document by using the characteristic value dictionary illustrated in part (b) of FIG. 3B (step S15). Steps S12 to S15 may be performed in any order or may be performed in parallel.

Subsequently, the generation unit 107 associates the extracted material words, treatment words, synthesis conditions, and characteristic value with each other to generate a synthesis process (step S16). Furthermore, the generation unit 107 stores the generated synthesis process in the synthesis process accumulation unit 201 (step S17).

Subsequently, the document selection unit 101 determines whether all the documents accumulated in the document accumulation unit 102 have been selected as an extraction-target document (step S18). If it is determined that all the documents have not been selected (NO in step S18), the document selection unit 101 repeatedly executes step S11. That is, the document selection unit 101 selects, as an extraction-target document, a document that has not yet been selected from among the documents accumulated in the document accumulation unit 102. On the other hand, if the document selection unit 101 determines that all the documents have been selected (YES in step S18), the synthesis process generation apparatus 100 ends the synthesis process generation processing.

Figure 17B:
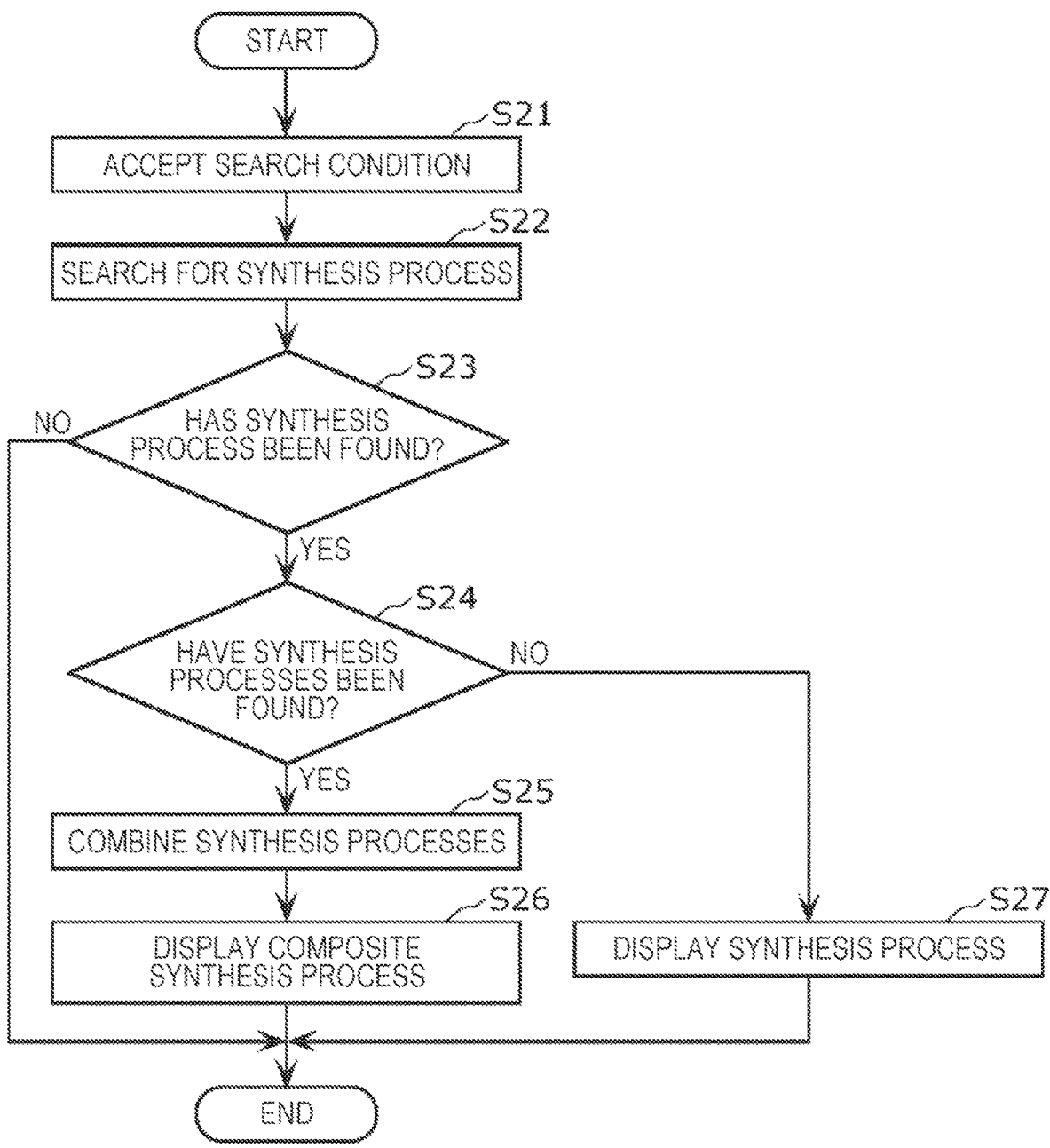
FIG. 17B is a flowchart illustrating an example of a processing operation performed by a synthesis process analysis apparatus in the first embodiment.

FIG. 17B is a flowchart illustrating an example of a processing operation performed by the synthesis process analysis apparatus 200 in the present embodiment.

First, the search condition acceptance unit 202 accepts a search condition corresponding to a signal indicating a user operation result output from the operation device 340 (step S21). Subsequently, the search unit 203 searches the synthesis processes accumulated in the synthesis process accumulation unit 201 for a synthesis process satisfying the search condition (step S22). Subsequently, the search unit 203 determines whether a synthesis process satisfying the search condition has been found through the search in step S22 (step S23). If the search unit 203 determines that a synthesis process satisfying the search condition has not been found (NO in step S23), the synthesis process analysis apparatus 200 ends the synthesis process analysis processing. On the other hand, if the search unit 203 determines that a synthesis process satisfying the search condition has been found (YES in step S23), the search unit 203 further determines whether synthesis processes have been found (step S24). If the search unit 203 determines that the number of synthesis processes that have been found is not two or more but is one (NO in step S24), the search unit 203 causes the display unit 205 to display the synthesis process as a synthesis flow in response to a user operation (step S27). On the other hand, if the search unit 203 determines that the number of synthesis processes that have been found is two or more (YES in step S24), the combining unit 204 combines the found synthesis processes in response to a user operation (step S25). Subsequently, the combining unit 204 causes the display unit 205 to display a composite synthesis process generated through the combining as a composite synthesis flow (step S26).

As described above, in the present embodiment, a synthesis process, which is a treatment procedure of synthesizing a target material from starting materials, can be easily generated from a document. A composite synthesis process is generated from generated synthesis processes, and thus a common part and different parts of the many synthesis processes can be displayed in an easy-to-understand manner.

Accordingly, a search for a synthesis process for a new material can be appropriately supported. In a case where synthesis processes respectively generated from the latest documents are combined together, the knowledge about material development can be kept up-to-date. In addition, by using an enormous number of documents, a search for a synthesis process covering a wide range of materials can be supported.

In the present embodiment, the synthesis processes generated by the generation unit 107 and the composite synthesis process generated by the combining unit 204 are each configured to be graphable. The display unit 205 displays the composite synthesis process generated by the combining unit 204 in a graph format. That is, in the present embodiment, the pieces of process information generated by the generation unit 107 and the composite process information generated by the combining unit 204 are each configured to be graphable. The display unit 205, which is an example of an outputter, displays the composite process information generated by the combining unit 204 in a graph format.

Accordingly, because the synthesis processes are configured as graphable structured data, the composite synthesis process can also be easily generated as graphable structured data. Furthermore, the composite synthesis process is displayed in a graph format such as a flowchart, and thus the user can appropriately grasp the composite synthesis process.

First Modification

In the first embodiment described above, a composite synthesis flow indicates the material words of starting materials, treatment words, and synthesis conditions in a similar manner. In the present modification, the material words of starting materials, treatment words, and synthesis conditions are indicated in different manners.

Figure 18:
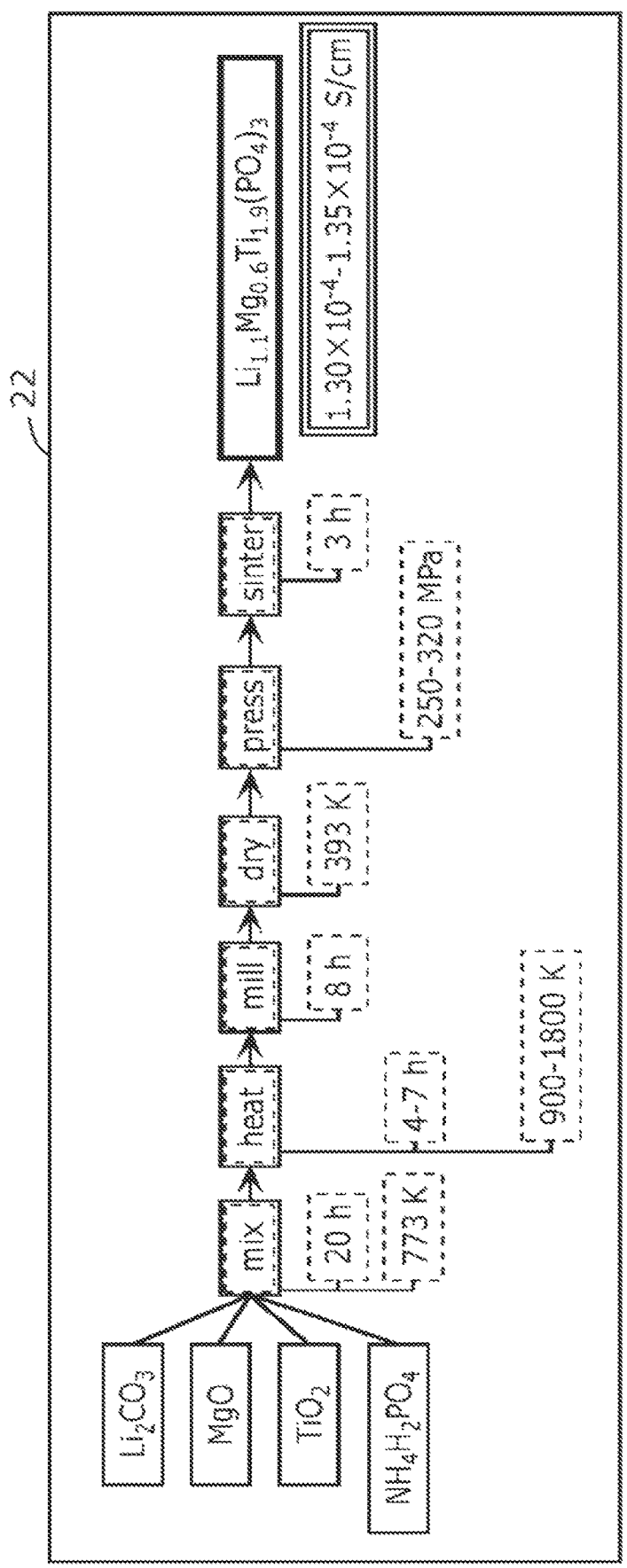
FIG. 18 is a diagram illustrating an example of a composite screen displayed on the display unit according to a first modification of the first embodiment.

FIG. 18 is a diagram illustrating an example of a composite screen displayed on the display unit 205 according to the present modification.

After generating a composite synthesis process in the above-described manner, the combining unit 204 according to the present modification causes the display unit 205 to display a composite screen 22 illustrated in FIG. 18 instead of the composite screen 21 illustrated in FIG. 16, for example.

On the composite screen 22, the composite synthesis process generated by the combining unit 204 is displayed as a composite synthesis flow. In the composite synthesis flow according to the present modification, the material words of starting materials, the material word of a target material, treatment words, synthesis conditions, and a characteristic value are displayed in different manners. For example, as illustrated in FIG. 18, the material words of starting materials are surrounded by solid-line frames, the treatment words are surrounded by double frames of a solid line and a broken line, the synthesis conditions are surrounded by broken-line frames, the material word of a target material is surrounded by a thick-solid-line frame, and the characteristic value is surrounded by a solid-line double frame. In this way, the material words of starting materials, the material word of a target material, the treatment words, the synthesis conditions, and the characteristic value may be surrounded by different types of frames. Alternatively, the material words of starting materials, the material word of a target material, the treatment words, the synthesis conditions, and the characteristic value may be different from each other in the color, size, or shape of the display regions.

Accordingly, the material words of starting materials, the material word of a target material, the treatment words, the synthesis conditions, and the characteristic value can be distinguished from each other and presented to the user in an easy-to-understand manner.

Second Modification

In the first embodiment described above, a comprehensive synthesis condition is generated by merging all synthesis conditions different from each other. In the present modification, merging is performed on each of subsets of synthesis conditions by clustering, instead of merging all the synthesis conditions.

FIG. 19 is a diagram for describing processing performed by the combining unit 204 according to the present modification.

When synthesis conditions different from each other indicate numerical values different from each other, the combining unit 204 according to the present modification performs clustering on a set including the numerical values different from each other to generate subsets, and generates a comprehensive synthesis condition from each of the subsets. That is, in the present modification, when the synthesis condition 1 to the synthesis condition n different from each other indicate the numerical value 1 to the numerical value n different from each other, respectively, the combining unit 204 performs clustering on a set including the numerical value 1 to the numerical value n different from each other to generate subsets, and generates a comprehensive synthesis condition from each of the subsets.

For example, as illustrated in FIG. 19, six synthesis processes are found through a search performed by the search unit 203. Here, the synthesis conditions of pressure associated with the treatment word "press" are different from each other among the six synthesis processes, that is, "300 MPa", "250 MPa", "320 MPa", "450 MPa", and "460 MPa". At this time, the combining unit 204 performs clustering on a set including the different pressure values to generate two subsets. An existing method (for example, a k-means method) is used for clustering. As a result, a first subset including "300 MPa", "250 MPa", and "320 MPa" and a second subset including "450 MPa" and "460 MPa" are generated. In FIG. 19, the first subset is indicated by a chain-line frame, and the second subset is indicated by a broken-line frame. The combining unit 204 generates a comprehensive synthesis condition of pressure "250-320 MPa" from the first subset, and generates a comprehensive synthesis condition of pressure "450-460 MPa" from the second subset.

In addition, the combining unit 204 generates a comprehensive characteristic value "$1.30 \times 10^{-4}$-$1.35 \times 10^{-4}$ S/cm" from the characteristic values corresponding to the first subset, and generates a comprehensive characteristic value "$1.41 \times 10^{-4}$-$1.42 \times 10^{-4}$ S/cm" from the characteristic values corresponding to the second subset.

The combining unit 204 then selects, for example, the synthesis process of the paper ID "0001" as a target synthesis process to be replaced, replaces the synthesis condition included in the target synthesis process with the two comprehensive synthesis conditions, and replaces the characteristic value included in the target synthesis process with the two comprehensive characteristic values. Accordingly, a composite synthesis process is generated in which a part common to the six synthesis processes is indicated and parts different from each other among the six synthesis processes are collectively indicated.

Figure 20A:
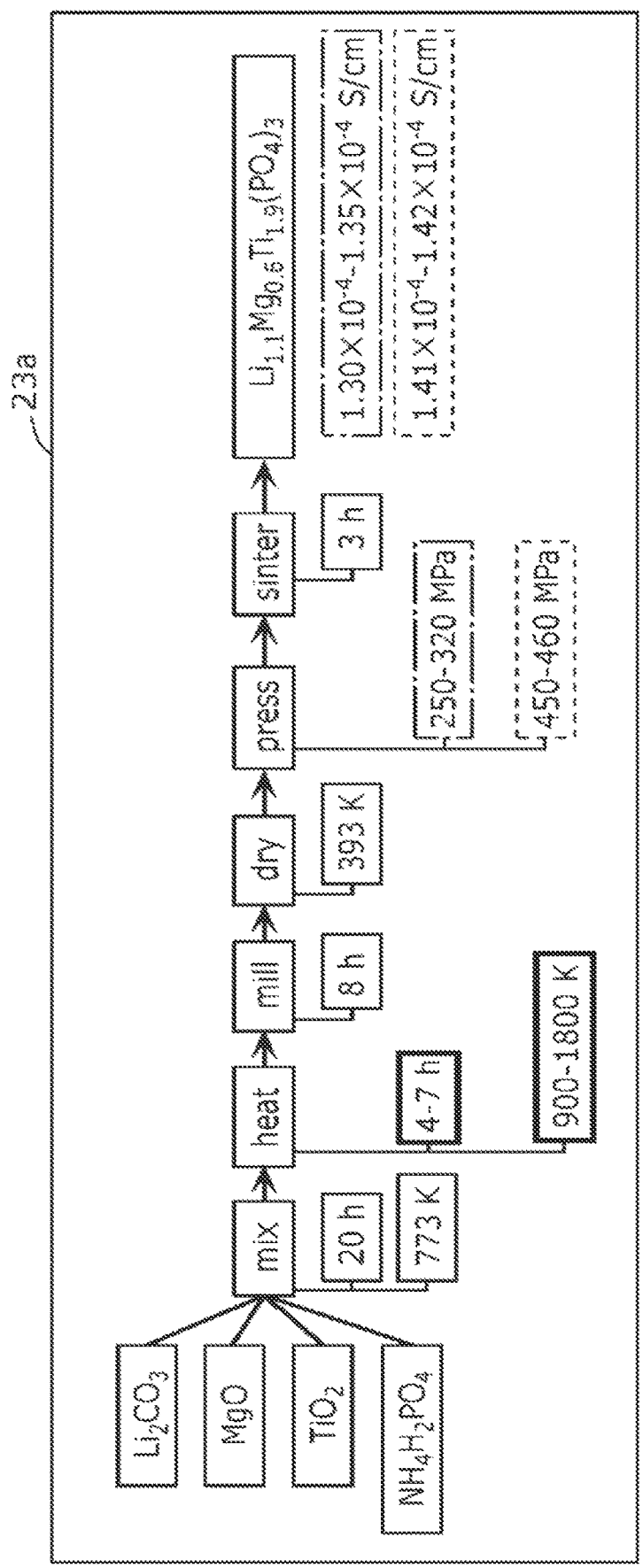
FIG. 20A is a diagram illustrating an example of a composite screen displayed on the display unit according to the second modification of the first embodiment.

FIG. 20A is a diagram illustrating an example of a composite screen displayed on the display unit 205 according to the present modification.

After generating the composite synthesis process in the above-described manner, the combining unit 204 causes the display unit 205 to display, for example, a composite screen 23a illustrated in FIG. 20A. On the composite screen 23a, the composite synthesis process generated by the combining unit 204 is displayed as a composite synthesis flow.

For example, in the composite synthesis flow illustrated in FIG. 20A, the synthesis condition of pressure "300 MPa" included in the synthesis process of the paper ID "0001" has been replaced with the comprehensive synthesis conditions "250-320 MPa" and "450-460 MPa". Furthermore, in the composite synthesis flow illustrated in FIG. 20A, the characteristic value "$1.30 \times 10^{-4}$ S/cm" included in the synthesis process of the paper ID "0001" has been replaced with the comprehensive characteristic values "$1.30 \times 10^{-4}$-$1.35 \times 10^{-4}$ S/cm" and "$1.41 \times 10^{-4}$-$1.42 \times 10^{-4}$ S/cm".

For example, when synthesis conditions are slightly different from each other, all the synthesis conditions may be merged to generate a comprehensive synthesis condition, as in the first embodiment described above. However, when the synthesis conditions are largely different from each other, clustering is performed as in the present modification to generate comprehensive synthesis conditions, and thus it becomes easy to find a synthesis condition that has not yet been used.

Figure 20B:
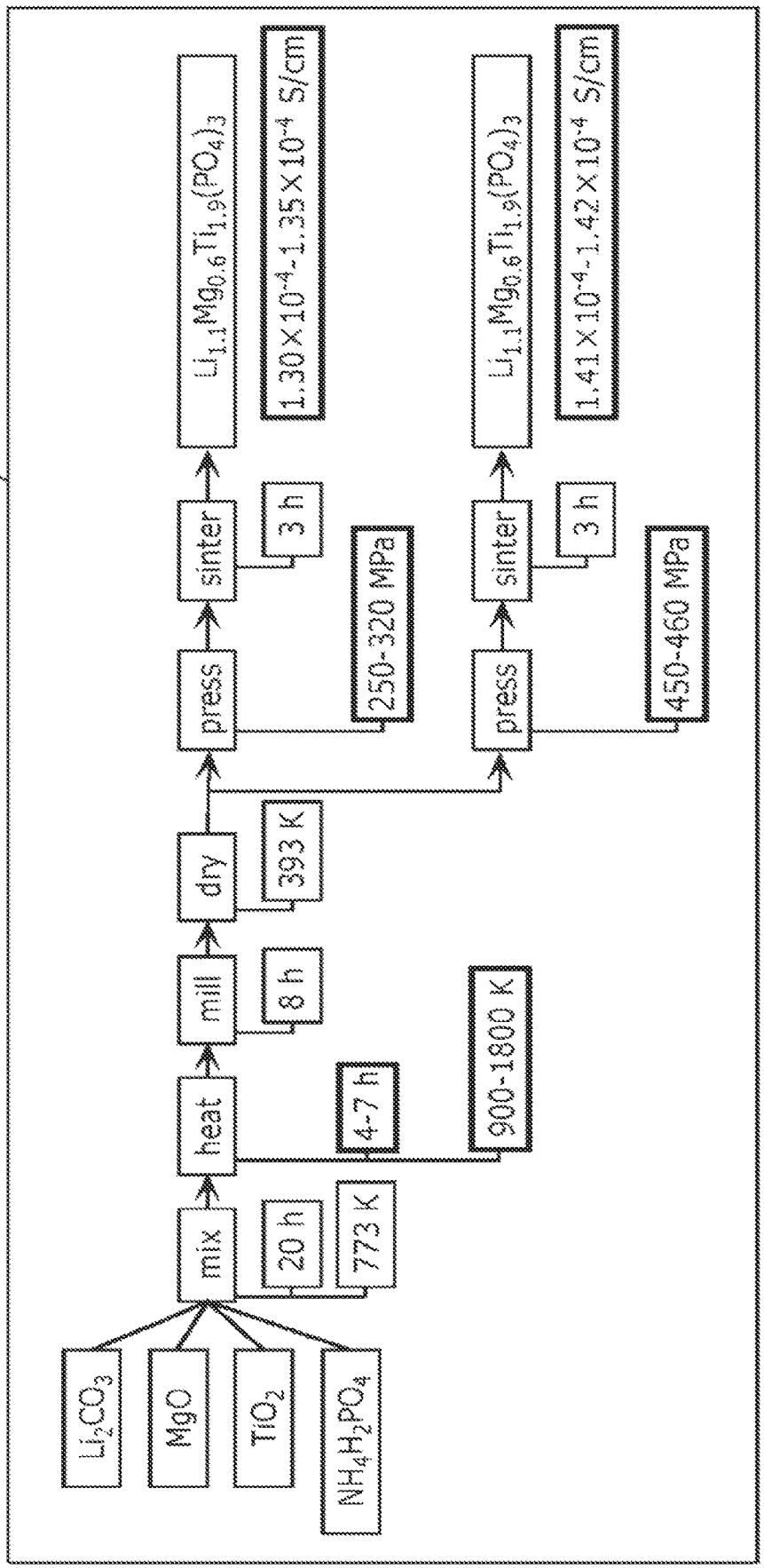
FIG. 20B is a diagram illustrating another example of a composite screen displayed on the display unit according to the second modification of the first embodiment.

FIG. 20B is a diagram illustrating another example of a composite screen displayed on the display unit 205 according to the present modification.

After generating the composite synthesis process in the above-described manner, the combining unit 204 may cause the display unit 205 to display, for example, a composite screen 23b illustrated in FIG. 20B. On the composite screen 23b, the composite synthesis process generated by the combining unit 204 is displayed as a composite synthesis flow.

For example, the composite synthesis flow illustrated in FIG. 20B branches into two routes from the treatment word "dry". That is, two branch flows are connected to the treatment indicated by the treatment word "dry". The two branch flows each include the treatment word "press" or "sinter" and the material word "$Li_{1.1}Mg_{0.6}Ti_{1.9}(PO_4)_3$" of the target material. The comprehensive synthesis condition "250-320 MPa" is associated with the treatment indicated by the treatment word "press" included in a first branch flow of the two branch flows, and the comprehensive synthesis condition "450-460 MPa" is associated with the treatment indicated by the treatment word "press" included in a second branch flow. Furthermore, the comprehensive characteristic value "$1.30 \times 10^{-4}$-$1.35 \times 10^{-4}$ S/cm" is associated with the material word "$Li_{1.1}Mg_{0.6}Ti_{1.9}(PO_4)_3$" of the target material included in the first branch flow. The comprehensive characteristic value "$1.41 \times 10^{-4}$-$1.42 \times 10^{-4}$ S/cm" is associated with the material word "$Li_{1.1}Mg_{0.6}Ti_{1.5}(PO_4)_3$" of the target material included in the second branch flow.

Accordingly, it can be determined that there are two types of synthesis processes in the documents obtained through the search, and it becomes possible to check the characteristic values of the target material for the respective synthesis processes.

As described above, in the present modification, comprehensive synthesis conditions are generated by clustering, and thus the tendency of synthesis conditions used in individual documents can be grasped in more detail.

Third Modification

In the first embodiment described above, synthesis processes to which all treatment words are common are combined to generate a composite synthesis process. In the present modification, synthesis processes having different treatment words are combined to generate a composite synthesis process.

Figure 21A:
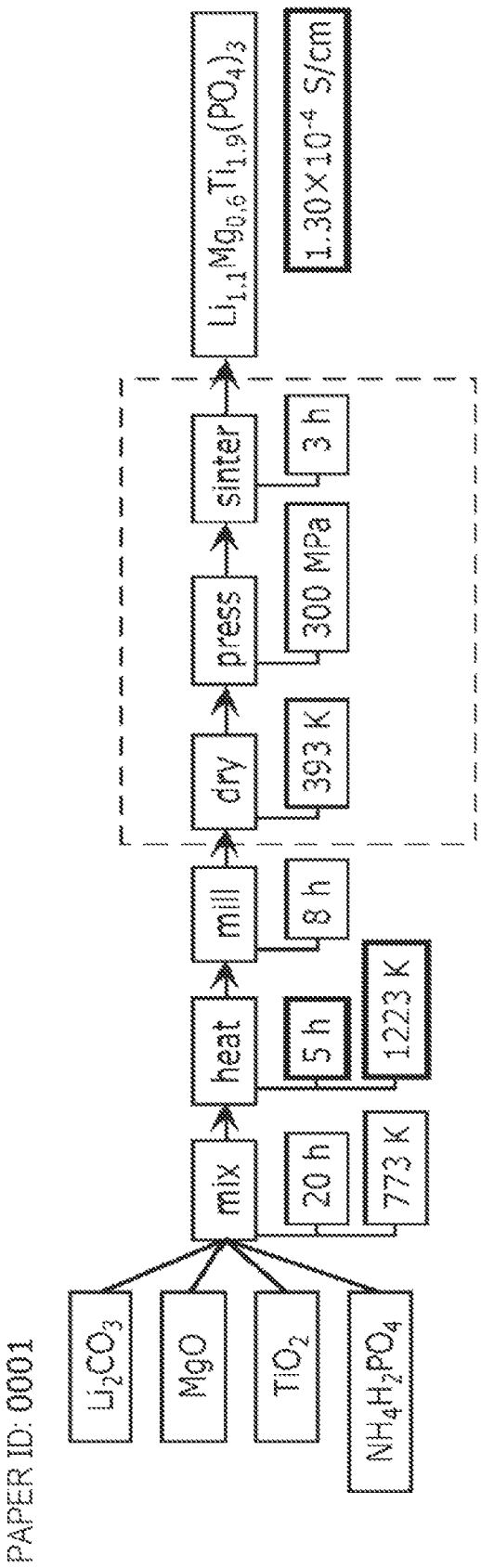
FIG. 21A is a diagram illustrating an example of a synthesis process to be combined in a third modification of the first embodiment.
Figure 21B:
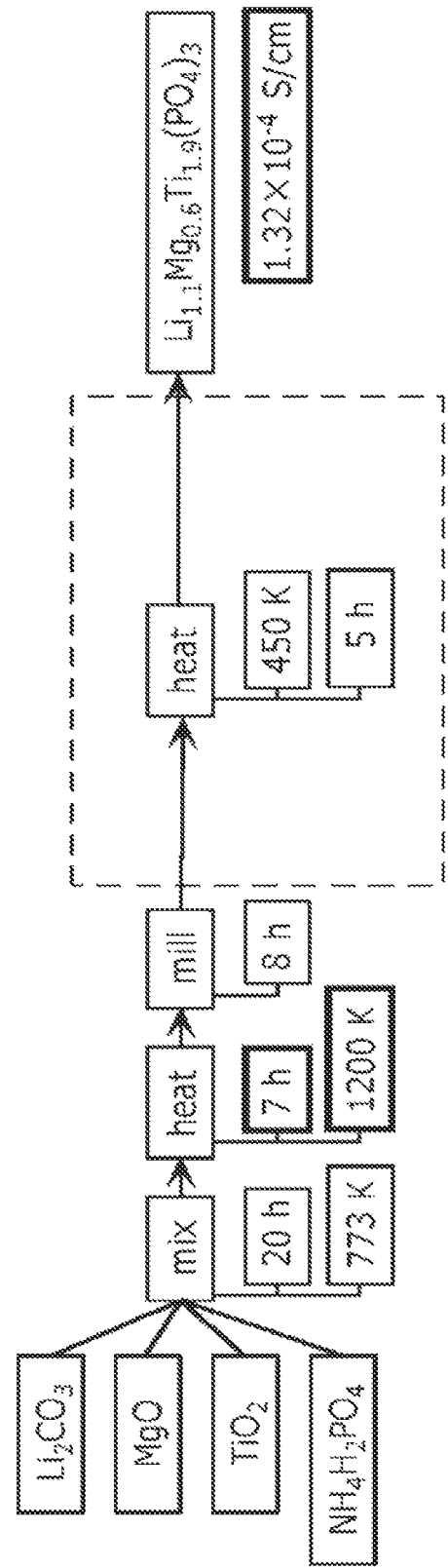
FIG. 21B is a diagram illustrating an example of a synthesis process to be combined in the third modification of the first embodiment.

FIG. 21A and FIG. 21B are each a diagram illustrating an example of a synthesis process to be combined in the present modification. For example, when the synthesis process search screen 2a illustrated in FIG. 12 is displayed on the display unit 205, the user selects the search start button 2e without inputting the names of treatments (that is, treatment words) to the treatment input fields. That is, a search for a synthesis process is started, with the material words "$Li_2CO_3$", "MgO", "$TiO_2$", and "$NH_4H_2PO_4$" of starting materials, the material word "$Li_{1.1}Mg_{0.6}Ti_{1.9}(PO_4)_3$" of a target material, the publication period "1/1/2010" to "12/31/2019", and the number of citations "10" or more being used as search conditions.

The search finds, for example, the synthesis process of the paper ID "0001" illustrated in the FIG. 21A and the synthesis process of the paper ID "0142" illustrated in FIG. 21B.

In these synthesis processes, the starting materials and the target material are the same. However, the treatments are different from each other. That is, the synthesis process of the paper ID "0001" includes treatment words "mix", "heat", "mill", "dry", "press", and "sinter", whereas the synthesis process of the paper ID "0142" includes treatment words "mix", "heat", "mill", and "heat". In other words, the synthesis process of the paper ID "0001" and the synthesis process of the paper ID "0142" include the treatment words "mix", "beat", and "mill" that are common to both the synthesis processes, and also include treatment words different from each other. The treatment words "dry", "press", and "sinter" included in the synthesis process of the paper ID "0001" are different from the treatment word "heat" included in the synthesis process of the paper ID "0142".

In addition, the synthesis process of the paper ID "0001" and the synthesis process of the paper ID "0142" include a common treatment word "heat". However, the two synthesis processes are different from each other in the synthesis conditions associated with the common treatment word "heat". That is, in the synthesis process of the paper ID "0001", the synthesis conditions are "5 h" and "1223 K", whereas in the synthesis process of the paper ID "0142", the synthesis conditions are "7 h" and "1200 K". Thus, the combining unit 204 merges these synthesis conditions different from each other.

FIG. 22 is a diagram for describing processing performed by the combining unit 204.

The combining unit 204 merges the synthesis conditions different from each other between the above-described two synthesis processes. For example, the combining unit 204 merges the synthesis conditions of time "5 h" and "7 h" associated with the treatment word "heat" common to the two synthesis processes, thereby generating a comprehensive synthesis condition of time "5-7 h". Similarly, the combining unit 204 merges the synthesis conditions of temperature associated with the common treatment word "heat", thereby generating a comprehensive synthesis condition of temperature "1200-1223 K".

The combining unit 204 according to the present modification generates a composite synthesis process including the above-described comprehensive synthesis conditions and also including treatment words different from each other.

Figure 23:
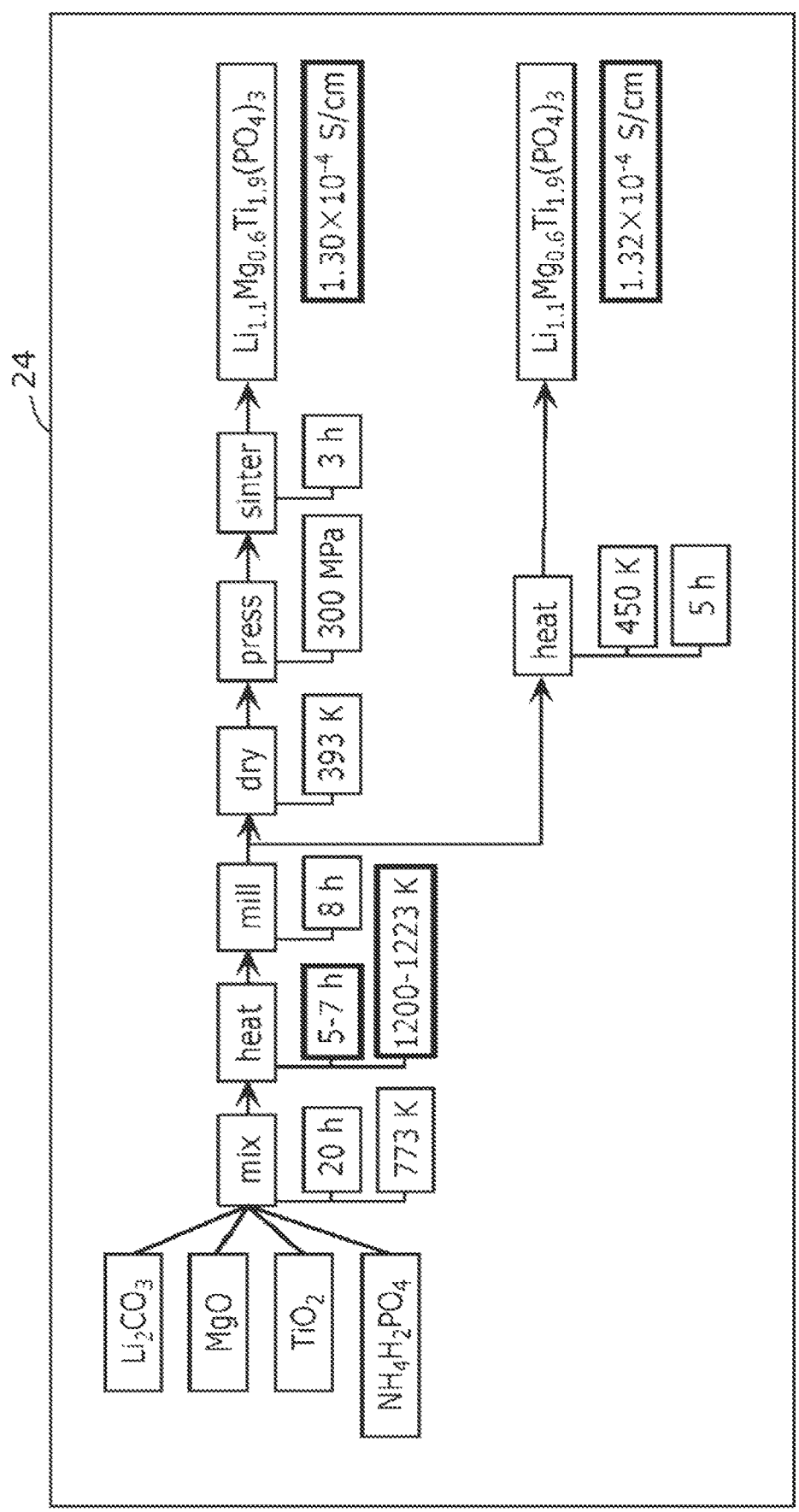
FIG. 23 is a diagram illustrating an example of a composite screen displayed on the display unit according to the third modification of the first embodiment.

FIG. 23 is a diagram illustrating an example of a composite screen displayed on the display unit 205 according to the present modification.

After generating the composite synthesis process in the above-described manner, the combining unit 204 causes the display unit 205 to display, for example, a composite screen 24 illustrated in FIG. 23. On the composite screen 24, the composite synthesis process generated by the combining unit 204 is displayed as a composite synthesis flow.

For example, in the composite synthesis flow illustrated in FIG. 23, the synthesis conditions "5 h" and "1223 K" included in the synthesis process of the paper ID "0001" have been replaced with the comprehensive synthesis conditions "5-7 h" and "1200-1223 K", respectively.

Furthermore, in the composite synthesis flow illustrated in FIG. 23, part of the synthesis process of the paper ID "0142" has been added to the synthesis process of the paper ID "0001". Specifically, the composite synthesis flow illustrated in FIG. 23 branches into two routes from the treatment word "mill" that is common to the above-described two synthesis processes. That is, a branch flow corresponding to part of the synthesis process of the paper ID "0142" is connected after the treatment word "mill". This branch flow is a flow in which the target material is generated through the treatment indicated by the treatment word "heat".

As described above, in the present modification, the combining unit 204 generates a composite synthesis process by comprehensively associating parts different from each other between the two synthesis processes with a part common to the two synthesis processes such that the flow of treatments branches from the common part to the different parts. That is, in the present modification, the treatment word extraction unit 104 extracts at least one treatment word i including the above-described treatment word i from the document i in (a-2), and the condition extraction unit 105 extracts at least one synthesis condition i including the above-described synthesis condition i from the document i in (a-3). The combining unit 204 generates composite process information by associating the above-described different parts with the above-described common part such that the flow of generating a material branches from the common part to the different parts.

Accordingly, in the present modification, for example, in a case where synthesis processes include a common treatment word and different treatment words, a composite synthesis process is generated such that the flow of generating a material branches from the treatment indicated by the common treatment word to the treatments indicated by the different treatment words. Accordingly, even if the synthesis processes include treatment words different from each other, a common treatment and different treatments can be displayed in an easy-to-understand manner. In addition, treatments different from each other can be displayed so as to be easily compared with each other.

In the example illustrated in FIG. 21A to FIG. 23, each of the pieces of synthesis process information used to generate the composite synthesis process information includes treatment words and synthesis conditions. Alternatively, each of the pieces of synthesis process information may include one treatment word and one synthesis condition. That is, each of the pieces of synthesis process information may be generated by extracting one treatment word and one synthesis condition from one document.

For example, as illustrated in FIG. 21A, starting material words, treatment words, synthesis conditions, a target material word, and a characteristic value are extracted from the document having the paper ID "0001", and synthesis process information is generated by using them. Alternatively, for example, one treatment word "dry" and one synthesis condition "393 K" for "dry" may be extracted instead of the treatment words and the synthesis conditions.

Similarly, as illustrated in FIG. 21B, starting material words, treatment words, synthesis conditions, a target material word, and a characteristic value are extracted from the document having the paper ID "0142", and synthesis process information is generated by using them. Alternatively, for example, one treatment word "heat" and one synthesis condition "450 K" for "heat" may be extracted instead of the treatment words and the synthesis conditions.

In such a case, the starting material words are common to the synthesis process information of the paper ID "0001" and the synthesis process information of the paper ID "0142". On the other hand, the treatment word "dry" and the synthesis condition "393 K" are different from the treatment word "heat" and the synthesis condition "450 K" between these pieces of synthesis process information. Thus, the composite process information generated from these pieces of synthesis process information has a flow branching from a common part (i.e., the starting material words) to the treatment word "dry" and the synthesis condition "393 K", and a flow branching from the common part to the treatment word "heat" and the synthesis condition "450 K". That is, even in a case where one treatment word and one synthesis condition are extracted from each of documents, composite process information can be generated by associating the above-described different parts with the common part so as to cause branching from the common part to the different parts.

Fourth Modification

In the first embodiment described above, a search for a synthesis process using the name of an organization or institution to which an author belongs is not performed. In the present modification, a search for a synthesis process using the name of an organization or institution is performed.

Figure 24:
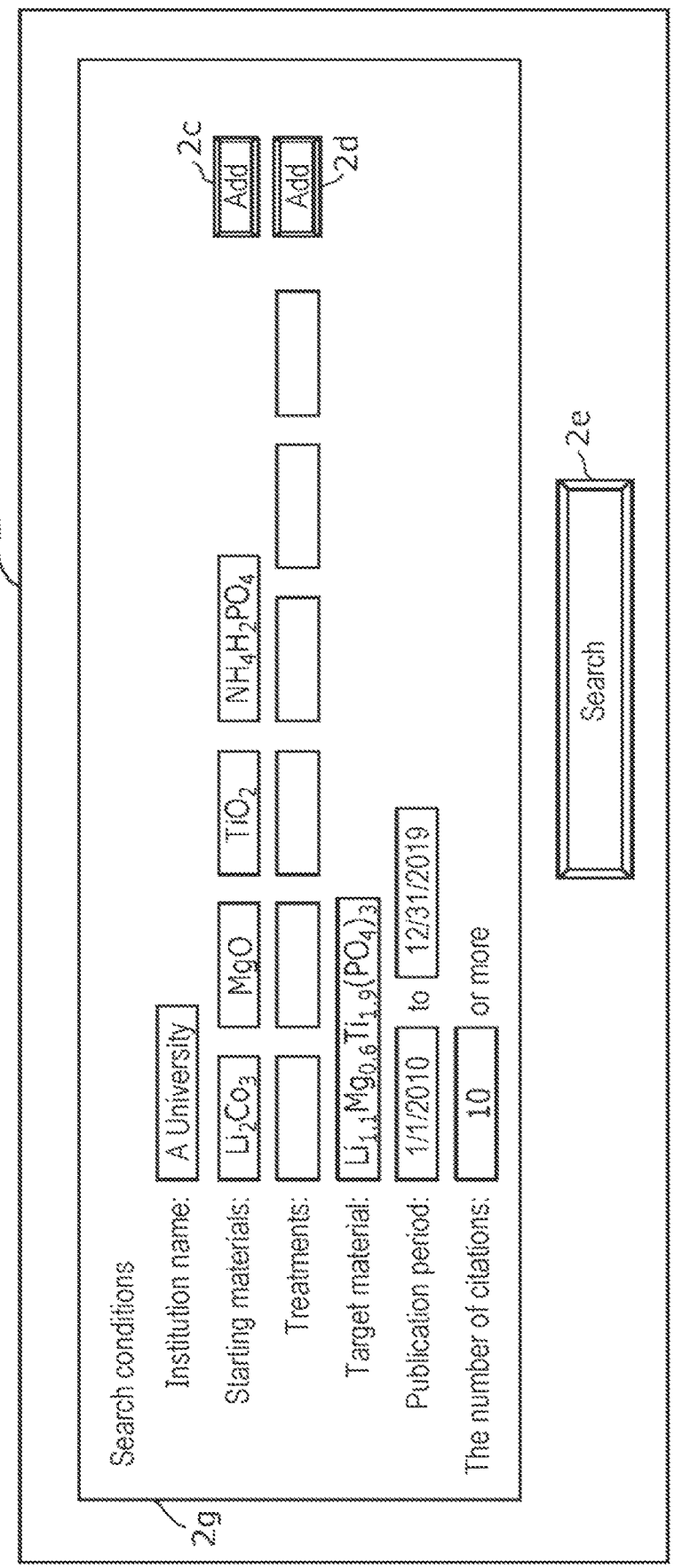
FIG. 24 is a diagram illustrating an example of a synthesis process search screen displayed on the display unit according to a fourth modification of the first embodiment.

FIG. 24 is a diagram illustrating an example of a synthesis process search screen displayed on the display unit 205 according to the present modification.

The search unit 203 according to the present modification causes the display unit 205 to display, for example, a synthesis process search screen 2f illustrated in FIG. 24 in response to a signal indicating a user operation result output from the operation device 340.

The synthesis process search screen 2f is different from the synthesis process search screen 2a according to the first embodiment in further including an institution name as a search condition. That is, the synthesis process search screen 2f includes a search condition window 2g, and the search condition window 2g includes an input field for inputting an institution name. The institution name is the name of an institution to which an author who has issued or published a document used to generate a synthesis process belongs (i.e., an organization name). In the present modification, the bibliographic information added to each of the synthesis processes accumulated in the synthesis process accumulation unit 201 includes an institution name.

When the synthesis process search screen 2f is displayed, the user fills in each input field by operating the operation device 340. For example, as illustrated in FIG. 24, the user inputs "A University" to the input field for an institution name. Furthermore, the user inputs material words "$Li_2CO_3$", "$MgO$", "$TiO_2$" and "$NH_4H_2PO_4$" to the four input fields for starting materials. Furthermore, the user inputs a material word "$Li_{1.1}Mg_{0.6}Ti_{1.9}(PO_4)_3$" to the input field for a target material, inputs "1/1/2010" to "12/31/2019"

to the input fields for a publication period, and inputs "10" or more to the input field for the number of citations.

Subsequently, the user selects the search start button 2e by operating the operation device 340. Accordingly, the search condition acceptance unit 202 accepts, as search conditions, the institution name, the names of the starting materials, the name of the target material, the publication period, and the number of citations input to the search condition window 2g. The search condition acceptance unit 202 outputs the search conditions to the search unit 203. Upon acquiring the search conditions from the search condition acceptance unit 202, the search unit 203 searches the synthesis processes accumulated in the synthesis process accumulation unit 201 for a synthesis process satisfying the search conditions.

When synthesis processes have been found through such a search, the combining unit 204 combines the synthesis processes in a manner similar to that in the first embodiment or the modification thereof, thereby generating a composite synthesis process. The composite synthesis process generated in this manner is a composite synthesis process for A University.

Here, for example, when "B Company" has been input instead of "A University" to the input field for an institution name on the synthesis process search screen 2f illustrated in FIG. 24, the combining unit 204 generates a composite synthesis process for B Company.

Figure 25A:
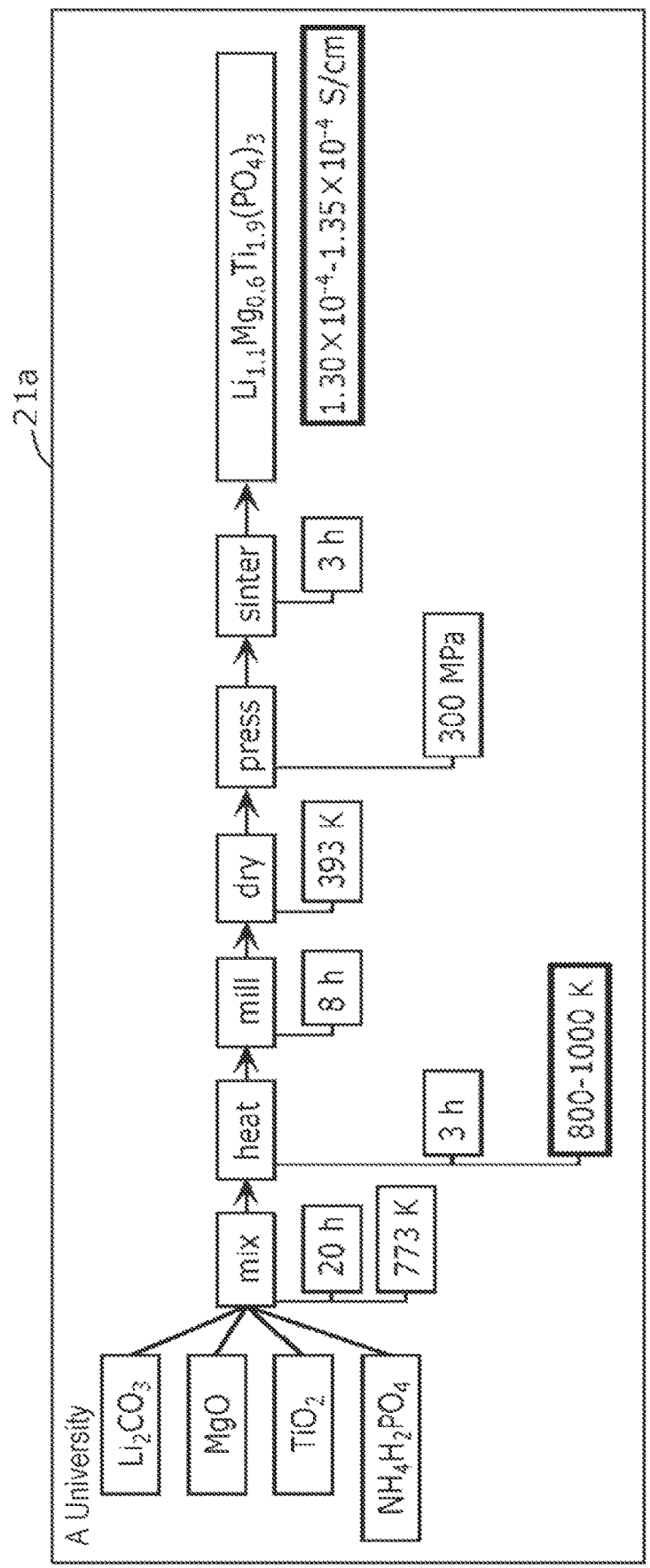
FIG. 25A is a diagram illustrating an example of a composite screen displayed on the display unit according to the fourth modification of the first embodiment.
Figure 25B:
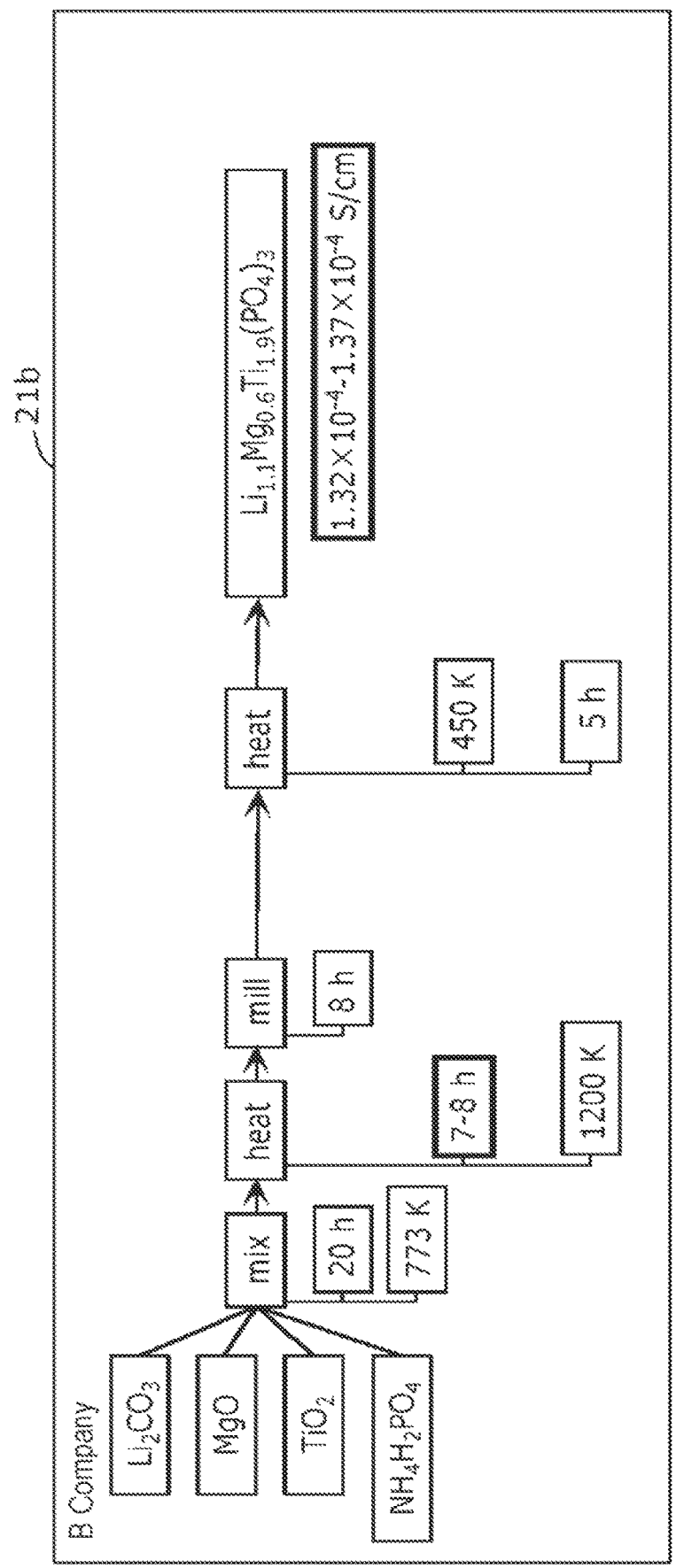
FIG. 25B is a diagram illustrating an example of a composite screen displayed on the display unit according to the fourth modification of the first embodiment.

FIG. 25A and FIG. 25B are each a diagram illustrating an example of a composite screen displayed on the display unit 205 according to the present modification.

When a composite synthesis process for A University has been generated, the combining unit 204 causes the display unit 205 to display, for example, a composite screen 21a for A University illustrated in FIG. 25A. On the composite screen 21a, the composite synthesis process for A University generated by the combining unit 204 is displayed as a composite synthesis flow. On the other hand, when a composite synthesis process for B Company has been generated, the combining unit 204 causes the display unit 205 to display, for example, a composite screen 21b for B Company illustrated in FIG. 25B. On the composite screen 21b, the composite synthesis process for B Company generated by the combining unit 204 is displayed as a composite synthesis flow.

A synthesis process for a target material varies according to an institution or organization that conducts experiments, such as a university or a company, and a tendency to conduct experiments may vary according to the facility or development strategy of the institution or organization. Thus, in the present modification, composite synthesis processes are displayed for individual institutions (for example, universities, companies, or the like) to which an author of a document such as a paper belongs, as illustrated in FIG. 25A and FIG. 25B. This enables the user to compare and grasp the composite synthesis processes of the individual institutions. In the example illustrated in FIG. 25A, the synthesis conditions associated with the treatment word "heat" in the composite synthesis process for A University are a short time and a low temperature. On the other hand, in the example illustrated in FIG. 25B, the synthesis conditions associated with the treatment word "heat" in the composite synthesis process for B Company are a long time and a high temperature. As a result, the characteristic value of the target material in the composite synthesis process for B Company tends to be greater than the characteristic value of the target material in the composite synthesis process for A University.

As described above, in the present modification, the composite synthesis processes of individual institutions can be compared with each other.

Also in the present modification, as in the above-described embodiment, synthesis processes are searched for by using a publication period as a search condition and are combined. Thus, composite synthesis processes can be classified by the years in which documents such as papers were published, and it is possible to, for example, determine how the synthesis conditions change in the individual years.

Fifth Modification

In the present modification, composite process information indicating a procedure of synthesizing an intermediate material from starting materials and further synthesizing a target material from the intermediate material is generated.

Figure 26:
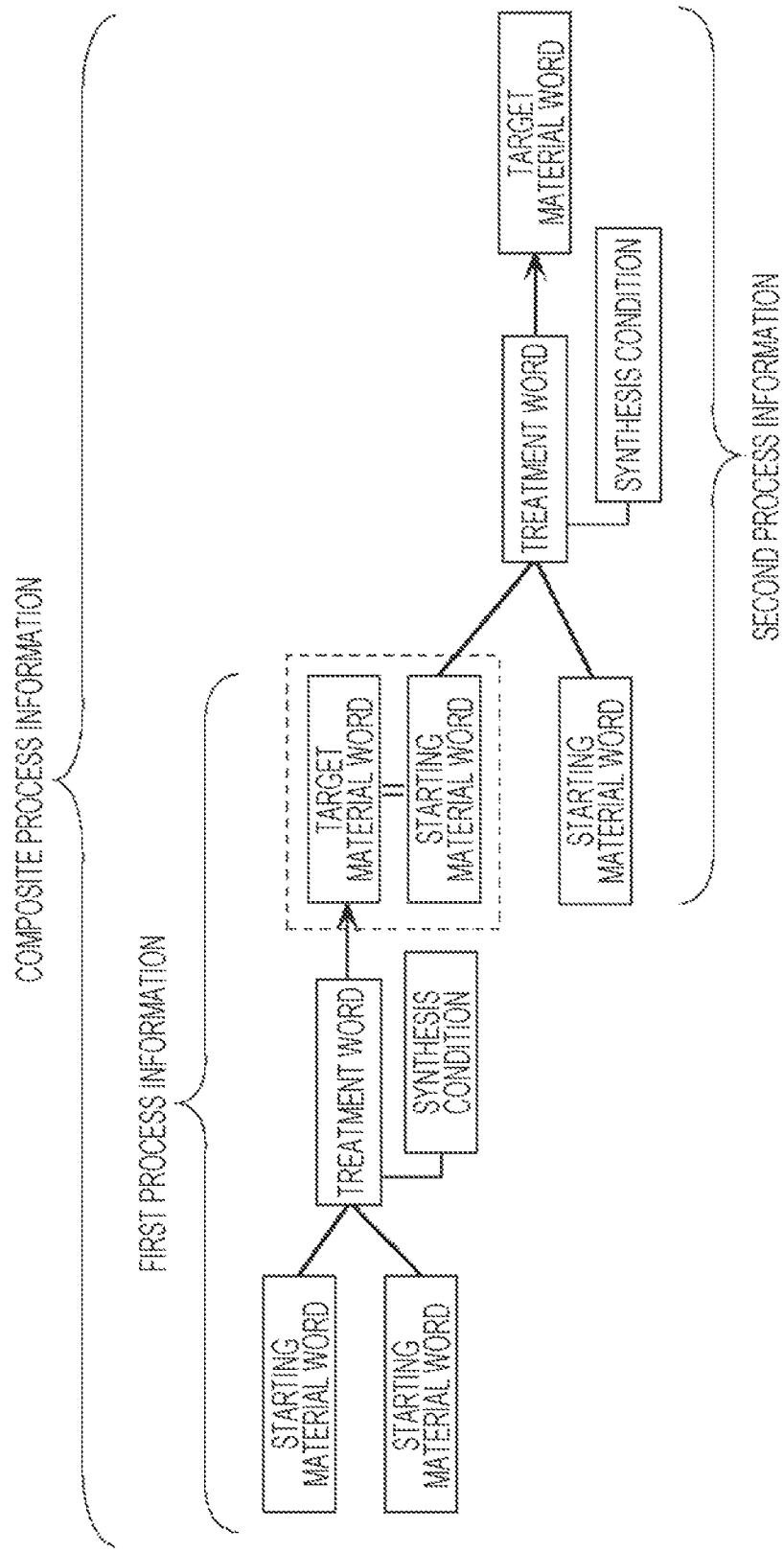
FIG. 26 is a diagram illustrating an example of composite process information including synthesis of an intermediate material.

FIG. 26 is a diagram illustrating an example of composite process information including synthesis of an intermediate material.

For example, the generation apparatus which is the synthesis process generation apparatus 100 generates first process information from a document and generates second process information from another document, as illustrated in FIG. 26. The first process information indicates starting material words, a treatment word, a synthesis condition, and a target material word in association with each other. Similarly to the first process information, the second process information indicates starting material words, a treatment word, a synthesis condition, and a target material word in association with each other. Here, the target material word of the first process information and one of the starting material words of the second process information may be identical words and common.

In such a case, the combining unit 204 according to the present modification may generate composite process information indicating a procedure of generating the target material indicated by the second process information from the starting materials indicated by the first process information. That is, the target material indicated by the first process information is handled as an intermediate material for generating the target material indicated by the second process information.

As described above, in the present modification, the target material word in the first process information and a starting material word in the second process information among the pieces of process information are identical material words and correspond to a part common to the pieces of process information. In such a case, the composite process information generated by the combining unit 204 indicates a procedure of synthesizing, from the starting materials indicated by the first process information, an intermediate material which is a material indicated by the identical material words corresponding to the common part, and generating the target material indicated by the second process information from the intermediate material.

Accordingly, composite process information indicating a procedure that is not described in any document can be generated. Thus, when such composite process information is displayed, a search for a new synthesis process can further be supported.

Second Embodiment

A synthesis process analysis apparatus in a second embodiment accepts a synthesis condition from a user, and estimates a characteristic value of a target material that is based on the accepted synthesis condition.

Figure 27:
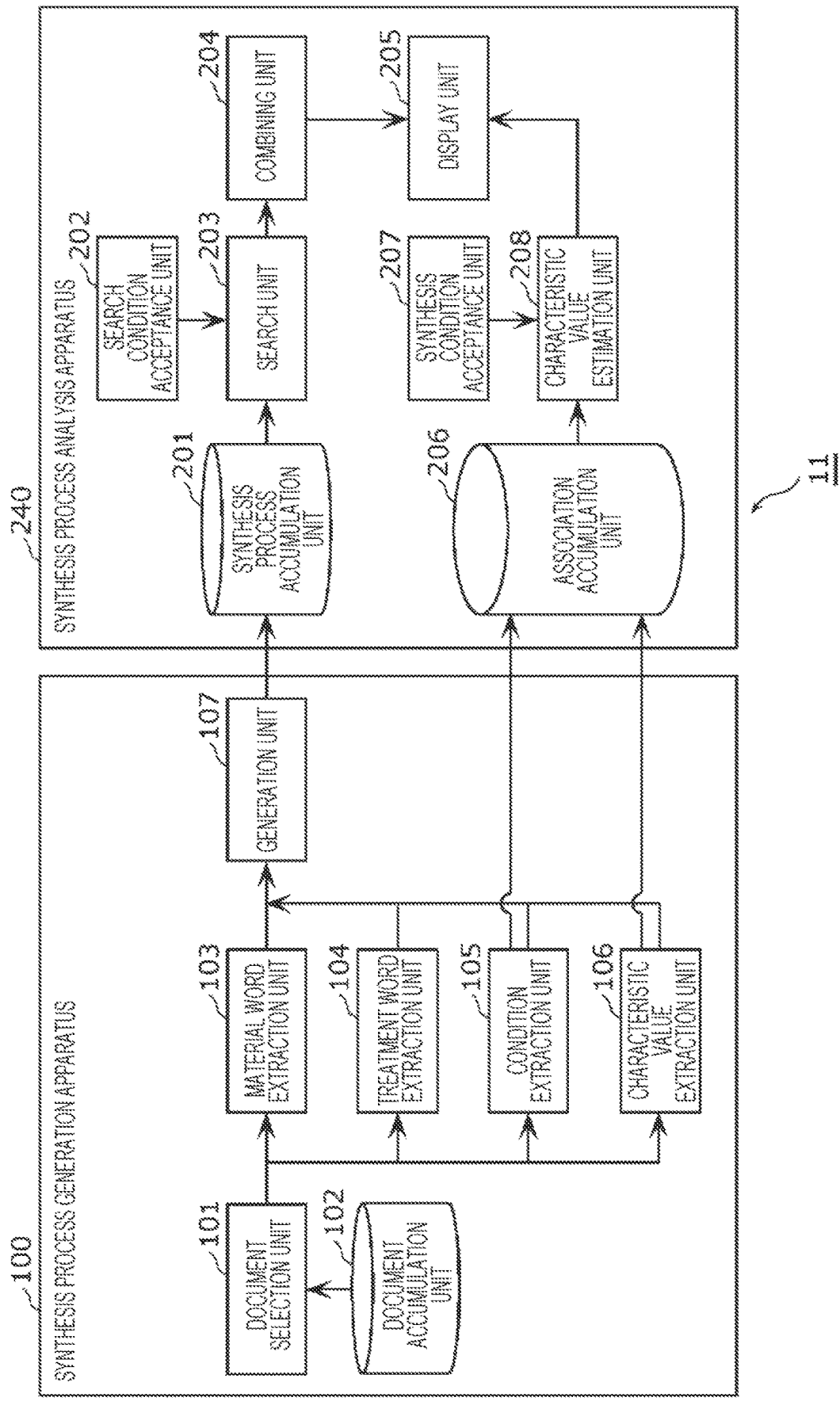
FIG. 27 is a block diagram illustrating an example of a functional configuration of a synthesis process search support system in a second embodiment.

FIG. 27 is a block diagram illustrating an example of a functional configuration of a synthesis process search support system in the present embodiment. Among the elements in the present embodiment, the same elements as those in the first embodiment are denoted by the same reference numerals as those in the first embodiment, and the detailed description thereof will be omitted.

A synthesis process search support system 11 in the present embodiment includes the synthesis process generation apparatus 100 and a synthesis process analysis apparatus 240.

The synthesis process generation apparatus 100 generates a synthesis process as in the first embodiment. The condition extraction unit 105 and the characteristic value extraction unit 106 of the synthesis process generation apparatus 100 in the present embodiment respectively output a synthesis condition and a characteristic value that have been extracted to the synthesis process analysis apparatus 240.

The synthesis process analysis apparatus 240 in the present embodiment includes the elements of the synthesis process analysis apparatus 200 in the first embodiment, and further includes an association accumulation unit 206, a synthesis condition acceptance unit 207, and a characteristic value estimation unit 208.

Association Accumulation Unit

The association accumulation unit 206 is a recording medium having a recording capacity for holding a synthesis condition extracted by the condition extraction unit 105 and a characteristic value extracted by the characteristic value extraction unit 106 in association with each other. In the association accumulation unit 206, at least one synthesis condition and a characteristic value are associated with each other for each of documents or each of synthesis processes generated from the documents. The association accumulation unit 206 may be, for example, a hard disk, a RAM, a ROM, a semiconductor memory, or the like. The association accumulation unit 206 may be volatile or nonvolatile.

Synthesis Condition Acceptance Unit

The synthesis condition acceptance unit 207 accepts, as an input synthesis condition, a synthesis condition corresponding to a signal indicating a user operation result output from the operation device 340. That is, the synthesis condition acceptance unit 207 accepts an input synthesis condition, which is a condition of a treatment.

Characteristic Value Estimation Unit

When a composite synthesis process has been generated and an input synthesis condition has been accepted by the synthesis condition acceptance unit 207, the characteristic value estimation unit 208 estimates a characteristic value of a target material in accordance with the input synthesis condition. The target material is a target material common to the synthesis processes used to generate the composite synthesis process. Thus, the characteristic value estimation unit 208 in the present embodiment estimates a characteristic value that is based on the input synthesis condition of the common target material. That is, the characteristic value estimation unit 208 estimates a characteristic value of the target material indicated by the common target material word, the characteristic value being based on the input synthesis condition.

Specifically, the characteristic value estimation unit 208 acquires, for each of the synthesis processes used to generate the composite synthesis process, a synthesis condition and a characteristic value included in the synthesis process from the association accumulation unit 206. The characteristic value estimation unit 208 then uses the acquired synthesis conditions and characteristic values to estimate the characteristic value of the target material that is based on the input synthesis condition accepted by the synthesis condition acceptance unit 207. Multiple regression analysis or the like may be used to estimate the characteristic value. For example, the characteristic value estimation unit 208 models a mathematical expression for outputting a characteristic value with respect to the input synthesis condition on the basis of the synthesis conditions and the characteristic values acquired from the association accumulation unit 206, by using multiple regression analysis. The characteristic value estimation unit 208 then substitutes the input synthesis condition accepted by the synthesis condition acceptance unit 207 into the modeled mathematical expression, thereby deriving a characteristic value. Accordingly, the characteristic value is estimated. Simultaneous equations may be used instead of multiple regression analysis, or the characteristic value may be estimated by interpolation processing. The interpolation may be interpolation or extrapolation.

As described above, the characteristic value estimation unit 208 in the present embodiment estimates a characteristic value that is based on an input synthesis condition, in accordance with a relationship between a synthesis condition included in each of synthesis processes and a characteristic value included in each of the synthesis processes. That is, the characteristic value estimation unit 208 in the present embodiment estimates a characteristic value that is based on an input synthesis condition, in accordance with a relationship between a synthesis condition i included in each of pieces of process information and a characteristic value i included in each of the pieces of process information.

Figure 28:
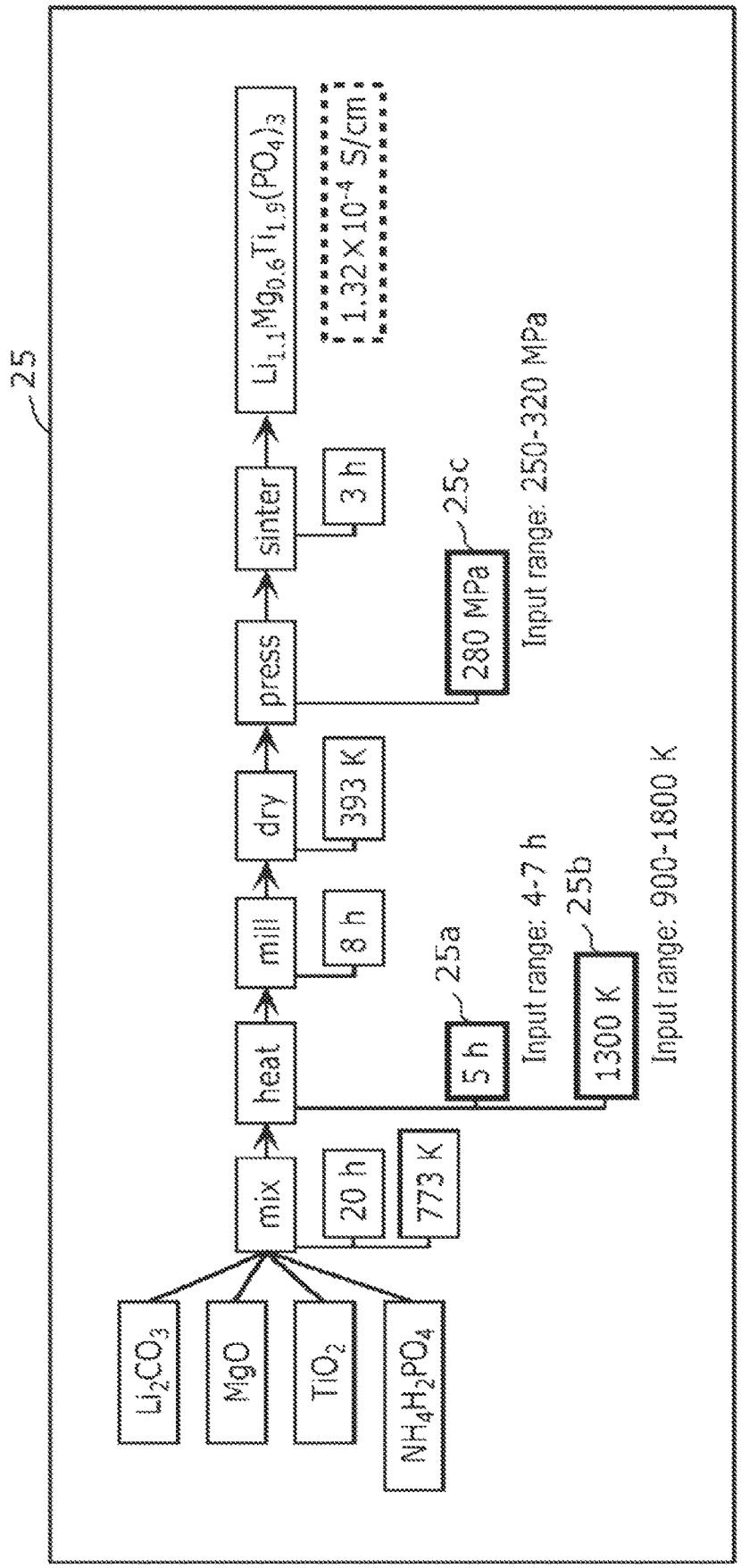
FIG. 28 is a diagram illustrating an example of a composite screen displayed on the display unit in the second embodiment.

FIG. 28 is a diagram illustrating an example of a composite screen displayed on the display unit 205 in the present embodiment.

Similarly to the first embodiment, the combining unit 204 in the present embodiment causes display unit 205 to display, for example, a composite screen 25 illustrated in FIG. 28 after generating a composite synthesis process from the four synthesis processes illustrated in FIG. 14A to FIG. 14D. On the composite screen 25, the composite synthesis process generated by the combining unit 204 is displayed as a composite synthesis flow.

In the composite synthesis flow in the present embodiment, a comprehensive synthesis condition is indicated as an input range. A comprehensive characteristic value is not indicated. For example, a comprehensive synthesis condition "4-7 h" is indicated as the input range of the synthesis condition of time in the treatment indicated by the treatment word "heat", and a comprehensive synthesis condition "900-1800 K" is indicated as the input range of the synthesis condition of temperature in the treatment. Similarly, a comprehensive synthesis condition "250-320 MPa" is indicated as the input range of the synthesis condition of pressure in the treatment indicated by the treatment word "press".

Here, the composite screen 25 is provided with, for individual input ranges, input fields 25a to 25c (thick-solid-line frames in FIG. 28) for inputting synthesis conditions in the input ranges. The user inputs synthesis conditions to the input fields 25a to 25c by operating the operation device 340. The synthesis conditions input in this manner are accepted as input synthesis conditions by the synthesis condition acceptance unit 207. After the input of the synthesis conditions to all the input fields 25a to 25c has been completed, the characteristic value estimation unit 208 estimates a characteristic value of the target material in accordance with the synthesis conditions input to the input fields 25a to 25c. The characteristic value estimation unit 208 then displays the estimated characteristic value on the composite screen 25 of the display unit 205. The characteristic value estimated in this manner is arranged near the material word "$Li_{1.1}Mg_{0.6}Ti_{1.9}(PO_4)_3$" of the target material on the composite screen 25. In the example in FIG. 28, the estimated characteristic value is arranged in a thick-broken-line frame. In this way, the display unit 205 displays the characteristic value estimated by the characteristic value estimation unit 208. The display unit 205, which is an example of an outputter in the present embodiment, displays the characteristic value in the above-described manner. Alternatively, the outputter may output the characteristic value estimated by the characteristic value estimation unit 208.

For example, a synthesis condition of time "5 h" and a synthesis condition of temperature "1300 K" for the treatment indicated by the treatment word "heat", and a synthesis condition of pressure "280 MPa" for the treatment indicated by the treatment word "press" are accepted as input synthesis conditions by the synthesis condition acceptance unit 207. In this case, the characteristic value estimation unit 208 estimates the characteristic value "$1.32 \times 10^{-4}$ S/cm" of the target material and displays it on the display unit 205.

Figure 29:
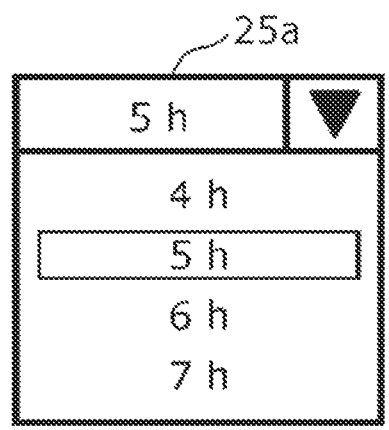
FIG. 29 is a diagram for describing an input method for an input field on a composite screen in the second embodiment.

FIG. 29 is a diagram for describing an input method for an input field on the composite screen 25.

For example, when inputting a synthesis condition of time to the input field 25a, the user may input any synthesis condition by operating the operation device 340, or may select any candidate as a synthesis condition from among candidates.

Specifically, after generating a comprehensive synthesis condition, the combining unit 204 provides the composite screen 25 with the input field 25a in which at least one numerical value within the range indicated by the comprehensive synthesis condition can be selected as a candidate for a synthesis condition. For example, the input field 25a is constituted by a pull-down menu. When the comprehensive synthesis condition of time is "4-7 h", the input range is "4-7 h". Thus, upon the input field 25a being selected by the user, 4 h, 5 h, 6 h, and 7 h are displayed as candidates for the synthesis condition of time. The user selects one of the candidates by operating the operation device 340. Accordingly, the selected candidate is input as a synthesis condition to the input field 25a. The synthesis condition input in this manner is accepted as an input synthesis condition by the synthesis condition acceptance unit 207.

As described above, in the present embodiment, a characteristic value of a target material is estimated and displayed in response to a user's setting of an input synthesis condition. Thus, for example, a synthesis process for a material having a new characteristic value can be easily searched for. Thus, the user is able to grasp the characteristic value of the target material with respect to a certain synthesis condition without conducting an experiment.

Third Embodiment

A synthesis process analysis apparatus in a third embodiment presents information about a facility capable of satisfying a comprehensive synthesis condition.

Figure 30:
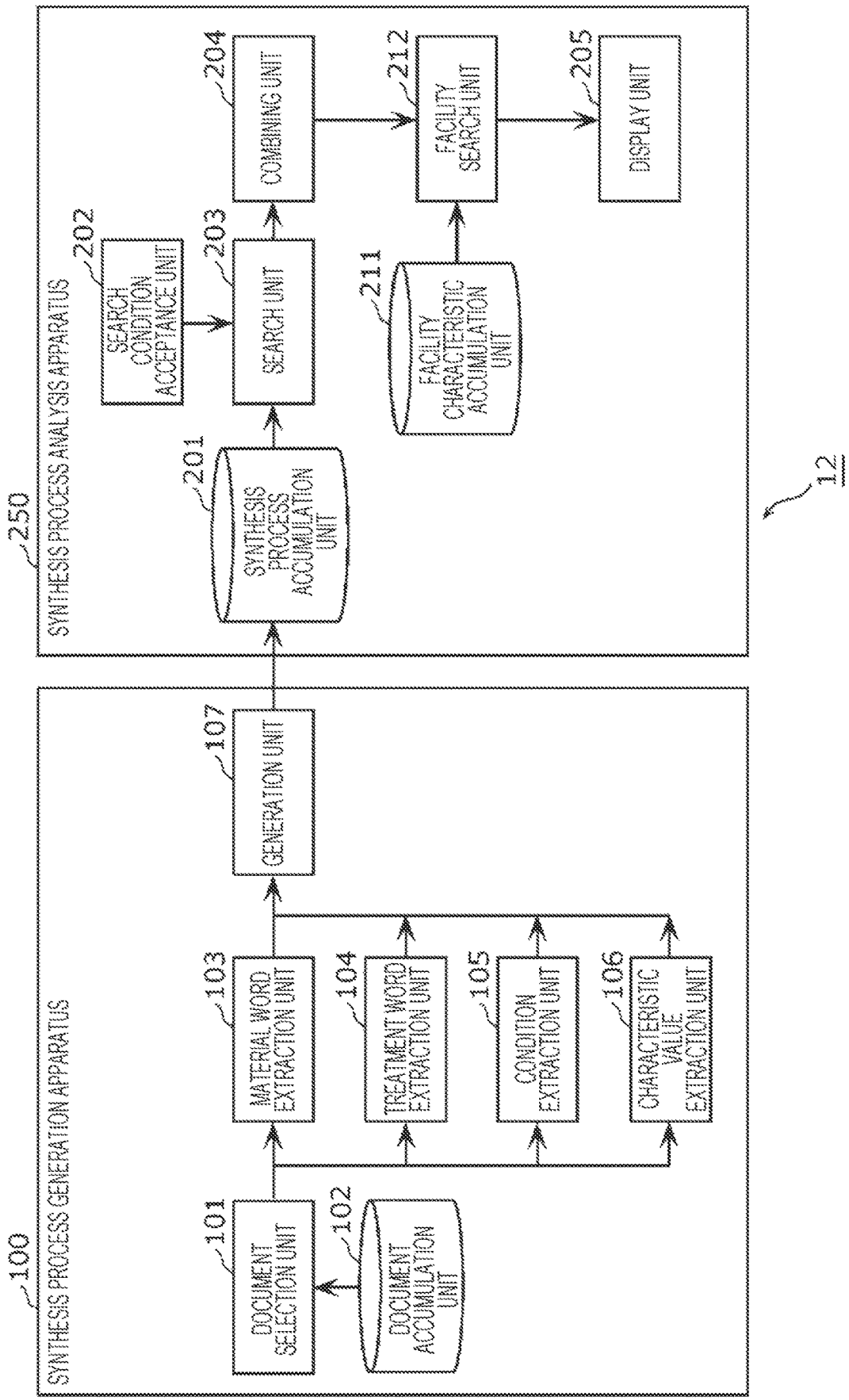
FIG. 30 is a block diagram illustrating an example of a functional configuration of a synthesis process search support system in a third embodiment.

FIG. 30 is a block diagram illustrating an example of a functional configuration of a synthesis process search support system in the present embodiment. Among the elements in the present embodiment, the same elements as those in the first embodiment are denoted by the same reference numerals as those in the first embodiment, and the detailed description thereof will be omitted.

A synthesis process search support system 12 in the present embodiment includes the synthesis process generation apparatus 100 and a synthesis process analysis apparatus 250.

The synthesis process analysis apparatus 250 in the present embodiment includes the elements of the synthesis process analysis apparatus 200 in the first embodiment, and further includes a facility characteristic accumulation unit 211 and a facility search unit 212.

Facility Characteristic Accumulation Unit

The facility characteristic accumulation unit 211 is a recording medium that holds facility information. The facility information indicates, for each of facilities, a list of treatment conditions that can be satisfied by the facility. The facility characteristic accumulation unit 211 may be, for example, a hard disk, a RAM, a ROM, a semiconductor memory, or the like. The facility characteristic accumulation unit 211 may be volatile or nonvolatile.

Facility Search Unit

The facility search unit 212 searches for a facility capable of performing a treatment under a comprehensive synthesis condition generated by the combining unit 204, by referring to the facility information described above.

The display unit 205 in the present embodiment displays information about the facility found through the search performed by the facility search unit 212. The display unit 205, which is an example of an outputter in the present embodiment, displays information about a facility as described above. The outputter may output information about a facility found through the search performed by the facility search unit 212.

FIG. 31 is a diagram illustrating an example of facility information in the present embodiment.

The facility information indicates, for each of facilities, a performance value and a price of the facility, as illustrated in FIG. 31, for example. Each facility is identified by a manufacturer name and a model number. The performance value is a treatment condition that can be satisfied. For example, the facility information indicates that a facility having a manufacturer name "A Company" and a model number "AS-0122" has a performance value "260-300 MPa" as a satisfiable condition of a pressurization treatment, and that the price of the facility is "500,000 yen".

Figure 32:
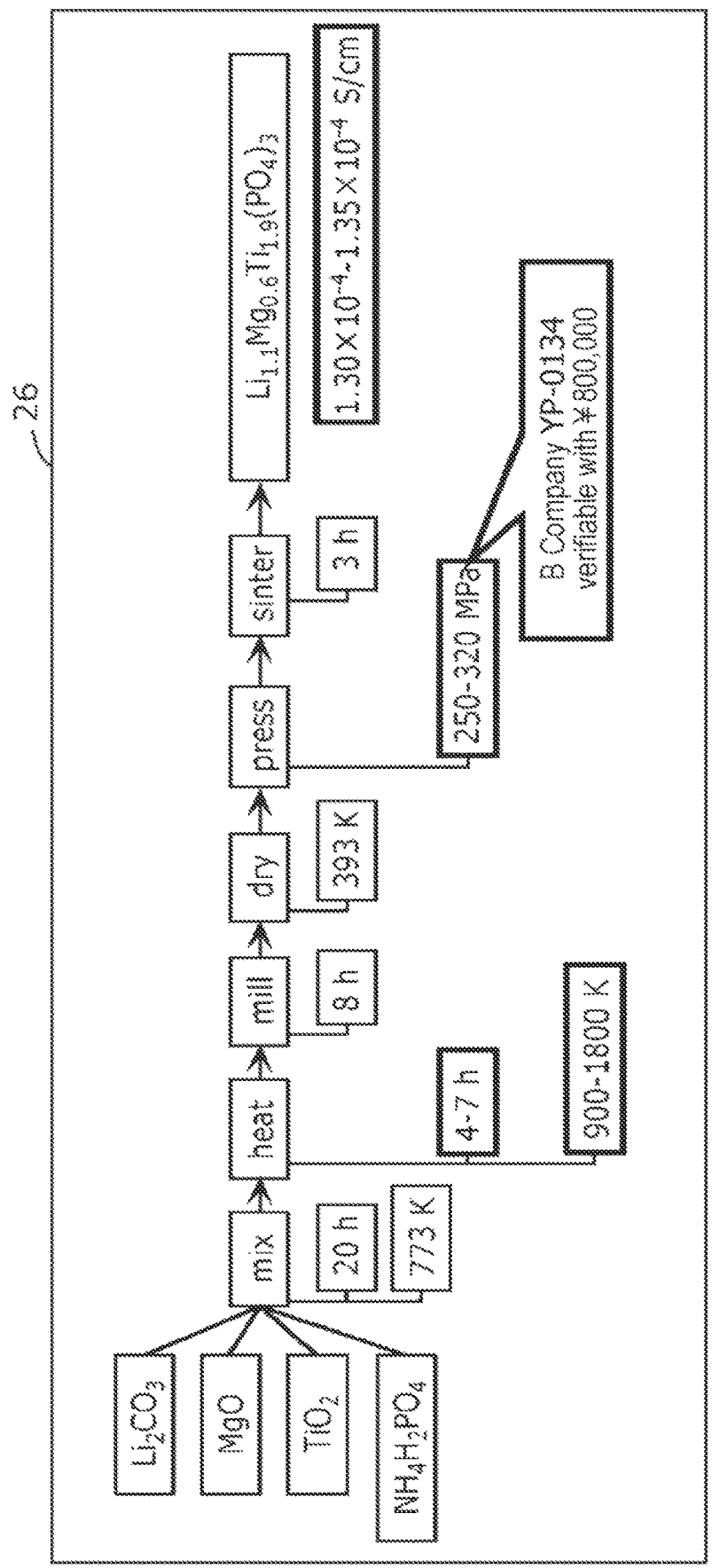
FIG. 32 is a diagram illustrating an example of a composite screen displayed on the display unit in the third embodiment.

FIG. 32 is a diagram illustrating an example of a composite screen displayed on the display unit 205 in the present embodiment.

As in the first embodiment, the combining unit 204 in the present embodiment causes display unit 205 to display, for example, a composite screen 26 illustrated in FIG. 32 after generating a composite synthesis process from the four synthesis processes illustrated in FIG. 14A to FIG. 14D. On the composite screen 26, the composite synthesis process generated by the combining unit 204 is displayed as a composite synthesis flow.

Furthermore, in the present embodiment, the facility search unit 212 displays information about a facility found through a search on the composite screen 26. For example, a comprehensive synthesis condition of pressure "250-320 MPa" is generated by the combining unit 204. At this time, the facility search unit 212 searches for a facility capable of performing a pressurization treatment under the comprehensive synthesis condition of pressure "250-320 MPa" by referring to, for example, the facility information illustrated in FIG. 31. As a result, the facility search unit 212 finds a facility having a manufacturer name "B Company" and a model number "YP-0134". The facility search unit 212 then causes the display unit 205 to display the manufacturer name "B Company", the model number "YP-0134", and, for example, a price "800,000 yen" associated with the facility in the facility information, in association with the comprehensive synthesis condition "250-320 MPa". The price need not necessarily be displayed.

Accordingly, in the present embodiment, it is possible to display a composite synthesis flow and to easily inform the user of a facility capable of performing a treatment under a comprehensive synthesis condition included in the composite synthesis flow. As a result, a facility required for synthesizing a material can be easily arranged.

That is, in the present embodiment, when a comprehensive synthesis condition and a comprehensive characteristic value of a target material included in a composite synthesis flow are displayed, it is possible to determine which facility can be used to verify the composite synthesis flow.

In the present embodiment, information about a facility and a composite synthesis flow are simultaneously displayed, but need not necessarily be simultaneously displayed. For example, when a displayed comprehensive synthesis condition has been selected by the user, information about a facility satisfying the comprehensive synthesis condition may be displayed. That is, in response to receipt from the operation device 340 of a signal indicating that a comprehensive synthesis condition included in a composite synthesis flow has been selected, the facility search unit 212 searches for a facility capable of performing a treatment under the comprehensive synthesis condition by referring to the facility information. The facility search unit 212 then causes the display unit 205 to display information about the facility in association with the comprehensive synthesis condition.

Fourth Embodiment

A support apparatus in the present embodiment is a system that extracts information from a document such as a paper and analyzes the information to enhance the efficiency of business activities of vendors that sell materials or apparatuses.

In the business activities of vendors, it is important to collect information about customers in advance and find a customer that is likely to purchase a material or apparatus, in order to increase a contract conclusion rate.

However, organizations such as universities or companies, which are major customers of the vendors, rarely disclose information about materials or apparatuses used in experiments. Thus, it is difficult for the vendors to collect information about their customers.

In addition, it is necessary to continuously update information about customers to efficiently conduct business activities. However, updating of the information about customers is costly because vendors conduct business activities mainly by manpower.

The support apparatus in the present embodiment analyzes information extracted from paper data published by researchers belonging to an organization, thereby being capable of improving the efficiency of business activities of vendors.

Schematic Configuration of System

Figure 33:
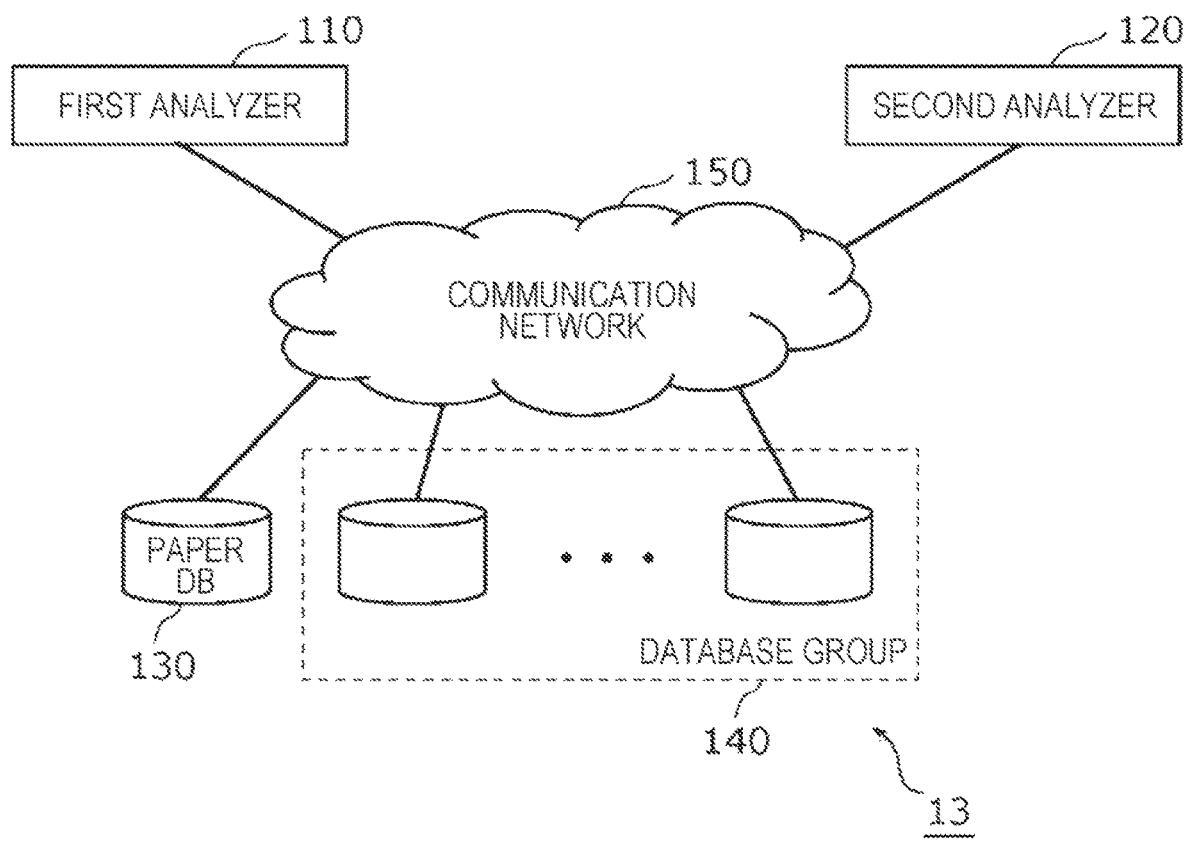
FIG. 33 is a diagram illustrating an example of a schematic configuration of a support apparatus in a fourth embodiment.

FIG. 33 is a diagram illustrating an example of a schematic configuration of the support apparatus.

A support apparatus 13 includes a first analyzer 110, a second analyzer 120, a paper database 130, and a database group 140, which are connected to each other via a communication network 150.

The paper database 130 is also called a paper DB, and is a recording medium that holds pieces of paper data, each of which is a document. The paper database 130 corresponds to the document accumulation unit 102 in the first to third embodiments.

The database group 140 includes databases each of which is a recording medium used by at least one of the first analyzer 110 or the second analyzer 120. Each of the databases is configured as a recording medium similarly to the paper database 130. These recording media are, for example, hard disks. The recording media may be recording media other than hard disks, such as RAMs, ROMs, or semiconductor memories. These recording media may be volatile or nonvolatile.

The first analyzer 110 reads out pieces of paper data from the paper database 130 via the communication network 150. The first analyzer 110 then extracts, for each of the pieces of paper data, pieces of information as customer information from the piece of paper data, thereby generating a data set corresponding to the piece of paper data. The first analyzer 110 stores the generated data sets in the database group 140 via the communication network 150. In the present embodiment, an organization to which the author of a paper belongs is, for example, a university, a laboratory, or a company, and is a customer of a vendor that sells products such as apparatuses or materials.

The second analyzer 120 reads out the data sets from the database group 140 via the communication network 150 and estimates, on the basis of the data sets, various types of information related to the purchase of the products by customers. In the present embodiment, the second analyzer 120 is used by, for example, the above-described vendor or a person belonging to the vendor.

The first analyzer 110, the second analyzer 120, the paper database 130, and the database group 140 may be installed in the same facility or may be separately arranged in facilities apart from each other. The first analyzer 110 and the second analyzer 120 may be used by different users or may be used by the same user.

Paper Data

FIG. 34 is a diagram illustrating an example of contents of a paper bib.

In the present embodiment, paper data is made up of a combination of two files. One of the two files is a paper PDF, and the other is a paper bib. The paper PDF is constituted by a PDF file, and is a file in which the contents of a paper are described in, for example, a natural language. Note that the paper PDF may include text data. The paper bib is a file having "bib" added thereto as an extension, and is also called a BIB file.

The paper bib is metadata of a paper, for example, as illustrated in FIG. 34. The paper bib describes the title of the paper, the name of the author of the paper, the name of the organization to which the author belongs (affiliation), the issue date or publication date of the paper, and so forth. Hereinafter, the name of the author is also called an author name, and the name of the organization is also called an organization name, a research organization name, or a belonging organization name. The paper bib is structured data.

Thus, the first analyzer 110 in the present embodiment is capable of easily extracting the above-described author name, organization name, publication date, and so forth from the paper bib through processing by a computer program.

FIG. 35 is a diagram illustrating an example of contents of the paper PDF.

As illustrated in part (a) of FIG. 35, the paper PDF describes, for example, information about an apparatus used in an experiment or the like in the paper and information about an apparatus providing organization as a vendor or manufacturer of the apparatus. The information about the apparatus is also called apparatus information and is, for example, a name, another name, a model, or a model number of the apparatus. The information about the apparatus providing organization is, for example, the name of the apparatus providing organization. The apparatus providing organization is specifically a vendor or manufacturer of the apparatus, and is a seller of the apparatus.

In the example illustrated in part (a) of FIG. 35, the paper PDF describes "TN-200", which is the model number of an apparatus, and "Korea Chem Inc.", which is the name of the seller of the apparatus. Furthermore, the paper PDF describes "XRD, Gaku Mini II", which is the model number of an apparatus, and "Japan Chem Inc.", which is the name of the seller of the apparatus.

In addition, as illustrated in part (b) of FIG. 35, the paper PDF describes, for example, information about a material used in an experiment in the paper and information about a material providing organization that sold or manufactured the material. The information about the material is also called material information and is, for example, a name or another name of the material. The information about the material providing organization is, for example, the name of the material providing organization. The material providing organization is specifically a vendor or manufacturer of the material, and is a seller of the material.

In the example illustrated in part (b) of FIG. 35, the paper PDF describes "China Industry", which is the name of the seller of the material named "Octylamine". Furthermore, the paper PDF describes "Sako Pure Chemicals Co., Ltd", which is the name of the seller of the material named "Acetone and methanol".

FIG. 36 is a diagram illustrating an example of other contents of the paper PDF.

As illustrated in FIG. 36, the paper PDF further describes, for example, information about a project that supports an experiment in the paper. The information about the project is also called project information and is, for example, the name or identification number of the project.

In the example illustrated in FIG. 36, the paper PDF describes "the National Material Science Fundation of Japan", which is the name of a project, and "No. 11112222 and 33334444", which is the identification number of the project. Furthermore, the paper PDF describes "the Specialized Research Fund for the Doctoral Program of Higher Education of Japan", which is the name of a project, and "No. ABC111", which is the identification number of the project.

Detailed Configuration of System

Figure 37:
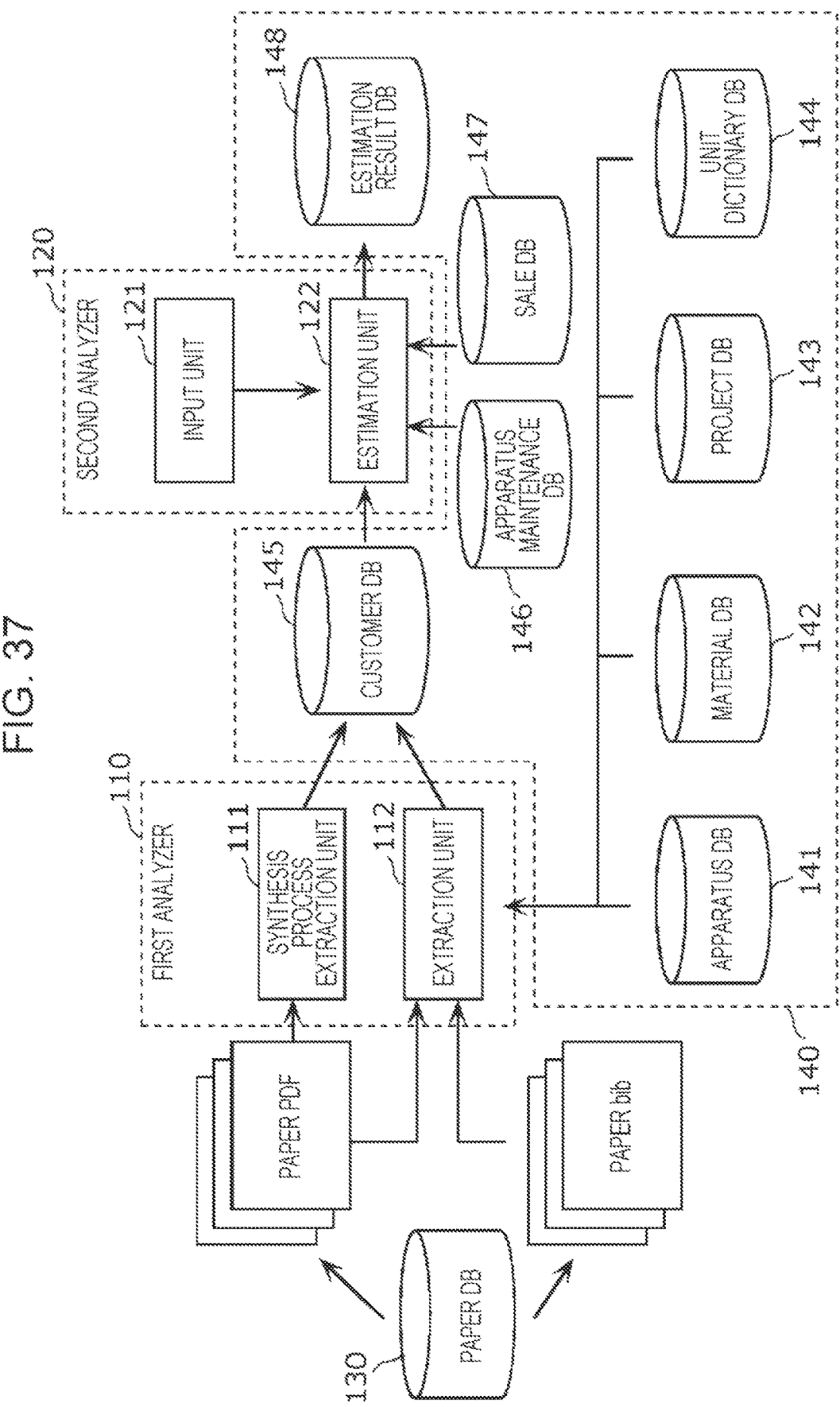
FIG. 37 is a diagram illustrating an example of a detailed configuration of the support apparatus in the fourth embodiment.

FIG. 37 is a diagram illustrating an example of a detailed configuration of the support apparatus 13.

The first analyzer 110 includes a synthesis process extraction unit 111 and an extraction unit 112.

The synthesis process extraction unit 111 generates a synthesis process from paper PDFs, each of which is an example of a document, similarly to the synthesis process generation apparatus 100 in the first to third embodiments described above. That is, the synthesis process extraction unit 111 extracts a synthesis process from a paper PDF. The synthesis process extraction unit 111 stores the extracted synthesis process in a customer database 145 included in the database group 140.

The synthesis process extraction unit 111 may be constituted by the elements other than the document accumulation unit 102 included in the synthesis process generation apparatus 100 in the first to third embodiments.

The extraction unit 112 downloads pieces of paper data from the paper database 130. Accordingly, a paper PDF and a paper bib included in the paper data are simultaneously downloaded. The extraction unit 112 then extracts, for each of the pieces of downloaded paper data, individual pieces of information as customer information from the paper PDF and the paper bib included in the piece of paper data. The extraction unit 112 then stores a data set including the pieces of customer information extracted from the paper data in the customer database 145.

When extracting the customer information from the paper data, the extraction unit 112 uses an apparatus database 141, a material database 142, a project database 143, and a unit dictionary database 144 included in the database group 140.

The second analyzer 120 includes an input unit 121 and an estimation unit 122.

The input unit 121 accepts individual pieces of information in accordance with an input operation performed by a user of the second analyzer 120. The input unit 121 may be configured as, for example, a keyboard, a touch sensor, a touch pad, a mouse, or the like.

The estimation unit 122 estimates various types of information about the purchase of products by customers by using the customer database 145, and an apparatus maintenance database 146 and a sale database 147 described below.

The database group 140 includes the apparatus database 141, the material database 142, the project database 143, the unit dictionary database 144, the customer database 145, the apparatus maintenance database 146, the sale database 147, and an estimation result database 148.

The apparatus database 141 is also called an apparatus DB and holds, for each of apparatuses, pieces of information about the apparatus. The pieces of information about the apparatus include, for example, the name, price, specifications, and so forth of the apparatus.

The material database 142 is also called a material DB and holds, for each of materials, pieces of information about the material. The pieces of information about the material include, for example, the name, price, and so forth of the material.

The project database 143 is also called a project DB and holds, for each of projects, pieces of information about the project. The pieces of information about the project include, for example, the name, budget amount, and so forth of the project.

The unit dictionary database 144 is also called a unit dictionary DB and holds information about units of weight.

The customer database 145 is also called a customer DB. As described above, the customer database 145 stores synthesis processes extracted by the synthesis process extraction unit 111, and data sets each including pieces of customer information extracted by the extraction unit 112.

The apparatus maintenance database 146 is also called an apparatus maintenance DB and holds information about a failure of an apparatus sold by a vendor. The information about a failure of an apparatus is, for example, a failure rate curve of the apparatus. The failure rate curve indicates an initial failure period, an accidental failure period, and a wear-out failure period, and also indicates a temporal change in the failure rate in each of the periods. The initial failure period is a period during which defects in the design or manufacture of the apparatus are likely to cause a failure. The accidental failure period is a period during which the cause of a failure is not related to the elapse of time. The wear-out failure period is a period during which wear or tear over time is likely to cause a failure. The estimation unit 122 estimates a chronological change in the failure rate of the apparatus by using such a failure rate curve. The above-described failure rate curve held in the apparatus maintenance database 146 is automatically or manually generated or updated, and is constantly maintained in the latest state, for example.

The sale database 147 is also called a sale DB and holds sale conditions. A sale condition is a condition related to a discount of a material or an apparatus and is, for example, a condition that the price of material A is discounted when X g or more of material A is collectively purchased. The estimation unit 122 may estimate various types of information about the purchase of products by customers by referring to such sale conditions. The sale conditions held in the sale database 147 are automatically or manually generated or updated, and are constantly maintained in the latest state, for example.

The estimation result database 148 is also called an estimation result DB. The estimation result database 148 stores information estimated by the estimation unit 122, for example, material estimation information and apparatus estimation information described below.

Databases and Processing by Extraction Unit 112

FIG. 38 is a diagram illustrating an example of a data table held in the apparatus database 141.

The apparatus database 141 holds, for example, a data table 141*a* illustrated in FIG. 38. The data table 141*a* shows, for each of apparatuses, pieces of information about the apparatus. For example, the date table 141*a* shows, for each of apparatuses, an apparatus ID, an apparatus name, an apparatus another name, an apparatus model number, a vendor name, a related apparatus ID, a price, a usage starting month, and specifications of the apparatus in association with each other. The apparatus ID is identification information for identifying the apparatus, the apparatus name is the name of the apparatus, and the apparatus another name is another name or abbreviation different from the name of the apparatus. The apparatus model number is a model number or a model of the apparatus defined by the vendor of the apparatus. The vendor name is the name of the vendor of the apparatus. The related apparatus ID is identification information of an apparatus related to the apparatus having an apparatus ID associated with the related apparatus ID, and is, for example, identification information of an apparatus having applications and functions similar to those of the apparatus having the apparatus ID. The price is a price of the apparatus defined by the vendor of the apparatus having the apparatus ID, and the usage starting month is a month in which the usage of the apparatus is started. The usage starting month may be a sale starting month of the apparatus. The specifications are specifications related to the applications of the apparatus. For example, the specifications of an apparatus for ball milling include a ball diameter, a material of the apparatus, a disk rotation speed, or the like. On the other hand, the specifications of an apparatus for annealing include an annealing method (for example, far-infrared irradiation or hot air irradiation), a maximum firing temperature, an atmospheric condition (nitrogen, argon, oxygen, etc.), or the like.

Specifically, the data table 141*a* shows, for the apparatus having an apparatus ID "1", the apparatus ID "1", an apparatus name "Ball Milling Machine" of the apparatus, an apparatus another name "BM" of the apparatus, an apparatus model number "BZ204B" of the apparatus, a vendor name "Osaka Industries." of the apparatus, a related apparatus ID "[3, 4]" of the apparatus, a price "80,000 yen" of the apparatus, a usage starting month "July 2011" of the apparatus, and specifications of the apparatus. The related apparatus ID "[3, 4]" indicates that the apparatuses having the apparatus IDs "3" and "4" are related to the apparatus having the apparatus ID "1" as related apparatuses.

When apparatuses having the same apparatus name and the same apparatus model number are sold by different vendors, the prices of the apparatuses may be different from each other. Thus, in the data table 141*a*, apparatuses that have the same apparatus name and the same apparatus model number and that are sold by different vendors are associated with apparatus IDs different from each other.

The data table 141*a* in the apparatus database 141 is a data table that can be created on the basis of catalogs published by individual apparatus vendors on web pages of the vendors. The data table 141*a* may be created automatically or manually. The lineups of apparatuses sold by apparatus vendors are continuously updated. Thus, the data table 141*a* held in the apparatus database 141 may be constantly updated to the latest state.

The extraction unit 112 in the present embodiment extracts apparatus information from paper data, for example, the paper PDF illustrated in part (a) of FIG. 35, by using Bidirectional Encoder Representations from Transformers (BERT). BERT is a model based on deep learning for which high performance has been reported in named entity extraction.

The extraction unit 112 searches the data table 141*a* for an apparatus name that matches the extracted apparatus information. If the apparatus name is not found, the extraction unit 112 searches the data table 141*a* for an apparatus another name that matches the extracted apparatus information. If the apparatus another name is not found, the extraction unit 112 searches the data table 141*a* for an apparatus model number that matches the extracted apparatus information. If the apparatus name or the like is found through the search, the extraction unit 112 specifies the apparatus ID, the vendor name, the related apparatus ID, the price, and so forth associated with the apparatus name or the like in the data table 141*a* as customer information related to the apparatus. Accordingly, customer information about the apparatus is extracted from the paper data. The extraction unit 112 then associates the paper ID of the paper data with the extracted customer information about the apparatus. The paper ID is identification information for identifying the paper data.

The apparatus information described in individual pieces of paper data includes expressive variations. That is, a formal name, another name, an abbreviation, or a model number may be described as apparatus information. In such a case, there is a possibility that customer information cannot appropriately be extracted. Thus, in the present embodiment, the occurrence of a problem caused by expressive variations can be suppressed by using the apparatus other names and the apparatus model numbers shown in the data table 141*a*, as described above. For example, when apparatus information "BM II" has been extracted from paper data, the extraction unit 112 refers to the apparatus other names shown in the data table 141*a*. If an apparatus another name that matches the extracted apparatus information is shown in the data table 141*a*, the extraction unit 112 specifies the apparatus ID and so forth associated with the apparatus another name in the data table 141*a* as customer information related to the apparatus. Accordingly, when the formal name of the apparatus is, for example, "Ball Milling II", it is possible to suppress the occurrence of a problem caused by expressive variations of the names "Ball Milling II" and "BM II".

If an apparatus name, an apparatus another name, or an apparatus model number that matches the extracted apparatus information is not shown in the data table 141a, the first analyzer 110 may update the data table 141a. That is, the first analyzer 110 updates the data table 141a so that the extracted apparatus information is included as a new apparatus name in the data table 141a. Specifically, the first analyzer 110 provides an administrator of the apparatus database 141 with a notification about the new apparatus name by email or the like. Accordingly, the administrator is prompted to check the new apparatus name, and is further prompted to add an apparatus model number, a vendor name, a price, and so forth related to the new apparatus name. As a result, the date table 141a is updated, and the occurrence of a problem caused by expressive variations of the apparatus information can further be suppressed.

The extraction unit 112 in the present embodiment extracts apparatus information from the paper data by using BERT as described above, and also may search for an apparatus name, an apparatus another name, an apparatus model number, and so forth shown in the data table 141a. Specifically, the extraction unit 112 searches the paper PDF for the individual apparatus names shown in the data table 141a, and if no apparatus name is found, the extraction unit 112 searches the paper PDF for the individual apparatus other names shown in the data table 141a. If no apparatus another name is found, the extraction unit 112 searches the paper PDF for the individual apparatus model numbers shown in the data table 141a. If an apparatus name, an apparatus another name, or an apparatus model number is found, the extraction unit 112 specifies the apparatus ID, the vendor name, the related apparatus ID, the price, and so forth associated with the apparatus name or the like in the data table 141a as customer information about the apparatus. Accordingly, customer information about the apparatus is extracted from the paper data.

FIG. 39 is a diagram illustrating an example of a data table held in the material database 142.

The material database 142 holds, for example, a data table 142a illustrated in FIG. 39. The data table 142a shows, for each of materials, pieces of information about the material. For example, the data table 142a shows, for each of materials, a material ID, a material name, a material another name, a vendor name, and a price of the material in association with each other. The material ID is identification information for identifying the material, the material name is a composition formula of the material, and the material another name is another name or an abbreviation different from the composition formula of the material. The vendor name is the name of the vendor of the material. The price is a price per gram of the material defined by the vendor of the material.

Specifically, the data table 142a shows, for the material having a material ID "3", the material ID "3", a material name "LiPON" of the material, a material another name "Lithium phosphorus oxynitride" of the material, a vendor name "Nakamura Material" of the material, and a price "1500 yen" per gram of the material.

When materials having the same material name are sold by different vendors, the prices of the materials may be different from each other. Thus, in the data table 142a, materials that have the same material name and that are sold by different vendors are associated with material IDs different from each other.

The data table 142a in the material database 142 is a data table that can be created on the basis of catalogs published by individual material vendors on web pages of the vendors. The data table 142a may be created automatically or manually. The lineups of materials sold by the material vendors are continuously updated. Thus, the data table 142a held in the material database 142 may be constantly updated to the latest state.

The extraction unit 112 in the present embodiment extracts material information from paper data, for example, the paper PDF illustrated in part (b) of FIG. 35, by using BERT similarly to the above. The extraction unit 112 then searches the data table 142a for a material name that matches the extracted material information. If the material name is not found, the extraction unit 112 searches the data table 142a for a material another name that matches the extracted material information. If the material name or the like is found through the search, the extraction unit 112 specifies the material ID, the vendor name, the price, and so forth associated with the material name or the like in the data table 142a as customer information related to the material. Accordingly, customer information about the material is extracted from the paper data. The extraction unit 112 then associates the paper ID of the paper data with the extracted customer information about the material.

The material information described in individual pieces of paper data includes expressive variations. That is, a formal name, another name, or an abbreviation may be described as material information. In such a case, there is a possibility that customer information cannot appropriately be extracted. Thus, in the present embodiment, the occurrence of a problem caused by expressive variations can be suppressed by using the material other names shown in the data table 142a, as described above. For example, when material information "Lithium phosphorus oxynitride" has been extracted from the paper data, the extraction unit 112 refers to the material other names shown in the table 142a. If a material another name that matches the extracted material information is shown in the data table 142a, the extraction unit 112 specifies the material ID and so forth associated with the material another name in the data table 142a as customer information. Accordingly, when the formal name of the material is, for example, "LiPON", it is possible to suppress the occurrence of a problem caused by expressive variations of the names "LiPON" and "Lithium phosphorus oxynitride".

If a material name or a material another name that matches the extracted material information is not shown in the data table 142a, the first analyzer 110 may update the data table 142a. That is, the first analyzer 110 updates the data table 142a so that the extracted material information is included as a new material name in the data table 142a. Specifically, the first analyzer 110 provides an administrator of the material database 142 with a notification about the new material name by email or the like. Accordingly, the administrator is prompted to check the new material name, and is further prompted to add an apparatus another name, a vendor name, a price, and so forth related to the new material name. As a result, the date table 142a is updated, and the occurrence of a problem caused by expressive variations of the material information can further be suppressed.

The extraction unit 112 in the present embodiment extracts material information from the paper data by using BERT as described above, and also may search for a material name or a material another name shown in the data table 142a. Specifically, the extraction unit 112 searches the paper PDF for the individual material names shown in the data table 142a, and if no material name is found, the extraction unit 112 searches the paper PDF for the individual material other names shown in the data table 142a. If a material name or a material another name is found, the extraction unit 112 specifies the material ID, the vendor name, the price, and so forth associated with the material name or the like in the data table 142a as customer information about the material. Accordingly, customer information about the material is extracted from the paper data.

FIG. 40 is a diagram illustrating an example of a data table held in the project database 143.

The project database 143 holds, for example, a data table 143a illustrated in FIG. 40. The data table 143a shows, for each of projects, pieces of information about the project. For example, the data table 142a shows, for each of projects, a project ID, a project name, a project another name, a project identification number, a starting year, an ending year, and a budget amount of the project in association with each other. The project ID is identification information for identifying the project, the project name is the name of the project, and the project another name is another name or an abbreviation different from the name of the project. The project identification number is an identification number of the project defined by a budget issuer of the project. The budget issuer may be an organization that pays the budget or an organization that determines the budget. The starting year is the year in which the project is started and which is defined by the issuer. The ending year is the year in which the project is ended and which is defined by the issuer. The budget amount is the budget of the project defined by the issuer.

Specifically, the data table 143a shows, for the project having a project ID "1", the project ID "1", a project name "Fund of material research" of the project, a project another name "MAT" of the project, a project identification number "234-3344" of the project, a starting year "2018" of the project, an ending year "2020" of the project, and a budget amount "20,000,000 yen" of the project.

The data table 143a in the project database 143 is a data table that can be created on the basis of information on individual projects, such as national projects, published on web pages or the like by support organizations that support research organizations. The data table 143a may be created automatically or manually. The information on projects is continuously updated, and thus the date table 143a held in the project database 143 may be constantly updated to the latest state.

The extraction unit 112 in the present embodiment extracts project information from paper data, for example, the paper PDF illustrated in FIG. 36, by using BERT similarly to the above.

Here, projects may be different from each other in the format or pattern of the project identification number. Thus, the extraction unit 112 in the present embodiment determines, after extracting the project information, whether the project information matches the individual patterns predetermined for the project identification number. For example, the patterns of a project identification number include a pattern in which "No." is located immediately before a numeral, such as "No. 1234", a pattern in which numerals are separated by a hyphen, such as "1233-3333", and a pattern in which alphabets and numerals are mixed, such as "AB1234". If the extraction unit 112 determines that the project information extracted from the paper matches any one of the patterns described above, the extraction unit 112 classifies the project information to a project identification number. On the other hand, if the extraction unit 112 determines that the project information extracted from the paper does not match any of the patterns described above, the extraction unit 112 classifies the project information to a project name or a project another name.

If the extracted project information has been classified to a project name or a project another name, the extraction unit 112 searches the data table 143a for a project name that matches the project information. If the project name is not found, the extraction unit 112 searches the data table 143a for a project another name that matches the extracted project information. If the project name or the like is found through the search, the extraction unit 112 specifies the project ID, the starting year, the ending year, the budget amount, and so forth associated with the project name or the like in the data table 143a as customer information about the project. Similarly, if the extracted project information has been classified to a project identification number, the extraction unit 112 searches the data table 143a for a project identification number that matches the project information. If the project identification number is found through the search, the extraction unit 112 specifies the project ID, the starting year, the ending year, the budget amount, and so forth associated with the project identification number in the data table 143a as customer information about the project. Accordingly, customer information about the project is extracted from the paper data.

The extraction unit 112 in the present embodiment extracts project information from paper data by using BERT as described above, and may search for a project name, a project another name, a project identification number, and so forth shown in the data table 143a. Specifically, the extraction unit 112 searches the paper PDF for the individual project names shown in the data table 143a, and if no project name is found, the extraction unit 112 searches the paper PDF for the individual project other names shown in the data table 143a. If no project another name is found, the extraction unit 112 searches the paper PDF for the individual project identification numbers shown in the data table 143a. If a project name or the like is found, the extraction unit 112 specifies the project ID, the starting year, the ending year, the budget amount, and so forth associated with the project name or the like in the data table 143a as customer information about the project. Accordingly, customer information about the project is extracted from the paper data.

FIG. 41 is a diagram illustrating an example of a data table held in the unit dictionary database 144.

The unit dictionary database 144 holds, for example, a data table 144a illustrated in FIG. 41. The data table 144a shows unit symbols used for units of weight and numerical notations corresponding to the unit symbols in association with each other. The unit symbols include "g", "mg", and "μg". The numerical notation corresponding to the unit symbol "g" is "1", the numerical notation corresponding to the unit symbol "mg" is "0.001", and the numerical notation corresponding to the unit symbol "μg" is "0.000001". These numerical notations are used to convert weights expressed by the unit symbols "mg", "μg", and the like into weights expressed in the unit symbol "g", that is, grams.

The extraction unit 112 in the present embodiment extracts the weight of a material notated by the unit symbol "g" from paper data, specifically the paper PDF, by using the date table 144a. That is, the extraction unit 112 extracts the weight of a material in grams from the paper data. Specifically, the extraction unit 112 searches the paper data for each of the unit symbols shown in the data table 144a. If any unit symbol is found, the extraction unit 112 extracts the unit symbol and the numerical value located immediately before the unit symbol from the paper data. The extraction unit 112 then refers to the numerical notation associated with the extracted unit symbol in the data table 144a, and multiplies the numerical value of the numerical notation by the numerical value extracted from the paper PDF. Accordingly, the extraction unit 112 calculates the weight notated by the unit symbol "g", that is, the amount in grams, of the material. As a result, the amount in grams of the material is extracted from the paper PDF. For example, when a unit symbol "mg" is found in paper data, the extraction unit 112 extracts the unit symbol "mg" and the numerical value "1" located immediately before the unit symbol "mg" from the paper data. That is, "1 mg" is extracted. The extraction unit 112 then refers to the numerical notation "0.001" associated with the extracted unit symbol "mg" in the date table 144a. Subsequently, the extraction unit 112 multiplies the numerical value "0.001" of the numerical notation by the numerical value "1" to calculate an amount "0.001" in grams, which is the weight of the material notated by the unit symbol "g". As a result, the amount in grams "0.001 g" is extracted from the paper PDF.

In addition, the extraction unit 112 extracts customer information such as a material ID from the paper data by using the material database 142 as described above. Furthermore, the extraction unit 112 extracts the amount in grams of a material from the paper data by using the unit dictionary database 144. The extraction unit 112 associates the amount in grams and the material ID extracted from the same paper data with each other. Accordingly, the paper ID of the paper data, the material ID, and the amount in grams are associated with each other. The amount in grams associated with the material ID is handled as customer information, similarly to the material ID.

When material IDs and amounts in grams are extracted from the same paper data, the material IDs and the amounts in grams may be associated with each other, that is, paired with each other, on the basis of the positions where material information, unit symbols, and the like are described in the paper data. For example, the extraction unit 112 specifies a unit symbol and a numerical value closest to a position where material information corresponding to a material ID is described, and associates the amount in grams corresponding to the unit symbol and the numerical value with the material ID.

FIG. 42 is a diagram illustrating an example of an organization identification table and an author identification table.

The extraction unit 112 generates, for example, an organization identification table T1 illustrated in part (a) of FIG. 42 and an author identification table T2 illustrated in part (b) of FIG. 42 as attached data of the customer database 145, and stores the tables in the customer database 145.

Specifically, after extracting an organization name from the paper bib, for example, the extraction unit 112 determines an organization ID for the organization name and includes the organization ID and the organization name in the organization identification table T1 in association with each other. The organization ID associated with the organization name may be determined, for example, in accordance with the order in which the organization name was extracted.

The organization identification table T1 shows, for each of organizations, an organization ID which is identification information of the organization and an organization name which is the name of the organization in association with each other. For example, the organization identification table T1 shows an "organization ID "1" and an organization name "A University" of an organization having the organization ID "1" in association with each other.

In addition, for example, after extracting an author name from the paper bib, the extraction unit 112 determines an author ID for the author name and includes the author ID and the author name in the author identification table T2 in association with each other. The author ID associated with the author name may be determined, for example, in accordance with the order in which the author name was extracted.

The author identification table T2 shows, for each of authors, an author ID which is identification information of the author and an author name which is the name of the author in association with each other. For example, the author identification table T2 shows, for an author having an author ID "1", the author ID "1" of the author and an author name "K. Sasaki" of the author in association with each other.

Scientific and technical papers are often created by authors.

In addition, an author may belong to organizations, or each of authors may belong to different organizations, such as a university and a company. In this case, a published paper of each author is searched for, and text information of the paper found through the search is used. Accordingly, an organization (a university, a company, or the like) to which the author belongs can be specified.

In a case where a person graduates from a university as a student and enters a company as a researcher, the student or the researcher may publish papers in different organizations as an author. When an author has moved from an organization to another organization, it may be impossible to specify the author on his/her papers because the organization to which the author belongs is different although the author name is identical.

Thus, the extraction unit 112 may include a code for uniquely identifying a person, such as an open researcher and contributor ID (ORCID), in the author identification table T2 in association with an author name. This makes it is possible to address a problem of not being able to specify an author having an identical author name when the author publishes papers in individual organizations. When an ORCID is included in paper data in the present embodiment, the extraction unit 112 may extract the ORCID from the paper data.

In recent years, a list of published papers or a researcher's history may be disclosed on a website or a social networking service (SNS) of the researcher or a laboratory to which the researcher belongs. Thus, a paper title extracted from a paper may be searched for by web search to find a website of a researcher who wrote the paper, and the researcher may be identified from a list of published papers or a history disclosed on the website. An author of a paper may be specified by searching a paper search site, such as "Google (registered trademark) Scholar", for a paper title.

FIG. 43A is a diagram illustrating an example of a data table stored in the customer database 145.

The customer database 145 stores, for example, a data table 145a illustrated in FIG. 43A. The data table 145a includes, for each of pieces of paper data, a data set about the piece of paper data. The data set about the piece of paper data indicates a paper ID, an author list, an organization list, apparatus-related information, project-related information, material-related information, and a publication month of the paper data in association with each other. The paper ID is identification information for identifying the paper data. The author list shows an author ID corresponding to each of at least one author name described in the paper data in a list format. The organization list shows an organization ID corresponding to each of at least one organization name described in the paper data in a list format. The apparatus-related information indicates, for each of at least one piece of apparatus information described in the paper data, a combination of an apparatus ID of an apparatus specified by the apparatus information and a price of the apparatus in a dictionary format. The project-related information indicates, for each of at least one piece of project information described in the paper data, a combination of a project ID of a project specified by the project information and a budget amount of the project in a dictionary format. The material-related information indicates, for each of at least one piece of material information described in the paper data, a combination of a material ID of a material specified by the material information and an amount in grams of the material in a dictionary format. The publication month is a month in which the paper data was published or issued and includes the publication date or the issue date described above.

Upon downloading paper data from the paper database 130, the extraction unit 112 in the present embodiment assigns a paper ID to the paper data. The extraction unit 112 then extracts a publication date or an issue date from the paper bib of the paper data, and specifies a month including the publication date or the issue date as a publication month. Furthermore, the extraction unit 112 extracts individual pieces of customer information from the paper data in the manner described above, by using the apparatus database 141, the material database 142, the project database 143, and the unit dictionary database 144. After extracting an organization name from the paper bib of the paper data, the extraction unit 112 specifies an organization ID associated with the organization name in the organization identification table T1. Similarly, after extracting an author name from the paper bib of the paper data, the extraction unit 112 specifies an author ID associated with the author name in the author identification table T2.

The extraction unit 112 generates a data set of the paper data by using the paper ID assigned to the paper data, the organization ID and the author ID specified for the paper data, individual pieces of customer information extracted from the paper data, and the publication month specified from the paper data.

Specifically, the extraction unit 112 includes, for example, a paper ID "1" assigned to the paper data and a publication month "June 2019" specified from the paper data in the data set of the paper data. Furthermore, the extraction unit 112 extracts at least one author name from the paper bib of the paper data having the paper ID "1". The extraction unit 112 selects, for each of the extracted at least one author name, an author ID associated with the author name in the author identification table T2 in part (b) of FIG. 42. The extraction unit 112 then generates an author list including the selected at least one author ID, for example, [1, 2], and includes the author list [1, 2] in the data set of the paper data. The author list [1, 2] includes an author ID "1" and an author ID "2".

Similarly, the extraction unit 112 extracts at least one organization name from the paper bib of the paper data having the paper ID "1". The extraction unit 112 selects, for each of the extracted at least one organization name, an organization ID associated with the organization name in the organization identification table T1 in part (a) of FIG. 42. The extraction unit 112 then generates an organization list including the selected at least one organization ID, for example, [1], and includes the organization list [1] in the data set of the paper data. The organization list [1] includes an organization ID "1".

Furthermore, the extraction unit 112 generates apparatus-related information of the paper data by using the customer information about an apparatus extracted from the paper data in the above-described manner by using the apparatus database 141. For example, the extraction unit 112 combines apparatus IDs and prices extracted as customer information about apparatuses from the paper data having the paper ID "1", thereby generating apparatus-related information {(1: 2,000,000), (2:90,000)}. The extraction unit 112 then includes the generated apparatus-related information {(1:2, 000,000), (2:90,000)} in the data set of the paper data. The apparatus-related information {(1:2,000,000), (2:90,000)} includes a combination of an apparatus ID "1" and a price "2,000,000 yen" and a combination of an apparatus ID "2" and a price "90,000 yen".

Similarly, the extraction unit 112 generates project-related information of the paper data by using the customer information about a project extracted from the paper data in the above-described manner by using the project database 143. For example, the extraction unit 112 combines project IDs and budget amounts extracted as customer information about projects from the paper data having the paper ID "1", thereby generating project-related information {(2:20,000, 000), (3:90,000,000)}. The extraction unit 112 then includes the generated project-related information {(2:20,000,000), (3:90,000,000)} in the dataset of the paper data. The project-related information {(2:20,000,000), (3:90,000,000)} includes a combination of a project ID "2" and a budget amount "20,000,000 yen" and a combination of a project ID "3" and a budget amount "90,000,000 yen".

Similarly, the extraction unit 112 generates material-related information of the paper data by using the customer information about a material extracted from the paper data in the above-described manner by using the material database 142. For example, the extraction unit 112 combines a material ID and an amount in grams extracted as customer information about a material from the paper data having the paper ID "1", thereby generating material-related information {2:0.1}. The extraction unit 112 then includes the generated material-related information {2:0.1} in the data set of the paper data. The material-related information {2:0.1} includes a combination of a material ID "2" and an amount in grams "0.1 g".

In this way, the extraction unit 112 in the present embodiment generates, for each of downloaded pieces of paper data, a data set of the piece of paper data. The extraction unit 112 then stores these data sets in the customer database 145. Accordingly, the data table 145a made up of these data sets is stored in the customer database 145. Paper data is continuously published or issued. Thus, the extraction unit 112 periodically generates a data set to maintain the data table 145a in the customer database 145 in the latest state.

FIG. 43B is a diagram illustrating another example of a data table stored in the customer database 145.

The customer database 145 may store a data table 145b illustrated in FIG. 43B. The data table 145b does not include the material-related information included in the data table 145a illustrated in FIG. 43A. The data table 145b is different from the data table 145a in this point. Other than that, the data table 145b shows the same information as that in the data table 145a.

For example, when the extraction unit 112 is unable to extract customer information about a material from paper data, the extraction unit 112 may generate a data set that does not include material-related information for the paper data, and may store the data set in the customer database 145. Accordingly, when customer information about a material has not been extracted from each of pieces of paper data, the data table 145*b* illustrated in FIG. 43B is stored in the customer database 145. Alternatively, the extraction unit 112 may store the data table 145*b*, which does not include material-related information, in the customer database 145 for apparatus vendors.

FIG. 43C is a diagram illustrating another example of a data table stored in the customer database 145.

The customer database 145 may store a data table 145*c* illustrated in FIG. 43C. The data table 145*c* does not include the apparatus-related information included in the data table 145*a* illustrated in FIG. 43A. The data table 145*c* is different from the data table 145*a* in this point. Other than that, the data table 145*c* shows the same information as that in the data table 145*a*.

For example, when the extraction unit 112 is unable to extract customer information about an apparatus from paper data, the extraction unit 112 may generate a data set that does not include apparatus-related information for the paper data, and may store the data set in the customer database 145. Accordingly, when customer information about an apparatus has not been extracted from each of pieces of paper data, the data table 145*c* illustrated in FIG. 43C is stored in the customer database 145. Alternatively, the extraction unit 112 may store the data table 145*c*, which does not include apparatus-related information, in the customer database 145 for material vendors.

As described above, in the present embodiment, the support apparatus 13 includes the first analyzer 110. The first analyzer 110 executes the following (b-1) to (b-3) with i=1 to n and generates a data set 1 to a data set n which are data sets. The data set 1 to the data set n are n data sets included in, for example, the data table 145*a* in the customer database 145 illustrated in FIG. 43A. Each of these data sets includes a paper ID and so forth. In (b-1), the first analyzer 110 extracts author-related information i from a document i, the author-related information i being information about at least one of an author of the document i or an organization to which the author belongs. For example, the author-related information i corresponds to the author list and the organization list in FIG. 43A. In (b-2), the first analyzer 110 extracts apparatus-related information i from the document i, the apparatus-related information i being information about an apparatus. For example, the apparatus-related information i corresponds to the apparatus-related information in FIG. 43A. In (b-3), the first analyzer 110 generates a data set i indicating the author-related information i and the apparatus-related information i in association with each other. That is, a data set including the above-described author list, organization list, and apparatus-related information is generated.

Accordingly, the data set 1 to the data set n are generated from the document 1 to the document n. The data set i indicates the author-related information i and the apparatus-related information i of the document i in association with each other. Thus, which author or organization uses which apparatus can be easily grasped by viewing the data set 1 to the data set n. Thus, the efficiency of business activities by apparatus vendors can be enhanced.

In addition, in the present embodiment, the first analyzer 110 further executes the following (b-4) with i=1 to n in the generation of the data sets. That is, in (b-4), the first analyzer 110 extracts material information i from the document i, the material information i being information about the type of a material. In (b-3), the first analyzer 110 generates the data set i further indicating the material information i in association with the author-related information i. For example, the material information i may be a material ID included in the material-related information in FIG. 43A.

Accordingly, the data set i indicates the author-related information i and the material information i of the document i in association with each other. Thus, which author or organization uses which material can be easily grasped by viewing the data set 1 to the data set n. Thus, the efficiency of business activities by material vendors can be enhanced.

In addition, in the present embodiment, the first analyzer 110 further executes the following (b-5) with i=1 to n in the generation of the data sets. That is, in (b-5), the first analyzer 110 extracts amount information i from the document i, the amount information i being information about the amount of the material. In (b-3), the first analyzer 110 generates the data set i further indicating the amount information i in association with the author-related information i. For example, the amount information i may be an amount in grams included in the material-related information in FIG. 43A.

Accordingly, the data set i indicates the author-related information i, the material information i, and the amount information i of the document i in association with each other. Thus, which author or organization uses which amount of which material can be easily grasped by viewing the data set 1 to the data set n. Thus, the efficiency of business activities by material vendors can further be enhanced.

In addition, in the present embodiment, the first analyzer 110 further executes the following (b-6) with i=1 to n in the generation of the data sets. That is, in (b-6), the first analyzer 110 extracts project-related information i from the document i, the project-related information i being information about a project supporting an author or organization. In (b-3), the first analyzer 110 generates the data set i further indicating the project-related information i in association with the author-related information i. For example, the project-related information i may be the project-related information in FIG. 43A.

Accordingly, the data set i indicates the author-related information i and the project-related information of the document i in association with each other. Thus, which author or organization is supported by which project can be easily grasped by viewing the data set 1 to the data set n. Thus, the solvency of the author or organization can be estimated, and the efficiency of business activities for the author or organization can further be enhanced.

Processing by Second Analyzer

The estimation unit 122 of the second analyzer 120 acquires the data table 145*a* from the customer database 145 and converts the data table 145*a* into an organization data table.

FIG. 44 is a diagram illustrating an example of an organization data table.

The estimation unit 122 sorts the individual data sets included in the data table 145*a* in the customer database 145 by the organization ID, thereby converting the data table 145*a* into, for example, an organization data table 145*x* illustrated in FIG. 44.

As illustrated in FIG. 44, the organization data table 145*x* shows, for each of organizations, an organization ID, apparatus-related information, project-related information, material-related information, and paper author information of the organization in association with each other.

The estimation unit 122 refers to the organization lists included in the data table 145a when converting the data table 145a in the customer database 145 into the organization data table 145x. The estimation unit 122 then selects organization IDs from the organization lists, for example, in ascending order. The estimation unit 122 combines all the pieces of apparatus-related information associated with an organization ID selected in the data table 145a, thereby generating one piece of new apparatus-related information in a dictionary format. For example, the estimation unit 122 combines all the pieces of apparatus-related information associated with an organization ID "2" in the data table 145a, thereby generating one piece of new apparatus-related information {(2:400,000), (3:4,000,000), (4:8,000,000), (5:12,000,000), (6:400,000)}.

Each of the data sets in the data table 145a may include the same apparatus ID associated with the same organization ID. In other words, individual pieces of paper data issued by the same organization may describe the same apparatus and the price thereof. In such a case, the estimation unit 122 calculates the sum of prices corresponding to the same apparatus ID included in the data sets, that is, the sum of prices of the same apparatuses described in the individual papers. For example, it is assumed that a data set having an organization ID "2" and a paper ID "1" and a data set having the same organization ID "2" and another paper ID "2" each include {1:1,000,000} as apparatus-related information in the data table 145a. That is, the paper data having the paper ID "1" and the paper data having the paper ID "2" issued by the organization having the organization ID "2" describe an apparatus having an apparatus ID "1" and a price "1,000,000 yen" of the apparatus. In such a case, the estimation unit 122 calculates the total price "1,000,000 yen+1,000,000 yen=2,000,000 yen" of the price "1,000,000 yen" corresponding to the apparatus ID "1" included in the data sets. Accordingly, the estimation unit 122 generates one piece of new apparatus-related information {1:2,000,000}.

In this way, the total price of apparatuses used in experiments in papers is calculated for each organization ID, and thus the types and the number of apparatuses purchased by each organization can be grasped. For example, when the total price of apparatuses A exceeds the total price of apparatuses B in organization X, it can be determined that the demand for apparatuses A is higher than that for apparatuses B in organization X.

Subsequently, the estimation unit 122 combines all the pieces project-related information associated with the organization ID selected in the data table 145a, thereby generating one piece of new project-related information in a dictionary format. For example, the estimation unit 122 combines all the pieces of project-related information associated with the organization ID "2" in the data table 145a, thereby generating one piece of new project-related information {(2:400,000), (3:4,000,000), (4:8,000,000), (5:12,000,000), (6:400,000)}.

Subsequently, the estimation unit 122 combines all the pieces of material-related information associated with the organization ID selected in the data table 145a, thereby generating one piece of new material-related information in a dictionary format. For example, the estimation unit 122 combines all the pieces of material-related information associated with the organization ID "2" in the data table 145a, thereby generating one piece of new material-related information {1:0.1, 2:0.4, 3:0.7}.

Each of the data sets in the data table 145a may include the same material ID associated with the same organization ID. In other words, individual pieces of paper data issued by the same organization may describe the same material and the weight thereof. In such a case, the estimation unit 122 calculates the sum of amounts in grams corresponding to the same material ID included in the data sets, that is, the sum of weights of the same materials described in the individual papers. For example, it is assumed that a data set having an organization ID "2" and a paper ID "1" and a data set having the same organization ID "2" and another paper ID "2" each include {1:0.1} and {1:0.2} as material-related information in the data table 145a. That is, the paper data having the paper ID "1" issued by the organization having the organization ID "2" describes a material having a material ID "1" (for example, LiPON) and a weight "0.1 g" of the material. Further, the paper data having the other paper ID "2" issued by the organization having the same organization ID "2" describes the material having the material ID "1" (for example, LiPON) and a weight "0.2 g" of the material. In such a case, the estimation unit 122 calculates the total amount in grams "0.1 g+0.2 g=0.3 g" of the amounts in grams "0.1 g" and "0.2 g" corresponding to the material ID "1" included in the data sets. Accordingly, the estimation unit 122 generates one piece of new material-related information {1:0.3}.

In experimental data in scientific and technical papers, reproducibility of experiments is important. Even in an experiment of a synthesis process, results of multiple experiments are often described in paper data rather than a result of a single experiment. Thus, regarding the amount in grams of a material used in an experiment of a synthesis process, the support apparatus 13 may extract the amount in grams of a material and the number of experiments from paper data, and may calculate the product thereof as the amount in grams of the material used in the experiments of the synthesis process. When the number of experiments is not described in paper data, the number of experiments may be estimated by using the number of points plotted in a graph, a table, or the like.

In this way, the sum of amounts in grams of a material used in experiments in papers is calculated for each organization ID, and thus the types and amounts of materials purchased by each organization can be grasped. For example, when the total amount in grams of material A exceeds the total amount in grams of material B in organization X, it can be determined that the demand for material A is higher than that for material B in organization X.

Subsequently, the estimation unit 122 combines all pairs of a paper ID and an author list associated with the organization ID selected in the data table 145a, thereby generating paper author information. For example, the estimation unit 122 combines all pairs of a paper ID and an author list associated with the organization ID "2" in the data table 145a, thereby generating paper author information {2: [2, 3], 3: [3]}. The paper author information includes a pair of the paper ID "2" and the author list [2, 3], and a pair of the paper ID "3" and the author list [3].

The estimation unit 122 then associates the selected organization ID with the apparatus-related information, project-related information, material-related information, and paper author information generated in the above-described manner. Such association is performed for each of the organization IDs, and thus the organization data table 145x illustrated in FIG. 44 is generated.

Estimation by Estimation Unit

The estimation unit 122 estimates a purchase probability for a material, a solvency for the material, and a profit ratio for the material of each of organizations, and generates information indicating a result of the estimation as material estimation information, by using, for example, the organization data table 145x illustrated in FIG. 44. Similarly, the estimation unit 122 estimates a purchase probability for an apparatus and a solvency for the apparatus of each of the organizations, and generates information indicating a result of the estimation as apparatus estimation information, by using, for example, the organization data table 145x illustrated in FIG. 44.

The purchase probability for a material is a value representing the strength of an intention to purchase the material of an organization as a customer. Similarly, the purchase probability for an apparatus is a value representing the strength of an intention to purchase the apparatus of an organization as a customer.

The profit ratio for the material is a ratio between a price per gram of the material and a profit included in the price.

The solvency for the material and the solvency for the apparatus are indices indicating the financial status of a customer which is an organization. By estimating such a solvency, a vendor of materials or apparatuses is able to grasp the financial status of an organization as a customer. As a result, the vendor is able to enhance the efficiency of business activities by narrowing down the types of materials or apparatuses.

FIG. 45A is a diagram illustrating an example of an estimation result regarding materials obtained by the estimation unit 122.

The estimation unit 122 generates material estimation information of each of organizations by using, for example, the organization data table 145x illustrated in FIG. 44, as described above.

For example, the estimation unit 122 extracts pieces of extracted information shown in the organization data table 145x. Each of the pieces of extracted information is a combination of an organization ID and a material ID included in the material-related information associated with the organization ID. The estimation unit 122 then generates, for each piece of extracted information, material estimation information for a material having the material ID included in the piece of extracted information in the organization having the organization ID included in the piece of extracted information. For example, as illustrated in FIG. 45A, the estimation unit 122 estimates a purchase probability, a solvent, and a profit ratio for the material having a material ID "3" in the organization having an organization ID "1". A combination of the organization ID "1" and the material ID "3" is extracted information, and the estimated purchase probability, solvent, and profit ratio are included in the material estimation information.

In the estimation of the purchase probability for the material, the estimation unit 122 converts the sum of the amounts in grams associated with the extracted information of an estimation target in the organization data table 145x into a total price, and estimates the total price as the purchase probability.

In a specific example of estimation of a purchase probability, the extracted information of an estimation target is a combination of an organization ID "1" and a material ID "2". In this case, the estimation unit 122 derives, from the organization data table 145x, the sum of amounts in grams of the material having the material ID "2" used in the organization having the organization ID "1". In the example in FIG. 44, the estimation unit 122 derives a total amount in grams "0.1 g". The estimation unit 122 then refers to the price "4000 yen" per gram of the material associated with the material ID "2" in the data table 142a in the material database 142. The estimation unit 122 multiplies the price "4000 yen" per gram of the material by the derived total amount in grams "0.1 g", thereby deriving the total price "400 yen" of the material having the material ID "2". Accordingly, the total price "400 yen" described above is estimated as the purchase probability for the material having the material ID "2" in the organization having the organization ID "1".

Here, the estimation unit 122 may convert the purchase probability expressed by a numerical value as a total price into a purchase probability expressed by any one of three levels "low", "medium", and "high". For example, in response to an input operation to the input unit 121 by the user of the second analyzer 120, the estimation unit 122 acquires a first threshold and a second threshold of the purchase probability from the input unit 121. If the above-described total price is lower than the first threshold, the estimation unit 122 converts the purchase probability expressed by the total price into a purchase probability expressed by the level "low". If the above-described total price is higher than or equal to the first threshold and lower than the second threshold, the estimation unit 122 converts the purchase probability expressed by the total price into a purchase probability expressed by the level "medium". If the above-described total price is higher than or equal to the second threshold, the estimation unit 122 converts the purchase probability expressed by the total price into a purchase probability expressed by the level "high".

Subsequently, in the estimation of the solvency for the material, the estimation unit 122 estimates, as the solvency, the total amount of the budget amounts in the project-related information associated with the extracted information of the estimation target in the organization data table 145x. That is, the estimation unit 122 estimates, as the solvency, the total amount of the budget amounts in the project-related information associated with the organization ID included in the extracted information of the estimation target.

In a specific example of estimation of a solvent, the extracted information of an estimation target includes an organization ID "1". In this case, the estimation unit 122 derives the project-related information of the organization ID "1" from the organization data table 145x. In the example in FIG. 44, the estimation unit 122 derives project-related information {(2:20,000,000), (3:90,000,000)}. The estimation unit 122 then estimates, as the solvency of the organization having the organization ID "1", the total amount "110,000,000 yen" of the budget amounts.

Similarly to the above, the estimation unit 122 may convert the solvency expressed by a numerical value as the total price into a solvency expressed by any one of three levels "low", "medium", and "high".

Subsequently, in the estimation of the profit ratio for the material, the estimation unit 122 estimates, as the profit ratio, the ratio between the price per gram of the material having the material ID included in the extracted information of the estimation target and a profit included in the price. The profit is an amount obtained by subtracting the cost price per gram of the material from the price per gram of the material. That is, the estimation unit 122 estimates, as the above-described ratio, the profit ratio for the material having the material ID included in the extracted information in the organization having the organization ID included in the extracted information. Specifically, the estimation unit 122 refers to the data table 142a in the material database 142 and derives, from the data table 142a, the price per gram of the material having the material ID included in the extracted information of the estimation target. Furthermore, in response to an input operation to the input unit 121 by the user of the second analyzer 120, the estimation unit 122 acquires the cost price per gram of the material having the material ID from the input unit 121. The estimation unit 122 then divides the difference between the price and cost price per gram of the material by the price per gram of the material, thereby calculating a profit ratio.

In a specific example of estimation of a profit ratio, the extracted information of an estimation target includes a material ID "2". In this case, the estimation unit 122 derives the price "4000 yen" per gram of the material having the material ID "2" from the data table 142a in the material database 142. Furthermore, in response to an input operation to the input unit 121 by the user of the second analyzer 120, the estimation unit 122 acquires the cost price "2000 yen" per gram of the material having the material ID from the input unit 121. The estimation unit 122 then divides the difference "2000 yen" between the price "4000 yen" and the cost price "2000 yen" per gram of the material by the price "4000 yen" per gram of the material, thereby calculating a profit ratio "0.5". Accordingly, "0.5" is estimated as the profit ratio for the material having the material ID "2" in the organization having the organization ID "1".

Similarly to the above, the estimation unit 122 may convert the profit ratio expressed by a ratio into a profit ratio expressed by any one of three levels "low", "medium", and "high".

In the case of estimating a profit ratio, the estimation unit 122 may refer to sale conditions stored in the sale database 147 and may estimate the profit ratio on the basis of the sale conditions. For example, if a total price indicated by a purchase probability satisfies the sale conditions, the estimation unit 122 discounts the price per gram of a material. Specifically, the estimation unit 122 discounts the price by a predetermined discount rate (for example, 10%). The estimation unit 122 then estimates the profit ratio on the basis of the discounted price.

The estimation unit 122 stores, in the estimation result database 148 included in the database group 140, the material estimation information including the purchase probability, solvency, and profit ratio for the material estimated in the above-described manner. Further, the estimation unit 122 may output the material estimation information to a presentation device such as a display, for example, and may present the material estimation information to the user of the second analyzer 120 in a table format as in the example in FIG. 45A. Accordingly, the user is able to grasp which material is likely to be purchased by which organization, by referring to the material estimation information. Furthermore, the user is able to observe, from a bird's eye view, how much profit can be expected for each organization if the material is sold.

The estimation unit 122 may acquire a material ID from the input unit 121 in response to an input operation to the input unit 121 performed by the user of the second analyzer 120. In this case, the estimation unit 122 may present to the user only the material estimation information associated with the material ID. Accordingly, only the material estimation information related to the material sold by the material vendor to which the user belongs is presented to the user. Thus, presentation of information unnecessary to the material vendor can be suppressed, and necessary information can be provided to the user in an easy-to-view manner.

FIG. 45B is a diagram illustrating another example of an estimation result regarding materials obtained by the estimation unit 122.

The estimation unit 122 may reflect a web search result on the purchase probability for the material described above. In this case, the estimation unit 122 generates, for each of pieces of extracted information, material estimation information including a purchase probability, a web-search-reflected probability, a solvency, and a profit ratio as illustrated in FIG. 45B.

For example, after estimating the purchase probability in the organization having the organization ID included in the extracted information in the above-described manner, the estimation unit 122 specifies the name of the vendor of the material used by the organization by referring to the data table 142a in the material database 142. That is, the estimation unit 122 specifies the vendor name associated with the material ID included in the extracted information in the data table 142a. The estimation unit 122 then acquires the number of times of browsing of a website published by the company having the vendor name. The estimation unit 122 divides the acquired number of times of browsing by a predetermined reference number of times of browsing, thereby calculating a browsing ratio. The estimation unit 122 then multiplies the purchase probability expressed by the total price as described above by the browsing ratio, thereby calculating a web-search-reflected probability. The estimation unit 122 may convert the web-search-reflected probability expressed by the numerical value into a web-search-reflected probability expressed by any one of three levels "low", "medium", and "high", similarly to the purchase probability described above.

Such a web-search-reflected probability reflects the number of times of browsing of the website of the material vendor. The number of times of browsing includes the number of times an organization such as a university or a research institution has browsed the website to purchase materials. Thus, the web-search-reflected probability may be higher in accuracy than the purchase probability in which the web search result is not reflected. Thus, the user of the second analyzer 120 is able to more appropriately grasp the purchase probabilities of individual customers by referring to the web-search-reflected probability.

Figure 46:
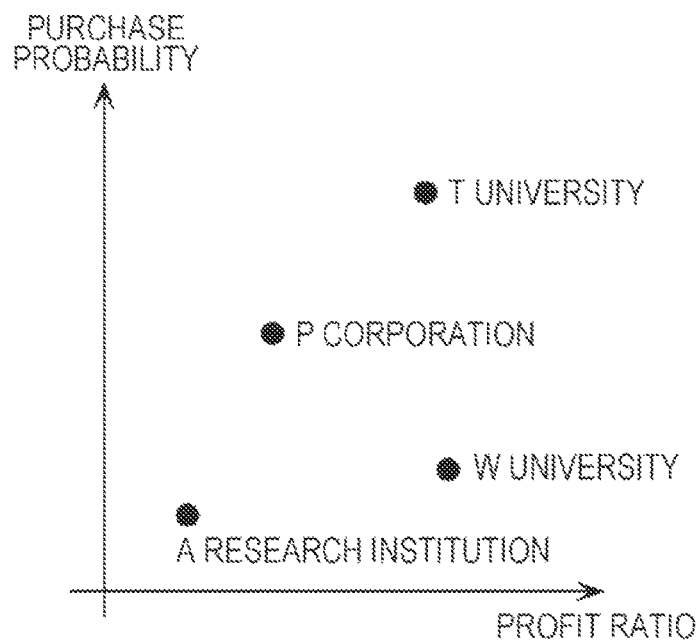
FIG. 46 is a diagram illustrating a display example of an estimation result regarding a material obtained by the estimation unit in the fourth embodiment.

FIG. 46 is a diagram illustrating a display example of an estimation result regarding a material obtained by the estimation unit 122.

As illustrated in FIG. 46, for example, the estimation unit 122 may display purchase probabilities and profit ratios of individual organizations in a graph format on a display. For example, the horizontal axis of the graph indicates profit ratio, and the vertical axis indicates purchase probability. In this graph, the purchase probabilities and the profit ratios of the individual organizations such as A Research Institution, P Corporation, T University, and W University are expressed by the positions of points.

By observing this graph, the user of the second analyzer 120 is able to multilaterally observe marketing for the individual organizations. For example, in the graph illustrated in FIG. 46, it is possible to intuitively grasp that the purchase probability of T University is the highest. Accordingly, if the user of the second analyzer 120 belongs to a material vendor, the user is able to determine that he/she can obtain the highest business efficiency in T University, among T University, P Corporation, W University, and A Research Institution.

In the example illustrated in FIG. 46, the estimation unit 122 displays a graph showing purchase probabilities and profit ratios, but may generate and display a graph showing purchase probabilities and solvencies or a graph showing profit ratios and solvencies. The estimation unit 122 may generate and display a three-axis graph showing a purchase probability, a solvency, and a profit ratio, instead of the two-axis graph as illustrated in FIG. 46.

Figure 47:
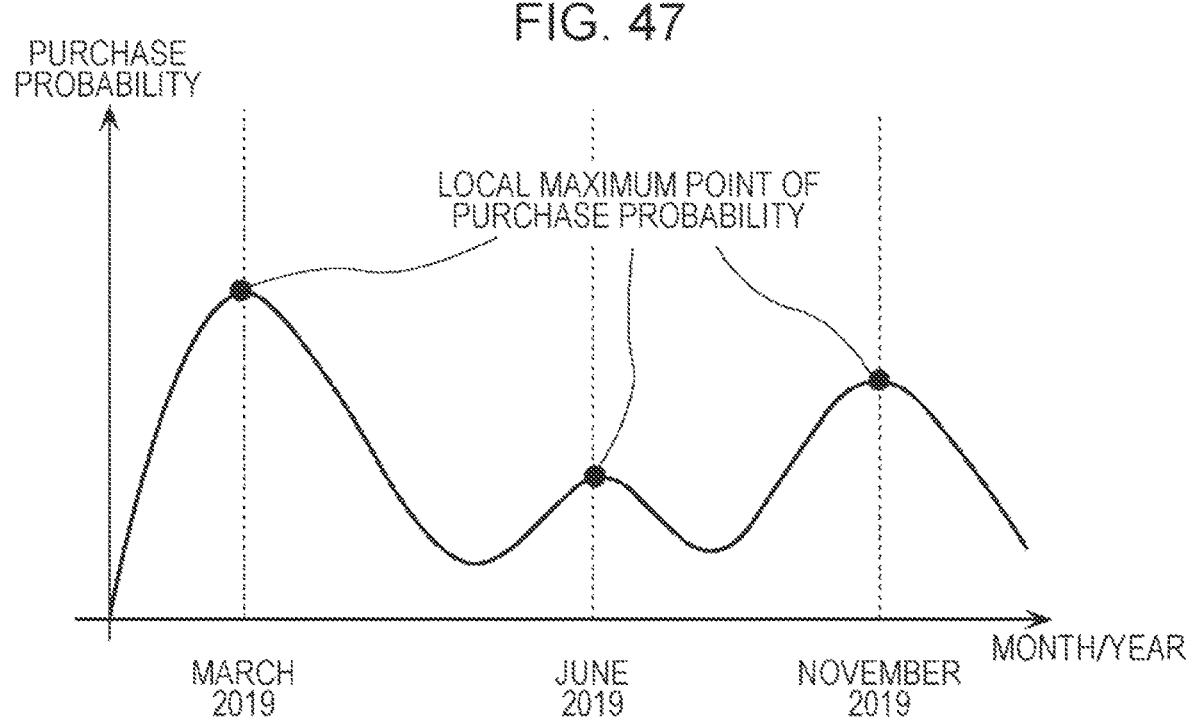
FIG. 47 is a diagram illustrating another example of an estimation result regarding a material obtained by the estimation unit in the fourth embodiment.

FIG. 47 is a diagram illustrating another example of an estimation result regarding a material obtained by the estimation unit 122.

The estimation unit 122 may derive a chronological change in the purchase probability for a material as a processing target in an organization as a processing target as illustrated in FIG. 47 by using the date table 145a in the customer database 145, and may display the chronological change on the display. For example, the estimation unit 122 specifies at least one combination of an amount in grams and a publication month associated with the organization ID "1" and the material ID "2" in the date table 145a. The organization ID "1" is an example of an organization ID for identifying the organization as the processing target, and the material ID "2" is an example of a material ID for identifying the material as the processing target.

For example, in the data table 145a illustrated in FIG. 43A, the estimation unit 122 specifies a combination of the amount in grams "0.1 g" and the publication month "June 2019". Furthermore, the estimation unit 122 specifies the price "4000 yen" per gram of the material associated with the material ID "2" by referring to the data table 142a in the material database 142. The estimation unit 122 then multiplies the amount in grams "0.1 g" by the price "4000 yen" specified as described above, thereby deriving the price "400 yen" as a purchase probability for the material having the material ID "2" in the organization having the organization ID "1". Accordingly, "400 yen" is derived as a purchase probability in the publication month "June 2019" for the material having the material ID "2" in the organization having the organization ID "1". The estimation unit 122 performs such derivation of a purchase probability on each of at least one combination specified as described above, thereby deriving a chronological change in the purchase probability for the material having the material ID "2" in the organization having the organization ID "1".

As described above, in the present embodiment, a chronological change in annual purchase probability for a certain material in a certain organization can be visualized. By reading a local maximum point of purchase probability from the chronological change, the time to perform business activities can be clarified. For example, in the example in FIG. 47, local maximum points of purchase probability are in March, June, and November of 2019. Thus, it is understood that it is preferable to perform business activities in March, June, and November every year, and business efficiency can be increased accordingly.

FIG. 48 is a diagram illustrating an example of an estimation result regarding apparatuses obtained by the estimation unit 122.

As described above, the estimation unit 122 generates apparatus estimation information of each of organizations by using, for example, the organization data table 145x illustrated in FIG. 44.

For example, the estimation unit 122 extracts pieces of extracted information shown in the organization data table 145x. Each of the pieces of extracted information is a combination of an organization ID and an apparatus ID included in the apparatus-related information associated with the organization ID. The estimation unit 122 may include a related apparatus ID corresponding to the apparatus ID in the extracted information. That is, the estimation unit 122 may include, in the extracted information, a related apparatus ID associated with the above-described apparatus ID in the data table 141a by referring to the data table 141a in the apparatus database 141.

The estimation unit 122 then generates, for each piece of extracted information, apparatus estimation information for the apparatus having the apparatus ID included in the piece of extracted information in the organization having the organization ID included in the piece of extracted information. For example, the estimation unit 122 estimates a purchase probability and a solvency for the apparatus having the apparatus ID "1" in the organization having the organization ID "1", as illustrated in FIG. 48. A combination of the organization ID "1" and the apparatus ID "1" is included in the extracted information, and the estimated purchase probability and solvency are included in the apparatus estimation information.

In the estimation of a purchase probability for an apparatus, the estimation unit 122 estimates, as the purchase probability of the apparatus, the sum of the prices of the apparatuses associated with the extracted information of the estimation target in the organization data table 145x.

In a specific example of estimation of a purchase probability, the extracted information of the estimation target includes a combination of an organization ID "1" and an apparatus ID "1". In this case, the estimation unit 122 derives the price of the apparatus having the apparatus ID "1" used in the organization having the organization ID "1" from the organization data table 145x. In the example in FIG. 44, the estimation unit 122 derives a price "2,000,000 yen" of the apparatus. Accordingly, the above-described price "2,000,000 yen" is estimated as the purchase probability for the apparatus having the apparatus ID "1" in the organization having the organization ID "1".

Similarly to the above, the estimation unit 122 may convert the purchase probability expressed by a numerical value as a price into a purchase probability expressed by any one of three levels "low", "medium", and "high".

In the estimation of a solvency for an apparatus, the estimation unit 122 estimates, as the solvency, the total amount of budget amounts in the project-related information associated with the extracted information of the estimation target in the organization data table 145x. That is, the estimation unit 122 estimates, as the solvency, the total amount of the budget amounts in the project-related information associated with the organization ID included in the extracted information of the estimation target. The solvency for the apparatus is estimated similarly to the solvency for a material.

The estimation unit 122 stores the apparatus estimation information including the purchase probability for the apparatus and the solvency for the apparatus estimated in the above-described manner in the estimation result database 148 included in the database group 140. Furthermore, the estimation unit 122 may output the apparatus estimation information to a presentation device such as a display, for example, and may present the apparatus estimation information to the user of the second analyzer 120 in a table format such as the example in FIG. 48. Accordingly, the user is able to grasp which apparatus is likely to be purchased by which organization by referring to the apparatus estimation information. In addition, the user is able to observe purchase probabilities of individual organizations from a bird's eye view, and to estimate a success probability of business by checking the solvencies. Furthermore, a related apparatus ID of the apparatus ID is simultaneously displayed. This allows flexible suggestions to be provided depending on the financial statuses of the organizations, for example, by suggesting a new model of an apparatus currently used by an organization, or suggesting an inexpensive model of an apparatus to an organization having a low solvency.

The estimation unit 122 may acquire an apparatus ID from the input unit 121 in response to an input operation performed on the input unit 121 by the user of the second analyzer 120. In this case, the estimation unit 122 may present to the user only the apparatus estimation information associated with the apparatus ID. Accordingly, only the apparatus estimation information about the apparatus sold by the apparatus vendor to which the user belongs is presented to the user. Thus, presentation of information unnecessary to the apparatus vendor can be suppressed, and necessary information can be provided to the user in an easy-to-view manner.

Figure 49:
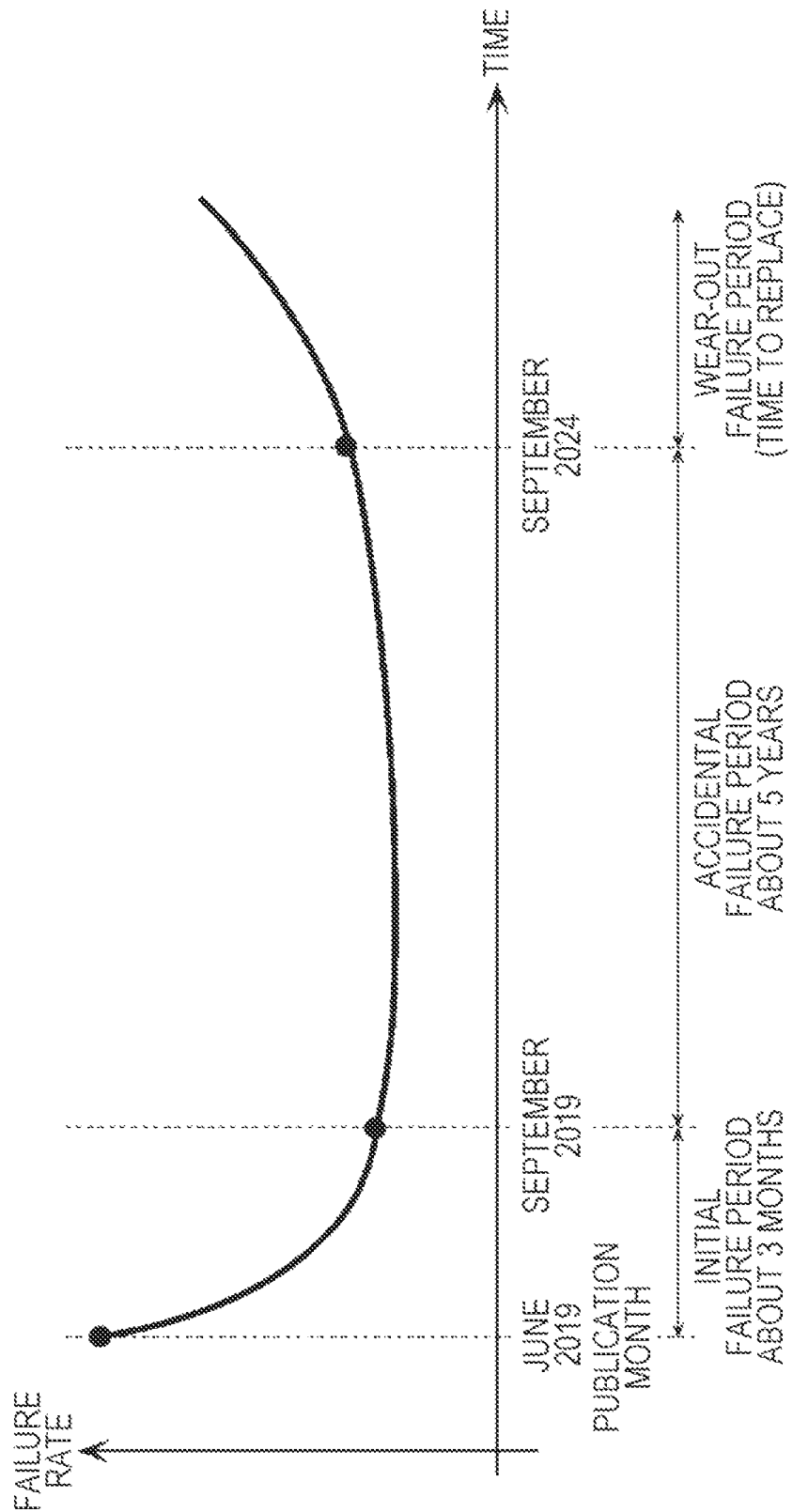
FIG. 49 is a diagram illustrating another example of an estimation result regarding an apparatus obtained by the estimation unit in the fourth embodiment.

FIG. 49 is a diagram illustrating another example of an estimation result regarding an apparatus obtained by the estimation unit 122.

The estimation unit 122 may estimate a chronological change in the failure rate of an apparatus, as illustrated in FIG. 49. For example, the estimation unit 122 specifies an organization ID and a publication month associated with the apparatus ID of the apparatus as an estimation target by referring to the data table 145a in the customer database 145. For example, if the apparatus ID of the apparatus as an estimation target is "1", the estimation unit 122 specifies the organization ID and the publication month associated with the apparatus-related information including the apparatus ID "1". When the data table 145a illustrated in FIG. 43A is referred to, the organization ID "1" and the publication month "June 2019" are specified.

Subsequently, the estimation unit 122 acquires, from the apparatus maintenance database 146, a failure rate curve associated with the apparatus ID of the apparatus as the estimation target. The failure rate curve indicates an initial failure period, an accidental failure period, and a wear-out failure period, and also indicates a temporal change in the failure rate in each of the periods. For example, the initial failure period is three months from the usage starting time of the apparatus, the accidental failure period is five years after the elapse of the initial failure period, and the wear-out failure period is the period after the elapse of the accidental failure period.

The estimation unit 122 sets the publication month specified in the above-described manner as the starting month of the change in the failure rate indicated by the acquired failure rate curve. For example, if the publication month is "June 2019", "June 2019" is set as the starting month of the change in the failure rate. Accordingly, the estimation unit 122 estimates a failure rate curve in which the failure rate changes from the starting month "June 2019", as a chronological change in the failure rate in the apparatus having the apparatus ID "1". Thus, the estimation unit 122 determines that the period from June 2019 to September 2019 is the initial failure period, the period from September 2019 to September 2024 is the accidental failure period, and the period from September 2024 is the wear-out failure period.

The estimation unit 122 stores, in the estimation result database 148, failure rate information including information indicating the chronological change in the failure rate of the apparatus estimated in this manner, the apparatus ID of the apparatus, and the organization ID specified in the above-described manner. In addition, the estimation unit 122 may output the failure rate information to a presentation device such as a display, for example, and may present the chronological change in the failure rate of the apparatus to the user of the second analyzer 120 in a graph format as in the example in FIG. 49.

As a result, the user of the second analyzer 120 is able to intuitively grasp when to provide a suggestion about the maintenance of the apparatus. A notification about maintenance may be provided to the user during the initial failure period and the wear-out failure period during which the failure rate of the apparatus is high.

In a scientific and technical paper published on an academic journal, there are a date on which the paper was submitted, a date on which a reviewer decided to record the paper, and a date on which the paper was published on the journal or the like. In particular, in an authoritative journal or the like, it may take one year or more from when an author submits a paper to when the paper is published. An apparatus described in a paper is purchased prior to the date on which the paper was submitted. Thus, the date on which the paper was submitted may be used instead of the above-described publication month.

In recent years, experimental results and the like may be published as archives on the Internet. The contents similar to those of the experimental results may be presented in an international conference or the like. Thus, with respect to a paper presented in an international conference or the like, archives may be searched on the Internet, and if experimental results similar to those described in the presented paper are published, the date in the archives may be used instead of the above-described publication month.

The same apparatus name may appear in each of scientific and technical papers created by the same author. Meanwhile, an apparatus used in experiments of a synthesis process for a material is expensive, and thus it is rare that a multiple number of such apparatuses are possessed. Thus, when the same apparatus name has been extracted from pieces of paper data, the date on which the oldest piece of paper data was published may be used instead of the above-described publication month.

Processing Flow

Figure 50A:
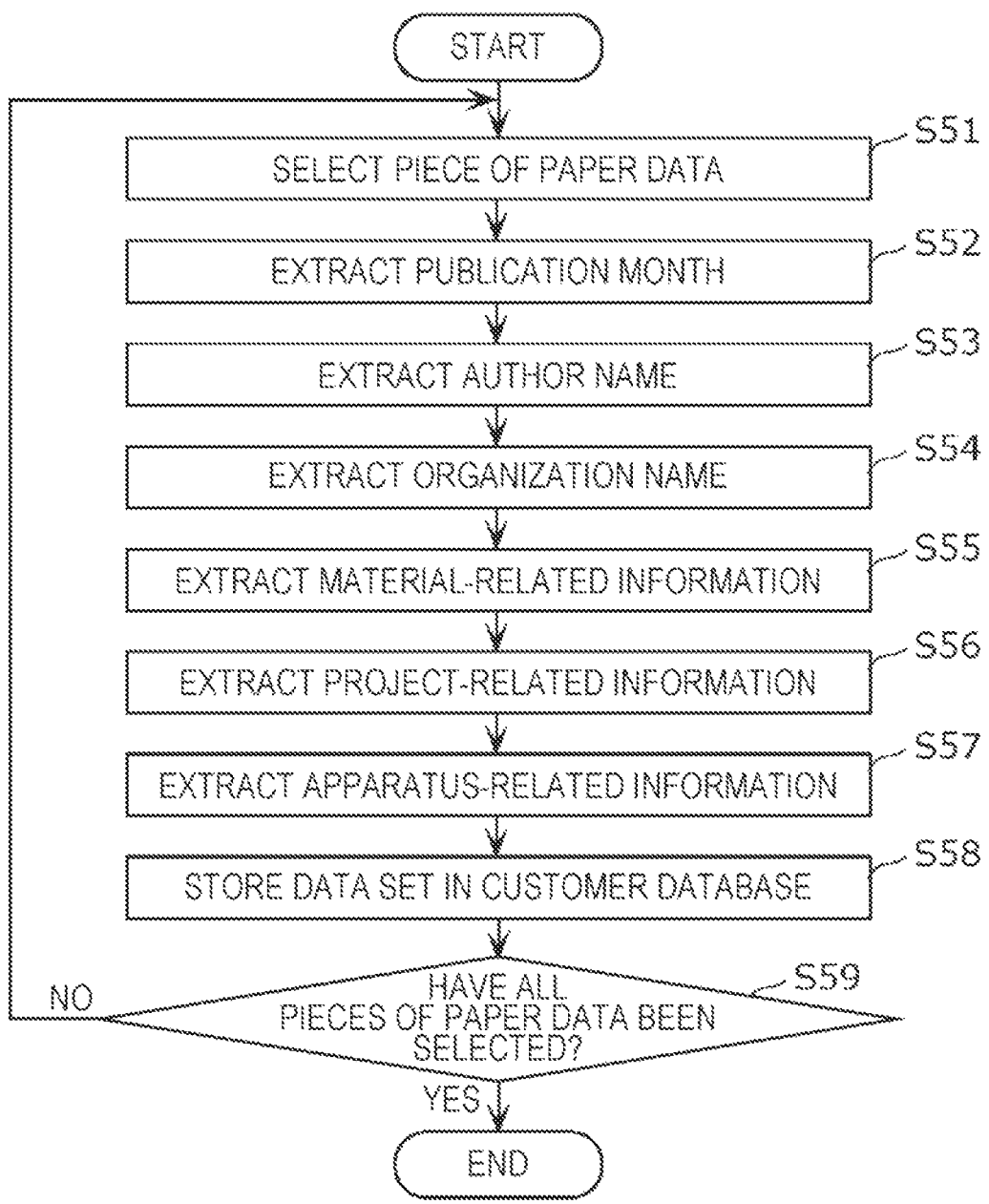
FIG. 50A is a flowchart illustrating an example of processing performed by an extraction unit in the fourth embodiment.

FIG. 50A is a flowchart illustrating an example of processing performed by the extraction unit 112.

The extraction unit 112 selects and downloads one of pieces of paper data held in the paper database 130 (step S51). Subsequently, the extraction unit 112 extracts a publication month of the piece of paper data from the paper bib of the piece of paper data (step S52). That is, the extraction unit 112 extracts an issue date or a publication date of the piece of paper data and specifies a publication month including the issue date or the publication date. Furthermore, the extraction unit 112 extracts, from the piece of paper data, an author name as an author ID (step S53) and an organization name as an organization ID (step S54). The author ID may be an ORCID. The extraction unit 112 may determine whether the extracted author name belongs to the organization having the extracted organization name. For example, the extraction unit 112 may search for a past document of the extracted author name, and may refer to data of the document to compare the extracted author name with the organization name.

Subsequently, the extraction unit 112 extracts material-related information (step S55), project-related information (step S56), and apparatus-related information (step S57) from the piece of paper data. To extract these pieces of information, the data table 142a in the material database 142, the data table 143a in the project database 143, and the data table 141a in the apparatus database 141 are used. Even if the piece of paper data includes expressive variations in the material information, the project information, and the apparatus information, the extraction unit 112 is capable of appropriately extracting the material-related information, the project-related information, and the apparatus-related information by referring to the above-described data tables.

Subsequently, the extraction unit 112 stores a data set including the pieces of information extracted in steps S52 to S57 in the customer database 145 in association with the paper ID of the piece of paper data selected in step S51 (step S58).

After step S58, the extraction unit 112 determines whether all the pieces of paper data held in the paper database 130 have been selected (step S59). If the extraction unit 112 determines that all the pieces of paper data have not been selected (NO in step S59), the extraction unit 112 repeatedly executes the processing from step S51. On the other hand, if the extraction unit 112 determines that all the pieces of paper data have been selected (YES in step S59), the extraction unit 112 ends the processing.

Figure 50B:
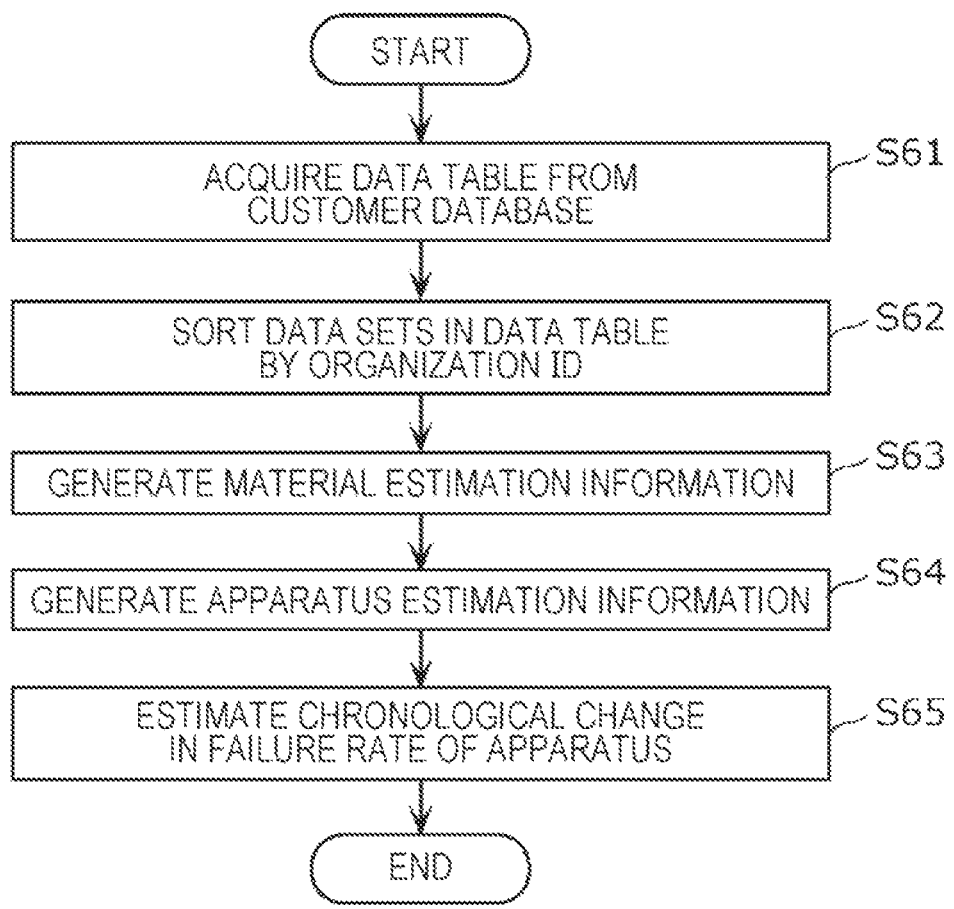
FIG. 50B is a flowchart illustrating an example of processing performed by the estimation unit in the fourth embodiment.

FIG. 50B is a flowchart illustrating an example of processing performed by the estimation unit 122.

The estimation unit 122 acquires the data table 145a from the customer database 145 (step S61). Subsequently, the estimation unit 122 sorts the individual data sets included in the data table 145a by the organization ID, thereby converting the data table 145a into the organization data table 145x (step S62).

Subsequently, the estimation unit 122 generates material estimation information (step S63) and further generates apparatus estimation information (step S64) by using the organization data table 145x. The estimation unit 122 then estimates a chronological change in the failure rate of an apparatus (step S65).

With the support apparatus 13 in the present embodiment, customer information can be efficiently extracted by focusing attention on an information medium, such as paper data which is reliably and continuously published by material researchers or the like. Furthermore, as a result of analyzing the extracted customer information, it is possible to provide information useful for business activities of vendors of materials or apparatuses.

In the present embodiment, paper data of scientific and technical papers or the like is used. Alternatively, reports, final reports, or the like of national projects or the like may be used. Reports of national projects often describe, as the results the projects, information about purchased apparatuses and materials. In particular, such reports are not limited in the number of pages in many cases and include many contents, unlike scientific and technical papers. On the other hand, scientific and technical papers are often limited in the number of pages in an international conference or an academic journal. Thus, when a project name or the like is described in paper data of a scientific and technical paper or the like, it is possible to collect information about apparatuses and materials purchased for experiments or the like of the paper data by searching text information of a final report or the like of the project. However, a national project is typically conducted over years in many cases. Thus, a final report of a national project or the like is often published at or after the ending year of the national project. On the other hand, a scientific and technical paper presented in an international conference or published on a technical journal is often published early compared with the foregoing final report.

Thus, the extraction unit 112 in the present embodiment first constructs apparatus-related information in the customer database 145 by using published paper data. When an experimental result indicated in the paper data is a research result of a project, the extraction unit 112 may update the apparatus-related information by using a report or the like published after the project has finished.

Although paper data is used in the present embodiment, other documents may be used instead of the paper data.

The first analyzer 110 in the present embodiment includes the synthesis process extraction unit 111, but the synthesis process extraction unit 111 need not necessarily be included. In this case, the paper data stored in the paper database 130 may include contents other than a synthesis process.

In the present embodiment, an issue date or a publication date may be extracted instead of a publication month and may be shown in the date table 145a in the customer database 145.

The support apparatus, the generation apparatus, and the analysis apparatus according to one or more aspects have been described above on the basis of the embodiments and modifications. The present disclosure is not limited to these embodiments and modifications. An embodiment implemented by applying various modifications conceived by those skilled in the art to the above-described embodiments and modifications, and an embodiment implemented by combining elements in different embodiments or different modifications may be included in the scope of the present disclosure without departing from the gist of the present disclosure.

For example, in each of the above-described embodiments and modifications, a document is a paper. Alternatively, a document may be a textbook, a magazine, a patent document, or the like.

In the first to third embodiments and the modifications described above, the synthesis process accumulation unit 201 accumulates synthesis processes generated by the synthesis process generation apparatus 100. Documents used to generate the synthesis processes may also be accumulated in association with the synthesis processes. In this case, the synthesis processes or a composite synthesis process can be displayed on the display unit 205, and the documents as a source of the synthesis processes can also be displayed on the display unit 205 in response to a user operation. Instead of accumulating a document in the synthesis process accumulation unit 201, information indicating the location where the document is stored may be accumulated in the synthesis process accumulation unit 201. The information indicating the location may be, for example, a uniform resource locator (URL) or a uniform resource identifier (URI).

In the first to third embodiments and the modifications described above, the combining unit 204 combines synthesis processes. These synthesis processes may be combined by being weighted. For example, the number of citations included in the bibliographic information of each of the synthesis processes may be used for weighting. That is, the combining unit 204 may specify the number of citations of each of synthesis processes obtained through a search, and may omit, among the synthesis processes, a predetermined number of synthesis processes from the target to be combined in ascending order of the number of citations.

In the first to third embodiments and the modifications described above, the generation unit 107 associates treatment words in the order of appearance in a document. Alternatively, the generation unit 107 may associate treatment words by using a dictionary indicating a relationship between a treatment word and another treatment word. The generation unit 107 may associate treatment words in accordance with a predetermined rule.

In the first to third embodiments and the modifications described above, a generated synthesis process and a composite synthesis process are graphed and displayed. Alternatively, the graphed synthesis process and composite synthesis process may be corrected by a user. For example, when the user finds an error in the synthesis process displayed on the display unit 205, the user corrects the error by operating the operation device 340. That is, in response to receipt of a signal indicating an operation result output from the operation device 340, the generation unit 107 changes the arrangement or order of treatment words included in the synthesis process, or changes association between a treatment word and a synthesis condition.

The user may correct the configuration of a composite synthesis process displayed on the display unit 205 by operating the operation device 340, for example. That is, in response to receipt of a signal indicating an operation result output from the operation device 340, the combining unit 204 deletes or changes treatment words or material words included in the composite synthesis process. After the configuration of the composite synthesis process has been corrected, the search unit 203 may search for a synthesis process that matches the material words and treatment words included in the corrected composite synthesis process. That is, re-searching for a synthesis process is performed. The combining unit 204 combines synthesis processes found through the re-searching, thereby newly generating a composite synthesis process and displaying the composite synthesis process on the display unit 205. The new composite synthesis process has the same configuration as that of the corrected composite synthesis process described above (i.e., the same material words and the same treatment words), and further includes an appropriate comprehensive synthesis condition and comprehensive characteristic value corresponding to the configuration.

In the first to third embodiments and the modifications described above, the association among material words, among treatment words, and among synthesis conditions in a composite synthesis flow is indicated by similar solid lines or arrows. However, the types of solid lines or arrows indicating the association may be changed in accordance with a search result of a synthesis flow. For example, in the composite synthesis flow illustrated in FIG. 16, the number of synthesis flows in which a treatment indicated by the treatment word "mix" is followed by a treatment indicated by the treatment word "heat" may be larger than the number of synthesis flows in which a treatment indicated by the treatment word "heat" is followed by a treatment indicated by the treatment word "mill". In this case, the combining unit 204 may make the thickness of the arrow extending from the treatment word "mix" to the treatment word "heat" larger than the thickness of the arrow extending from the treatment word "heat" to the treatment word "mill". Accordingly, the tendency of synthesis processes in individual documents can be grasped more clearly.

In the first to third embodiments and the modifications described above, bibliographic information includes none of a material word of a starting material, a material word of a target material, and a characteristic value of the target material, but may include these words and the value.

In the first to third embodiments and the modifications described above, the synthesis process generation apparatus 100 and the synthesis process analysis apparatuses 200, 240, and 250 are provided. These apparatuses may be included in one apparatus or may be individual apparatuses. For example, the synthesis process generation apparatus 100 and the synthesis process analysis apparatus 200, 240, or 250 may be connected to each other via a communication network, such as the Internet. The elements that are included in these apparatuses and that perform information processing may be constituted by one processor or circuit, or may be constituted by processors or circuits.

In the first to third embodiments and the modifications described above, the synthesis process generation apparatus 100 generates a synthesis process which is structured data. The generation of the synthesis process can also be referred to as processing of converting a synthesis process described in a natural language in a document into a synthesis process as graphable structured data as illustrated in FIG. 8. A synthesis process does not need to be described in a natural language in a document. For example, a synthesis process may be described in a document in a table format or the like.

In the first embodiment and the second modification described above, the combining unit 204 performs clustering. The clustering may be performed automatically or may be performed with a threshold being set by a user. For example, in the case of performing clustering on synthesis conditions of pressure "300 MPa", "250 MPa", "320 MPa", "450 MPa", and "460 MPa, the combining unit 204 accepts, for example, "400 MPa" as a threshold set by the user. Accordingly, the combining unit 204 divides a set of the synthesis conditions into a subset including "300 MPa", "250 MPa", and "320 MPa", and a subset including "450 MPa" and "460 MPa". Accordingly, the user is able to perform desired clustering.

In the embodiments and the modifications described above, each element may be constituted by dedicated hardware or may be implemented by executing a software program suitable for the element. Each element may be implemented as a result of a software program recorded on a recording medium, such as a hard disk or a semiconductor memory, being read and executed by a program execution unit, such as a CPU or a processor. Here, a software program that implements the support apparatus, the generation apparatus, the analysis apparatus, and so forth of the embodiments and the modifications described above causes a computer to execute individual steps included in at least one flowchart illustrated in FIGS. 17A and 17B and FIGS. 50A and 50B.

The present disclosure is not limited to the above-described embodiments and modifications. The following cases are also included in the present disclosure.

(1) Each of the apparatuses described above is specifically a computer system including a microprocessor, a ROM, a RAM, a hard disk unit, a display unit, a keyboard, a mouse, and so forth. A computer program is stored in the RAM or the hard disk unit. The microprocessor operates in accordance with the computer program, and thus each apparatus achieves the function thereof. Here, the computer program is configured by combining instruction codes indicating instructions to a computer in order to achieve a predetermined function.

(2) Some or all of the elements included in each of the apparatuses described above may be constituted by a single system large scale integration (LSI). The system LSI is a super-multifunctional LSI manufactured by integrating components on one chip, and is specifically a computer system including a microprocessor, a ROM, a RAM, and so forth. A computer program is stored in the RAM. The microprocessor operates in accordance with the computer program, and thus the system LSI achieves the function thereof.

(3) Some or all of the elements included in each of the apparatuses described above may be constituted by an IC card or a single module that can be attached to and detached from the apparatus. The IC card or the module is a computer system including a microprocessor, a ROM, a RAM, and so forth. The IC card or the module may include the super-multifunctional LSI described above. The microprocessor operates in accordance with a computer program, and thus the IC card or the module achieves the function thereof. The IC card or the module may be tamper-resistant.

(4) The present disclosure may include the methods described above. The present disclosure may include a computer program of implementing these methods by a computer, or may include a digital signal composed of the computer program.

The present disclosure may include a computer-readable recording medium, such as a flexible disk, a hard disk, a CD-ROM, an MO, a DVD, a DVD-ROM, a DVD-RAM, a Blu-ray (registered trademark) Disc (BD), or a semiconductor memory, storing the computer program or the digital signal. The present disclosure may include a digital signal recorded on the recording medium.

In the present disclosure, the computer program or the digital signal may be transmitted via an electric communication line, a wireless or wired communication line, a network such as the Internet, data broadcasting, or the like.

The present disclosure may include a computer system including a microprocessor and a memory. The memory may store the above-described computer program, and the microprocessor may operate in accordance with the computer program.

The program or the digital signal may be implemented by another independent computer system by transferring the program or the digital signal recorded on a recording medium or by transferring the program or the digital signal via a network or the like.

A support apparatus, a generation apparatus, and an analysis apparatus according to the present disclosure are capable of appropriately supporting a search for a synthesis process, and are useful for an apparatus or a system for performing material development or synthesis of a new material.

What is claimed is:

1. A support apparatus comprising:
a generation apparatus; and
an analysis apparatus, wherein:
the generation apparatus executes (a-1) to (a-4) with i=1 to n, and generates process information 1 to process information n which are pieces of process information, the i being a natural number, the n being a natural number greater than or equal to 2,
in the (a-1), a material word extractor included in the generation apparatus extracts material words from a document i, the material words including a starting material word indicating a starting material and a target material word indicating a target material,
in the (a-2), a treatment word extractor included in the generation apparatus extracts a treatment word i from the document i, the treatment word i indicating a treatment i of generating the target material from the starting material,
in the (a-3), a condition extractor included in the generation apparatus extracts a synthesis condition i from the document i, the synthesis condition i being a condition i of the treatment i,
in the (a-4), a generator included in the generation apparatus associates the material words, the treatment word i, and the synthesis condition i with each other to generate process information i indicating a procedure i of generating the target material from the starting material, and the analysis apparatus includes:
a combiner that combines the pieces of process information to generate composite process information indicating a procedure of generating a target material from a starting material, and
an outputter that outputs the composite process information.

2. The support apparatus according to claim 1, wherein:
in a case where treatment words among a treatment word 1 to a treatment word n are identical, the combiner generates, from a synthesis condition 1 to a synthesis condition n, a comprehensive synthesis condition including synthesis conditions corresponding to the treatment words, and replaces the synthesis conditions with the comprehensive synthesis condition to generate the composite process information, and
in a case where the synthesis condition 1 to the synthesis condition n different from each other indicate a numerical value 1 to a numerical value n, respectively, a minimum numerical value among the numerical value 1 to the numerical value n is a numerical value p, a maximum numerical value among the numerical value 1 to the numerical value n is a numerical value q, and the numerical value p and the numerical value q satisfy $1 \le p \le n$, $1 \le q \le n$, and $p \ne q$, the comprehensive synthesis condition indicates a range from the numerical value p to the numerical value q.

3. The support apparatus according to claim 1, wherein the treatment word extractor extracts the treatment word i indicating at least one of a heat treatment, a mixing treatment, a drying treatment, or a dissolution treatment.

4. The support apparatus according to claim 1, wherein the condition extractor extracts, as the synthesis condition i, at least one of a temperature, a time, a pressure, or a rotation speed each of which is indicated by a numerical value and a unit.

5. The support apparatus according to claim 1, wherein;
the pieces of process information generated by the generator and the composite process information generated by the combiner are each configured to be graphable, and
the outputter displays the composite process information generated by the combiner in a graph format.

6. The support apparatus according to claim 1, wherein:
in a case where a target material word in first process information and a starting material word in second process information among the pieces of process information are identical material words and correspond to a common part common to the pieces of process information,
the composite process information generated by the combiner indicates a procedure of synthesizing, from starting materials indicated by the first process information, an intermediate material which is a material indicated by the identical material words corresponding to the common part, and generating a target material indicated by the second process information from the intermediate material.

7. The support apparatus according to claim 1, further comprising:
an analyzer, wherein;
the analyzer executes (b-1) to (b-3) with i=1 to n, and generates a data set 1 to a data set n which are data sets,
in the (b-1), the analyzer extracts author-related information i from the document i, the author-related information i being information about at least one of an author of the document i or an organization to which the author belongs, in the (b-2), the analyzer extracts apparatus-related information i from the document i, the apparatus-related information i being information about an apparatus, and in the (b-3), the analyzer generates a data set i indicating the author-related information i and the apparatus-related information i in association with each other.

8. The support apparatus according to claim 7, wherein:
the analyzer further executes (b-4) with i=1 to n in generation of the data sets,
in the (b-4), the analyzer extracts material information i from the document i, the material information i being information about a type of a material, and
in the (b-3), the analyzer generates the data set i further indicating the material information i in association with the author-related information i.

9. The support apparatus according to claim 8, wherein:
the analyzer further executes (b-5) with i=1 to n in generation of the data sets,
in the (b-5), the analyzer extracts amount information i from the document i, the amount information i being information about an amount of the material, and
in the (b-3), the analyzer generates the data set i further indicating the amount information i in association with the author-related information i.

10. The support apparatus according to claim 7, wherein;
the analyzer further executes (b-6) with i=1 to n in generation of the data sets,
in the (b-6), the analyzer extracts project-related information i from the document i, the project-related information i being information about a project of supporting the author or the organization, and
in the (b-3), the analyzer generates the data set i further indicating the project-related information i in association with the author-related information i.

11. A support apparatus comprising:
a generation apparatus; and
an analysis apparatus, wherein:
the generation apparatus executes (a-1) to (a-5) with i=1 to n, and generates process information 1 to process information n which are pieces of process information, the i being a natural number, the n being a natural number greater than or equal to 2,
in the (a-1), a material word extractor included in the generation apparatus extracts material words from a document i, the material words including starting material words indicating starting materials and a target material word indicating a target material,
in the (a-2), a treatment word extractor included in the generation apparatus extracts a treatment word i from the document i, the treatment word i indicating a treatment i of generating the target material from the starting materials,
in the (a-3), a condition extractor included in the generation apparatus extracts a synthesis condition i from the document i, the synthesis condition i being a condition i of the treatment i,
in the (a-4), a characteristic value extractor included in the generation apparatus extracts a characteristic value i related to the target material from the document i,
in the (a-5), a generator included in the generation apparatus associates the material words, the treatment word i, the synthesis condition i, and the characteristic value i with each other to generate process information i indicating a procedure i of generating the target material from the starting materials, the analysis apparatus includes:
a combiner that generates composite process information including a common part common to the pieces of process information and different parts different among the pieces of process information, and
an outputter that outputs the composite process information, and in a case where a synthesis condition 1 to a synthesis condition n different from each other and associated with the treatment word i common to the pieces of process information are the different parts, the combiner:
generates a comprehensive synthesis condition including the synthesis condition 1 to the synthesis condition n different from each other, and
replaces the synthesis condition i included in the process information i and associated with the common treatment word i with the comprehensive synthesis condition to generate the composite process information.

12. The support apparatus according to claim 11, wherein:
in a case where the synthesis condition 1 to the synthesis condition n different from each other indicate a numerical value 1 to a numerical value n different from each other, respectively,
in generation of the comprehensive synthesis condition, the combiner generates, as the comprehensive synthesis condition, a numerical value range defined by a minimum value and a maximum value among the numerical value 1 to the numerical value n different from each other.

13. The support apparatus according to claim 11, wherein;
in a case where the synthesis condition 1 to the synthesis condition n different from each other indicate a numerical value 1 to a numerical value n different from each other, respectively,
in generation of the comprehensive synthesis condition, the combiner performs clustering on a set including the numerical value 1 to the numerical value n different from each other to generate subsets, and generates the comprehensive synthesis condition from each of the subsets.

14. The support apparatus according to claim 11, wherein;
in a case where the common part includes a common target material word common to the pieces of process information and the different parts include a characteristic value 1 to a characteristic value n different from each other among the pieces of process information,
in generation of the composite process information, the combiner;
further generates a comprehensive characteristic value including the characteristic value 1 to the characteristic value n different from each other, and
replaces the characteristic value i included in the process information i with the comprehensive characteristic value.

15. The support apparatus according to claim 14, wherein;
the analysis apparatus further includes:
a synthesis condition acceptor that accepts an input synthesis condition which is a condition of a treatment, and
a characteristic value estimator that estimates a characteristic value of a target material indicated by the common target material word, the characteristic value being based on the input synthesis condition, the outputter further outputs the characteristic value estimated by the characteristic value estimator, and the characteristic value estimator estimates the characteristic value that is based on the input synthesis condition, in accordance with a relationship between the synthesis condition i included in each of the pieces of process information and the characteristic value i included in each of the pieces of process information.

16. The support apparatus according to claim 11, wherein:
in generation of the pieces of process information, the generation apparatus executes the (a-1) to the (a-5) with i=1 to m, and generates process information 1 to process information m, the m being a natural number greater than or equal to the n, the analysis apparatus further includes a searcher that searches the process information 1 to the process information m generated by the generation apparatus for the process information 1 to the process information n, and the searcher searches for the process information 1 to the process information n by using at least one of the treatment word i, the synthesis condition i, the characteristic value i, or a set of the material words.

17. The support apparatus according to claim 16, wherein;
in the (a-5), the generator adds bibliographic information of the document i to the generated process information i, and the searcher searches for the process information 1 to the process information n by further using the bibliographic information.

18. The support apparatus according to claim 17, wherein the bibliographic information indicates at least one of a name of an author of the document i, a publication date of the document i, a name of an organization to which the author belongs, or the number of citations of the document i.

19. The support apparatus according to claim 11, wherein;
the analysis apparatus further includes a facility searcher that performs a search for a facility capable of performing a treatment under the comprehensive synthesis condition generated by the combiner, by referring to, for each of facilities, facility information indicating a list of treatment conditions satisfiable by the facility, and the outputter further outputs information about the facility found through the search performed by the facility searcher.

20. A support apparatus comprising:
a generation apparatus; and
an analysis apparatus, wherein:
the generation apparatus executes (a-1) to (a-5) with i=1 to n, and generates process information 1 to process information n which are pieces of process information, the i being a natural number, the n being a natural number greater than or equal to 2, in the (a-1), a material word extractor included in the generation apparatus extracts material words from a document i, the material words including starting material words indicating starting materials and a target material word indicating a target material, in the (a-2), a treatment word extractor included in the generation apparatus extracts at least one treatment word i from the document i, the at least one treatment word i including the treatment word i indicating a treatment i of generating the target material from the starting materials, in the (a-3), a condition extractor included in the generation apparatus extracts at least one synthesis condition i from the document i, the at least one synthesis condition i including the synthesis condition i which is a condition i of the treatment i, in the (a-4), a characteristic value extractor included in the generation apparatus extracts a characteristic value i related to the target material from the document i, in the (a-5), a generator included in the generation apparatus associates the material words, the treatment word i, the synthesis condition i, and the characteristic value i with each other to generate process information i indicating a procedure i of generating the target material from the starting materials, the analysis apparatus includes:
a combiner that generates composite process information including a common part common to the pieces of process information and different parts different among the pieces of process information, and an outputter that outputs the composite process information, and in generation of the composite process information, the combiner associates the different parts with the common part such that a flow of generating a material branches from the common part to the different parts, to generate the composite process information.

21. An analysis apparatus comprising:
a combiner that combines pieces of process information to generate composite process information indicating a procedure of generating a target material from a starting material; and an outputter that outputs the composite process information, wherein each of the pieces of process information is information indicating a procedure of generating the target material from the starting material, and indicates material words including a starting material word indicating the starting material and a target material word indicating the target material, a treatment word indicating a treatment of generating the target material from the starting material, and a synthesis condition which is a condition of the treatment in association with each other.

22. A support method comprising:
executing, with a generation apparatus, (a-1) to (a-4) with i=1 to n, and generating, with the generation apparatus, process information 1 to process information n which are pieces of process information, the i being a natural number, the n being a natural number greater than or equal to 2;

in the (a-1), extracting material words from a document i, the material words including a starting material word indicating a starting material and a target material word indicating a target material;

in the (a-2), extracting a treatment word i from the document i, the treatment word i indicating a treatment i of generating the target material from the starting material;

in the (a-3), extracting a synthesis condition i from the document i, the synthesis condition i being a condition i of the treatment i;

in the (a-4), associating the material words, the treatment word i, and the synthesis condition i with each other to generate process information i indicating a procedure i of generating the target material from the starting material;

combining, with an analysis apparatus, the pieces of process information to generate composite process information indicating a procedure of generating the target material from the starting material; and outputting, with the analysis apparatus, the composite process information.

23. A non-transitory computer-readable recording medium storing a program that causes a computer to execute the support method according to claim 22.

24. An analysis method of analyzing pieces of process information, the analysis method comprising:

combining the pieces of process information to generate composite process information indicating a procedure of generating a target material from a starting material; and outputting the composite process information, wherein each of the pieces of process information is information indicating a procedure of generating the target material from the starting material, and indicates material words including a starting material word indicating the starting material and a target material word indicating the target material, a treatment word indicating a treatment of generating the target material from the starting material, and a synthesis condition which is a condition of the treatment in association with each other.

* * * * *